(12) United States Patent
Petyaev et al.

(10) Patent No.: US 11,696,920 B2
(45) Date of Patent: Jul. 11, 2023

(54) INTELLIGENT DELIVERY OF INGESTED AND ABSORBED MOLECULES

(71) Applicant: IMMD SP. ZO.O, Warsaw (PL)

(72) Inventors: Ivan M. Petyaev, Cambridge (GB); Marek Orlowski, Warsaw (PL)

(73) Assignee: IMMD SP. ZO.O, Warsaw (PL)

( * ) Notice: Subject to any disclaimer, the term of this patent is extended or adjusted under 35 U.S.C. 154(b) by 138 days.

(21) Appl. No.: 16/346,955

(22) PCT Filed: Nov. 3, 2017

(86) PCT No.: PCT/EP2017/078242
§ 371 (c)(1),
(2) Date: May 2, 2019

(87) PCT Pub. No.: WO2018/083271
PCT Pub. Date: May 11, 2018

(65) Prior Publication Data
US 2020/0261482 A1    Aug. 20, 2020

(30) Foreign Application Priority Data

Nov. 4, 2016 (PL) .......................... 419363
Nov. 7, 2016 (GB) .......................... 1618733
Apr. 5, 2017 (GB) .......................... 1705491

(51) Int. Cl.
*A61K 31/685* (2006.01)
*A61K 31/01* (2006.01)
*A61K 31/202* (2006.01)
*A61K 47/44* (2017.01)

(52) U.S. Cl.
CPC ............ *A61K 31/685* (2013.01); *A61K 31/01* (2013.01); *A61K 31/202* (2013.01); *A61K 47/44* (2013.01)

(58) Field of Classification Search
CPC .. A61K 2300/00; A61K 31/01; A61K 31/047; A61K 31/05; A61K 31/065; A61K 31/122; A61K 31/353; A61K 31/202; A61K 31/685; A61K 47/44; A61K 9/4858; A23G 1/38; A23G 2200/08; A61P 1/16; A61P 21/00; A61P 35/00; A61P 43/00; A61P 9/00
See application file for complete search history.

(56) References Cited

U.S. PATENT DOCUMENTS

| | | | |
|---|---|---|---|
| 7,632,532 B2 * | 12/2009 | McKee ............... | A23G 1/32 426/548 |
| 7,641,924 B2 * | 1/2010 | Mizumoto ........... | A61K 38/16 424/757 |
| 2004/0219188 A1 * | 11/2004 | Comer .................. | A23L 33/15 514/23 |
| 2006/0134294 A1 | 6/2006 | McKee | |
| 2007/0116696 A1 * | 5/2007 | Riley ..................... | A61K 36/62 424/94.5 |
| 2008/0194703 A1 * | 8/2008 | Sabio Rey .............. | A23L 27/60 514/762 |
| 2011/0288012 A1 | 11/2011 | Somekawa et al. | |
| 2013/0243845 A1 * | 9/2013 | Geron ................... | A61K 31/375 424/440 |
| 2014/0170247 A1 * | 6/2014 | Hendler ................ | A61K 31/385 424/732 |
| 2014/0179781 A1 * | 6/2014 | Waibel ................... | C11B 3/006 426/607 |
| 2014/0199414 A1 * | 7/2014 | Sampalis ............... | A61P 35/00 424/643 |
| 2014/0288187 A1 | 9/2014 | Petyaev | |
| 2015/0250691 A1 * | 9/2015 | Piccardi ................ | A61K 8/925 514/560 |

FOREIGN PATENT DOCUMENTS

| | | |
|---|---|---|
| AU | 2011218634 A1 | 9/2011 |
| JP | 5-292885 | 11/1993 |
| JP | 2015-502150 | 1/2015 |
| WO | 2009037562 A2 | 3/2009 |
| WO | 2010/064714 | 6/2010 |
| WO | 2010074940 A1 | 7/2010 |
| WO | 2010125516 A1 | 11/2010 |
| WO | 2011107259 A1 | 9/2011 |
| WO | 2012104576 A2 | 8/2012 |
| WO | 2012131493 A1 | 10/2012 |
| WO | 2013079967 A1 | 6/2013 |
| WO | 2015073515 A1 | 5/2015 |

OTHER PUBLICATIONS

Lipp et al. (J of Food Composition and Analysis, 2001, 14, 399-408). (Year: 2001).*
Backes et al., (2016) The clinical relevance of omega-3 fatty acids in the management of hypertriglyceridemia. Lipids Health Dis 15(1): 118; 12 pages.
Barber and Barber (2002) Lycopene and prostate cancer. Prostate Cancer Prostatic Dis 5(1): 6-12.
Bazan et al., (2011) Endogenous signaling by omega-3 docosahexaenoic acid-derived mediators sustains homeostatic synaptic and circuitry integrity. Mol Neurobiol 44(2): 216-222.

(Continued)

*Primary Examiner* — Umamaheswari Ramachandran
(74) *Attorney, Agent, or Firm* — Wenderoth, Lind & Ponack, L.L.P.

(57) ABSTRACT

The present application is concerned with methods for increasing the bioavailability and/or activity of agents and in particular allows selective targeting of an agent to, or via, the liver or allows the liver to be bypassed. By selecting which of saturated fatty acids (SFA), short chain fatty acids (SCFA), medium chain fatty acids (MCFA), polyunsaturated fatty acids (PUFA), monounsaturated fatty acids (MUFAs) and long chain fatty acids (LCFA) are present in a composition and which predominates it is possible to substantially boost bioavailability and also to selectively target whether an agent is delivered to, or via, the liver or alternatively bypasses the liver. The approach is a versatile platform technology which may be applied to agents in general helping achieve better and more efficient delivery. In one preferred embodiment particular carotenoids are employed to further influence whether delivery is to, or via, the liver, or bypasses the liver.

8 Claims, 1 Drawing Sheet

(56) References Cited

OTHER PUBLICATIONS

Bernstein et al., (2012) A meta-analysis shows that docosahexaenoic acid from algal oil reduces serum triglycerides and increases HDL-cholesterol and LDL-cholesterol in persons without coronary heart disease. J Nutr 142(1): 99-104.
Burton-Freeman and Sesso (2014) Whole Food versus Supplement: Comparing the Clinical Evidence of Tomato Intake and Lycopene Supplementation on Cardiovascular Risk Factors1,2 . Adv Nutr 5(5): 457-485.
Clinton et al., (1996) cis-trans lycopene isomers, carotenoids, and retinol in the human prostate. Cancer Epidemiol Biomarkers Prev 5(10): 823-833.
Fritsche (2015) The science of fatty acids and inflammation. Adv Nutr 6(3): 293S-301S.
Gajendragadkar et al., (2014) Effects of oral lycopene supplementation on vascular function in patients with cardiovascular disease and healthy volunteers: a randomised controlled trial. PLoS One 9(6): e99070. 13 pages.
Giovannucci (2002) A review of epidemiologic studies of tomatoes, lycopene, and prostate cancer. Exp Biol Med (Maywood) 227(10): 852-859.
Kim et al., (2010) n-3 polyunsaturated fatty acids-physiological relevance of dose. Prostaglandins Leukot Essent Fatty Acids 82(4-6):155-158.
Mills et al., (1989) Cohort study of diet, lifestyle, and prostate cancer in Adventist men. Cancer 64(3): 598-604.
Ried and Fakler (2011) Protective effect of lycopene on serum cholesterol and blood pressure: Meta-analyses of intervention trials. Maturitas 68(4): 299-310.
Ried et al., (2009) Dark chocolate or tomato extract for prehypertension: a randomised controlled trial. BMC Complement Altern Med 9: 22. 12 pages.
Schwarz et al., (2008) Lycopene inhibits disease progression in patients with benign prostate hyperplasia. J Nutr 138(1): 49-53.
Tajuddin et al., (2016) Prescription omega-3 fatty acid products: considerations for patients with diabetes mellitus. Diabetes Metab Syndr Obes 9:109-118.
Ulven and Holven (2015) Comparison of bioavailability of krill oil versus fish oil and health effect. Vasc Health Risk Manag 11:511-524.
Van Breemen et al., (2011) Antioxidant effects of lycopene in African American men with prostate cancer or benign prostate hyperplasia: a randomized, controlled trial. Cancer Prev Res (Phila) 4(5): 711-718.
Walz et al., (2016) Omega-3 polyunsaturated fatty acid supplementation in the prevention of cardiovascular disease. Can Pharm J (Ott) 149(3): 166-173.
Weiser et al., (2016) Docosahexaenoic Acid and Cognition throughout the Lifespan. Nutrients 8(2): 99. 40 pages.
Anonymous: "Altacor Eye Products—Maintain healthy vision". Apr. 25, 2016 (Apr. 25, 2016), Retrieved from the Internet: URL: https://web.archive.org/web/20160425114804/http://altacoreyeproducts.co.uk:80/index.php.maintain-healthy-vision [retrieved on Jan. 23, 2018]; 2 pages.

* cited by examiner

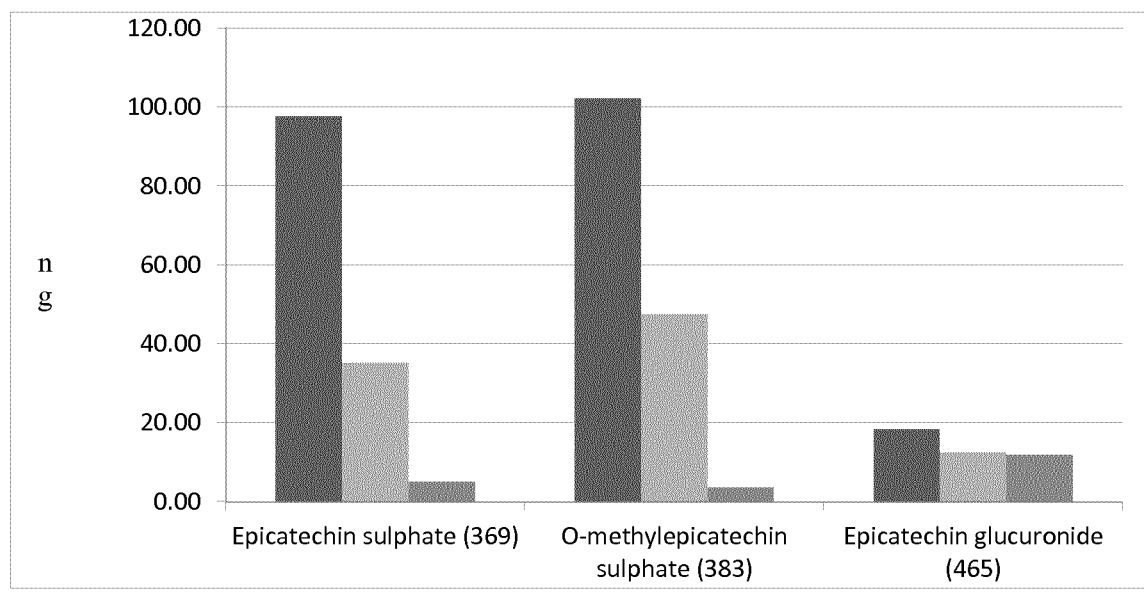

INTELLIGENT DELIVERY OF INGESTED AND ABSORBED MOLECULES

FIELD OF THE INVENTION

The present invention is concerned with ways to target to, or via, the liver following oral consumption of an agent or to bypass the liver and deliver an agent elsewhere following oral consumption. The present invention is also concerned with ways to achieve increased bioavailability following oral consumption of an agent. That increased bioavailability may, for instance, be at the liver, in the blood stream or at a particular tissue. The present invention provides ways to selectively direct the transport of ingested and absorbed molecules, or particles, of natural or synthetic origin of a xenobiotic, amphiphilic, lipophilic or hydrophobic nature to either promote their direct delivery to, or via, the liver or to help bypass delivery to the liver and instead target other tissues. The approach is particularly effective for water insoluble agents. In one particularly preferred instance, the invention is concerned with ways to achieve increased bioavailability following oral consumption of essential fatty acids (EFAs), such as ω-3, ω-6 and ω-7 fatty acids (i.e. an omega-3, omega-6 or omega 7 fatty acid).

BACKGROUND OF THE INVENTION

Bioavailability typically refers to the extent and rate at which active agents become available, for instance as measured by the rate or amount of the agent that enters the systemic circulation. Poor bioavailability is a key issue for many substances particularly when administered orally. Hence, whilst oral administration is the most convenient route it is one whose use is often hampered by poor bioavailability. Orally administered agents typically first pass through the intestinal wall and then proceed via one of two main pathways. The first pathway is for the absorbed molecules to pass via the portal vein system to the liver. The other main pathway is direct passage into the circulation via the lymph system, bypassing the liver. Which pathway a given active agent proceeds by can influence the bioavailability of the substance and also how likely the agent is to be modified by metabolic processes. For instance, processing of a given agent via the liver can involve, for instance, its oxidation, hydroxylation, conjugation, metabolic conversion, and/or excretion with bile of these molecules, in metabolized or non-metabolized forms, back to the intestine. Such metabolic processes may modify a given active agent or reduce the amount of the active agent available in the circulation. In other instances, agents delivered via the liver may be incorporated into, associated with, or bound to a carrier, which then allows the agent and associated carrier to pass into the circulation and subsequently to the tissues. In such instances, without such association with a carrier, the agent, or its active group, may not be able to reach the circulation and then subsequently be (bio-)available to other organs and tissues in the body. In more than one more instance, an agent delivered to the liver can be metabolically modified in such way that it would become either easier transportable or even more hydrophilic that it will be more ready to circulate in the blood itself.

There is an ongoing need for ways to promote bioavailability of agents following oral administration. Increasing bioavailability is not just important for drugs and pharmaceuticals, but also in other areas, such as in nutraceuticals and food supplements. Increasing bioavailability can lead to the same amount of agent being administered, but an increase in the amount of the agent reaching the circulation or target tissue. Increasing bioavailability can also mean that less of an agent can be administered to achieve the same, or greater, level of the agent, for instance in the circulation. That can be important in helping reduce costs as it can mean less of an active agent is needed to achieve the same or greater effect. It can also be important for compliance. For instance, the benefits of consuming various fish oils, particularly those rich in omega 3 fatty acids, are recognized, but often a very high amount of such oils or supplements containing omega fatty acids has to be consumed. In the case of individuals where omega 3 is being consumed to reduce triglyceride, the recommended amount for an individual is 4 grams of omega 3 on a daily basis, but for many regularly consuming such a large amount of omega 3 oil which is often derived from fish is not a pleasant experience. Many subjects discontinue taking such omega 3 oil supplements despite the fact that there are clear health benefits in continued consumption of such supplements. Further, consumption of such large amounts of omega 3 oils can have a number of detrimental side-effects. For instance, the frequency and severity of gastrointestinal side effects may be increased. Moreover, plasma/serum concentration of essential fatty acid levels, such as that of omega 3, may also rise after oral administration to a level exceeding that expected for the physiological dietary level, rather than the essential fatty acids being focused to the liver. This may lead to another set of complications, which include but not limited to muscle and join pain, disturbances in the clotting system and bleedings, elevation of LDL cholesterol. Achieving higher bioavailability of essential fatty acids, such as that of omega 3 fatty acids, particularly in terms of delivery to the liver would allow less, essential fatty acids, such as omega 3 oil, to be initially consumed, resulting in a higher chance of compliance as the subject will no longer have to consume such large amounts of fish based oils and reduced chance of side-effects. Another example of an agent showing poor bioavailability following oral consumption is trans-resveratrol. For instance after consumption of publicly available trans-resveratrol formulations, whilst 95% is absorbed, in general only 5% is bioavailable.

Whilst oral administration is therefore the most convenient route for administration, compared to other routes such as intravenous injection, it is hampered via the poor bioavailability typically seen with oral consumption. There is therefore a need to provide ways to increase bioavailability of orally administered agents. There is also a continuing need to promote the targeting of drugs when administered orally, so not just the level of agent being delivered, but the location it is delivered to is controlled. By increasing the targeting of an agent to a chosen target organ or tissue, again less agent may be needed and the amount having to be taken by the subject is also potentially again decreased, both helping to reduce costs and also boost compliance.

SUMMARY OF THE INVENTION

The present invention provides in particular ways to: (i) increase the bioavailability of an agent; (ii) help target an agent to a desired location; and/or (iii) increase the activity of an agent. The invention is based, at least in part, by the finding that the use of particular lipids promotes the passage of a given agent via a particular route following oral administration, in particular the use of SFAs (saturated fatty acids), SCFA (short chain fatty acids) and/or MCFA (medium chain fatty acids) promote passage via the portal vein and liver or alternatively the use of MUFAs (monounsaturated fatty acids), PUFAs (polyunsaturated fatty acids) and/or LCFA (long chain fatty acids) to promote delivery via the lymphatic system. Further, the use of particular SFA, SCFA, MCFA, PUFA, MUFA or LCFA can help increase bioavailability of an agent it is administered with. In a particularly preferred instance SFA is employed in the invention to promote delivery to, or via, the liver. In a further particularly preferred instance, a PUFA or a MUFA, and preferably a PUFA is employed to promote bypassing the liver.

The present invention provides a composition for use in a method of targeting or enhancing delivery of a water insoluble agent or agents, wherein:
(a) the method is for targeting and/or enhancing delivery of the agent or agents to, or via, the liver, where the composition comprises: (i) at least 5% of saturated fatty acids (SFA) and/or short chain fatty acids (SCFA) and/or medium chain fatty acids (MCFA); and (ii) the water insoluble agent or agents; or
(b) the method is for targeting and/or enhancing delivery of the agent or agent(s) so that it bypasses the liver, where the composition comprises: (i) at least 5% of monounsaturated fatty acids (MUFA), polyunsaturated acids (PUFA) and/or long chain fatty acids (LCFA); and (ii) the water insoluble agent or agents.

The present invention further provides a composition comprising an omega 3 fatty acid or acids and at least 5% of saturated fatty acids (SFA) and/or short chain fatty acids (SCFA) and/or medium chain fatty acids (MCFA).

The present invention also provides a composition comprising: (a) one or more Essential Fatty Acids (EFA); (b) one or more carotenoids in an amount of at least 0.001% by weight; and (c) at least 5% of saturated fatty acids (SFA) and/or short chain fatty acids (SCFA) and/or medium chain fatty acids (MCFA).

It has been further identified that the presence of carotenoids may be used to influence further the pathway taken and hence whether delivery is to, or via, the liver or alternatively the liver is bypassed. Thus, the presence of carotenoids in the compositions of the invention can be employed to additionally influence targeting of an active agent and particularly Essential Fatty Acids. Hence, in one particularly preferred embodiment a composition of the invention will also comprise one or more carotenoid and will especially comprise both one or more carotenoid and one or more Essential Fatty Acid (EFA). Particularly preferred sources of EFAs include DHA and EPA, particularly DHA.

Hence, the present invention also provides a composition for use in a method of increasing the bioavailability and/or activity of one or more Essential Fatty Acids (EFA) or in facilitating their delivery to, or via, the liver, of the EFA wherein the composition is administered orally and comprises: (a) one or more Essential Fatty Acids (EFA); (b) a carotene in an amount of at least 0.001% by weight; and (c) one or more Saturated Fatty Acids (SFA) in an amount of at least 5% by weight.

The invention also provides a composition for use in a method of bypassing the liver following oral administration of the composition, wherein the composition comprises: (a) one or more Essential Fatty Acids (EFA); (b) one or more xanthophyll in an amount of at least 0.001% by weight; and (c) one or more Saturated Fatty Acids (SFA) in an amount of at least 5% by weight.

The present invention is also particularly useful for the delivery of statins. Hence, the invention further provides a composition for use in a method of delivering a statin to the liver, the method comprising administering to a subject in need thereof a composition comprising the EFA, a carotenoid and at least 10% SFA.

Particularly preferred compositions of the invention include those comprising cocoa butter, for instance as a source of the SFA.

BRIEF DESCRIPTION OF THE FIGURES

FIG. 1. Shows the results of a pharmacokinetic study of epicatechins formulated with SFA or PUFA. The three columns in each group are, going from left to right results for the catechin formulation with SFA, the catechin formulation with PUFA, and a control extract preparation without any lipids.

DETAILED DESCRIPTION OF THE INVENTION

Herein, any reference to a term in the singular also encompasses its plural. Hence, reference herein to the singular, for instance as denoted by "a" or "an", also includes the plural unless otherwise stated. Hence, where terms such as "a" or "an" are used, one or more of what is set out may be employed, though in one embodiment just one of what is specified may be employed. Where the term "comprising", "comprise" or "comprises" is used in a particular embodiment, also encompassed are the embodiments wherein said term is substituted for "consisting of", "consist of" or "consists of" respectively, as well as embodiments where the term "comprising", "comprise" or "comprises" is substituted for "consisting essentially of", "consist essentially of" or "consists essentially of" respectively. Hence, in one preferred embodiment, a composition of the invention will consist of the recited ingredients. In another it will comprise them. In a further instance, it will consist essentially of the recited constituents. Any reference to a numerical range or single numerical value also includes values that are about that range or single value. Where percentage amounts are referred to, that typically means percentage amounts by weight, particularly weight for weight (w/w), unless otherwise indicated. "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Anywhere herein where a compound is referred to, if a salt of such compound may also be employed, that is also encompassed in the invention, particularly the use of such physiological acceptable salts. Where a given entity is referred to herein for use in a particular method, the method itself is also provided as is use of the entity in the manufacture of a medicament for use in such a method. Where a product for use in a method of treatment is referred to, the invention also provides the equivalent method of treatment and for the use of the product in the manufacture of a medicament. Where more than one composition is administered, they may, for instance, separately, simultaneously or sequentially.

Overview

The present invention is based on the unexpected finding that by using a composition comprising particular fatty acids it is possible to target agents so that they are either preferentially delivered to, or via, the liver or bypass the liver. In one instance, delivery may be to the liver and subsequently to the circulation, particularly where an essential fatty acid is being delivered. In another approach, delivery may bypass the liver and hence target to the lymphatic system, again in particular instances such an approach may be used in some cases for essential fatty acids.

The approach provided may also be used to increase bioavailability of an agent at a chosen site, for instance at the liver, or in the peripheral tissues. The invention is especially applied where a given agent is being administered orally. Hence, in one instance the approach provided allows for the selective targeting of an agent to either to, or via, the liver or to bypass the liver based on the fatty acids included in the compositions employed. It has been unexpectedly found that compositions comprising an agent and SFA (saturated fatty acids), and/or SCFA (short chain fatty acid) and/or medium chain fatty acids (MCFA) may be used to increase bioavailability at the liver of an agent and also to promote targeting, or delivery, of an agent to, or via, the liver. It has also been unexpectedly found that compositions comprising an agent together with PUFA (polyunsaturated fatty acids), and/or MUFA (monounsaturated fatty acids) and/or LCFA (long chain fatty acids) and in particular comprising PUFAs may be used to bypass the liver and hence promote delivery to other tissues, particularly via the lymph and then into the circulation. Hence, by choosing which of a SFA, SCFA, MCFA, MUFA, PUFA and LCFA is incorporated into, or predominates in, a composition of the invention it is possible to selectively achieve delivery of an agent to, or via, the liver, or bypassing the liver. In one preferred instance as a result the level of the delivered agent in the circulating blood is increased. For instance, serum levels may be increased.

The invention may be employed to selectively deliver an agent to, or via the liver. In such an embodiment a composition may be employed which comprises a SFA, SCFA and/or MCFA and an active agent, particularly any of the active agents described herein. In one preferred embodiment a SFA is used. In another preferred embodiment SCFA is used. In a further embodiment, a MCFA may be used. In a further preferred embodiment at least two and preferably three of a SFA, SCFA and/or MCFA may be employed in a composition of the invention.

In one particularly preferred instance, the agent in a composition of the invention or employed in the agent is a water insoluble agent or is at least partially water insoluble, in particular the agent is water insoluble. In a further particularly preferred instance the agent is fat soluble, particularly soluble in the fats stated to be present in the composition. In a further preferred instance, the agent is both water insoluble and fat soluble.

Possible preferred active agents include the three particularly preferred groups of active agents described herein, namely carotenoids, polyphenols and essential fatty acids, ω-3, ω-6 and ω-7 fatty acids (i.e. an omega-3, omega-6 or omega 7 fatty acid), and EFA. In one especially preferred embodiment of the invention provided a composition comprises one or more essential fatty acids (EFAs) and one or more carotenoids. In a particularly preferred instance the EFA is omega-3. As described further herein, the subject may be one with any of the conditions referred to herein. It may be that the invention is being used prophylactically to help prevent, or reduce the risk of, a condition or to treat a condition. It may be that the invention is simply employed to help ensure that an individual receives the recommended amount of an agent, for instance in the bioavailable form and the agent reaches the recommended blood level. One advantage of the approach provided is that it may be necessary to give less of an agent, for instance to achieve the same effect, because of the impact of the claimed approach on bringing about targeting to, or via, the liver or bypassing the liver. In some cases the invention may be used to influence the level in the blood of lipid levels, particularly where an essential fatty acid is present in a composition of the invention, for instance in one preferred instance a composition comprising an EFA may be used to decrease triglyceride levels, particularly serum triglyceride levels. In one especially preferred embodiment, the invention may be employed to increase the bioavailability of an EFA.

In an alternative embodiment, the invention may be employed to bypass the liver and hence promote delivery via the lymph and into the circulation. In such embodiments, the composition provided preferably comprises a PUFA and/or a MUFA and/or LCFA and in particular a PUFA or LCFA and especially a PUFA, together with an agent to be delivered. Such an approach may be used to promote delivery to tissues in the body other than the liver and may be particularly useful where the agent to be delivered is one whose activity is usually reduced by the liver or where it is desired not to deliver the agent to the liver because it may have, for instance, some detrimental effect on it.

In one preferred instance of the invention, a composition provided by, or used in, the invention may comprise SFA, SCFA, MCFA, MUFA, PUFA and/or LCFA and an active agent, particularly it may comprise SFA, SCFA and/or MCFA or alternatively it may comprise MUFA, PUFA and/or LCFA. In a particularly preferred instance, the composition may comprise SFA. In a further particularly preferred instance, the composition may comprise PUFA or MUFA and particularly PUFA. Which of the fatty acids employed will typically depend on whether it is desired to target to, or via, the liver or alternatively to bypass the liver. In a preferred instance, any of the compositions discussed herein may also comprise a phosphatidylcholine. As discussed elsewhere herein any suitable formulation may be employed. Where the composition is to be employed for delivery to, or via, the liver, the composition may comprise a SFA, SCFA, and/or MCFA. Where the composition is to be employed to bypass the liver a PUFA and/or MUFA and/or LCFA may be present, for instance at least one of a PUFA, MUFA, and LCFA may be present, for example at least two or in some instances all three may be present. In a particularly preferred instance, MUFA and/or PUFA may be present, particularly a PUFA.

Any of the agents discussed herein may be present in a composition of the invention. A particularly preferred agent for employing in the invention is a water insoluble agent. In one instance, the agent is an active agent already when administered, in a further instance, the agent may be one which only becomes active after it is administered, for example because it is modified in the body in some way, such as in the liver, to activate it. In one instance, one agent may be present in a composition of the invention. In another instance, one or more active agent may be present. For instance, in some embodiments, one, two, three, four, five, six or more active agents may be present in a composition of the invention and, for instance, such numbers of any of the specific active agents may be present.

In a further aspect of the invention it may be that whether an agent is delivered to, or via, the liver, or bypasses it is a function of the size of chylomicron that a composition of the invention gives rise to. In particular, it may be that in some instances, chylomicrons of about 0 to 400 nm favor targeting to, or via, the liver, whilst those in the range of about 400 to 600 nm lead to some delivery to, or via, the liver, but also bypassing the liver as well, whilst chylomicrons in the size range of 600 to 800 nm may lead to bypassing the liver. Hence, in one preferred instance, in any of the embodiments described herein where the intention is to target to, or via, the liver, or at least to favor it, the composition employed may give rise to chylomicrons in the range of 0 to 600 nm in diameter, for instance, from 50 to 600 nm in diameter, such as from 100 to 600 nm in diameter. For instance, the chylomicrons may be in the size range of 100 to 500 nm in diameter, for instance, from 200 to 400 nm in diameter. It may be that the chylomicrons are up to 600, 550, 500, 450 or 400 nm in diameter or at least 100, 150, 200 or 250 nm in diameter or in a range comprising any pair of those values as endpoints. In an especially preferred instance, the chylomicrons may be 200 to 400 nm in size. Conversely, where it is desired to bypass the liver, it may be that the chylomicrons are in the size range of 400 to 800 nm in diameter, for instance from 450 to 800 nm in diameter, such as from 500 nm to 800 nm, such as from 550 to 600 nm in diameter. In a preferred instance, the size range of the chylomicrons may be from 600 to 900 nm in diameter. In a particularly preferred instance, the size range may be from 600 nm to 800 nm in diameter. In any of the embodiments of the invention, a composition may be such that it gives rise to chylomicrons of such size to allow for targeting to, or via, the liver or bypass it, for instance by giving rise to chylomicrons of the above stated size. Whilst the invention is not constrained by any particular theory it is considered that the size and saturation of the fatty acid may influence chylomicron size and so promote targeting via a particular route. For any of the size ranges specified, in one preferred instance the size range specified is the average size of the chylomicrons. It may be that at least 75%, 80%, 85%, 90% or 99% of the chylomicrons comprising the agent to be delivered fall in that size range. As discussed herein, in one preferred instance carotenoids are present in the compositions provided and further influence where targeting is to and that is particularly the case for delivery of EFAs.

Bioavailability & Targeting

In one preferred instance, the invention may be employed to increase bioavailability of a given agent. For instance, via employing the invention bioavailability, particularly in the circulation, may be significantly improved. Hence, employing the invention may enhance bioavailability. Increasing bioavailability may be used as a way to: (i) increase the amount of the agent reaching the preferred target; and/or (ii) reduce the amount of active agent that needs to be administered in the first place, for instance to achieve a given effect. It may be administration of a composition of the invention increases bioavailability by, for instance, at least 10%, at least 25%, at least 50% or at least 100%. In some instances, the invention may bring about at least a doubling of bioavailability. In others the level of increase may be, for instance, at least three, four, five, six or seven fold. In some instances, the level of bioavailability may be increased, for example, at least ten-fold. In other instances, the level of increase may be, for instance, between any pair of the above mentioned values, for instance from 10% to ten-fold, from 25% to five-fold and so on. In one preferred instance, the level of an agent in the serum is at least doubled compared to administration of a control composition without the SFA, PUFA, MUFA, SCFA, or LCFA that is used in a composition of the invention. It may be that an increase of at least five fold is seen. For instance, an increase of at least ten-fold is seen. It may be that an increase of at least twenty fold is seen. The increase may, for instance, be from two to twenty-fold.

Bioavailability may be, for instance, measured in terms of the proportion of an agent that enters the systemic circulation and in particular the portion in the systemic circulation which is able to have a physiological effect. An increase in bioavailability may be taken as the amount of active agent that enters the systemic circulation compared to the amount when the active agent is administered in a composition which lacks lipid or, for instance the SFA, PUFA, MUFA, SCFA, or LCFA present in the composition. So, for instance, the comparison may be between a composition of the invention comprising SFA and the equivalent composition lacking a SFA administered via the same route. An equivalent composition may also be referred to as a reference composition. In a further instance, the comparison may be between the availability of the agent when administered as a composition of the invention orally compared to the availability when the same composition is administered intravenously. In an especially preferred embodiment the invention is used where the agent is administered orally.

In a further embodiment, the level of bioavailability referred to may be that at a target tissue. A target tissue may be, for instance the brain, blood, skin, skeletal muscles, nerves, spinal cord, heart, liver, kidneys, stomach, small intestine, duodenum, muscles, lung, pancreas, intestine, bladder, reproductive organs, bones, tendons, or other internal organs or tissues. In one instance, the level of bioavailability may be that at the liver. In one embodiment the level of bioavailability may be that in an organ other than in the liver. In a further preferred embodiment, the level of bioavailability may be that in the circulation. In another preferred instance, the level of bioavailability may be that in the prostate.

In one particularly preferred instance, it may be that bioavailability is assessed by measuring the amount of the agent in the systemic circulation following administration of a composition of the invention. For instance, it may be that bioavailability is assessed by measuring the serum concentration of an agent of interest following oral administration. It may be that such measurement is performed at several time points, for instance once a day or once a week to assess the level of agent, for example in the blood stream. In some cases, it may be that serum concentration may be compared before oral consumption of a composition of the invention and then after 1, 2, 3 or 4 weeks, particularly after 2 and/or 4 weeks and in particular after 2 weeks. In other instances the level of bioavailability may be that measured hours after administration, for instance after 1, 2, 3, 4, 5 or 6 hours after administration, for example that may be the case in a preferred instance where the agent is a polyphenol, particularly any of those mentioned herein. In some instances of the invention, a method is provided comprising comparing a composition of the invention comprising SFA, SCFA and/or MCFA with an equivalent composition of the invention comprising PUFA, MUFA and/or LCFA and then determining which promotes bioavailability, such as bioavailability measured in the systemic circulation. For any given agent, the invention provides a composition comprising whichever of a SFA, SCFA and/or MCFA or a PUFA, a MUFA and/or LCFA promotes bioavailability to a chosen location to a greater degree than the other(s).

In some instances, it may be that the approach of the invention selectively targets an agent to the liver. For instance, the increase in the amount of the agent seen in the liver is seen at any of the increased levels mentioned herein, for instance the increase may be two, three, four, five, six or seven-fold or more, it may be at least a 25%, 50%, 75% or more increase. In one preferred instance, the increase is at least double. In a further preferred instance, the increase is at least five-fold. In other embodiments of the invention, the increase may be assessed by the amount of active agent reaching the circulation compared to a formulation which is the same, apart from lacking the fatty acid component. Measurement of an amount of agent may be, for instance, assessed by liver biopsy. Lipoprotein fractionation may also be employed. Alternatively, the amount of an agent may be measured in the serum. Such measurements may be, for instance, performed at a set time point after consumption of a composition of the invention. In some instances, a composition of the invention may be assessed in a non-human test animal, particularly assessment of targeting amounts to a particular site and/or activation of an agent, examples of non-human animals include non-human mammals, particularly rodents such as rats or mice or animals such as rabbits, guinea pigs, sheep and pigs. In one preferred instance, EFA levels may be assessed in a non-human animal. In one preferred instance, bioavailability is measured at a particular tissue, for instance, by sampling the tissue. Measurement at the tissues may be, for instance, done when the aim is to bypass liver based delivery. That may be particularly the case where PUFA, MUFA and/or LCFA is being employed to bypass the liver. In some cases more than one measurement needs to be taken and it may not be readily possible to take multiple biopsy samples from the liver or tissue and hence instead bioavailability can be assessed indirectly through impact of the ingested agent on the level of a specific metabolite produced by the targeted tissue, or by measuring a specific function of the targeted organ. Any suitable means may therefore be used to measure the impact of the invention. In some instances, measurements may be made and compared before and after administration of a composition of the invention. For instance, measurements may be taken before administration and then one or more times after administration, such as at set time points.

The invention provided may be, for instance, used to improve the pharmokinetics of a given agent, particularly in terms of serum levels of the agent, or a marker for it, following oral consumption. In any of the embodiments described herein, synergy may be seen, that is the effect of a composition of an invention is greater than any of the individual constituents or what would be expected from the individual levels of activity for each constituent. In one preferred instance a synergistic effect is seen in terms of increased delivery to, or via the liver, or in terms of bypassing the liver. In another preferred instance, synergy may be seen in terms of the level of an agent in the serum following oral administration. In a further preferred embodiment, chylomicrons may be measured. Examples of synergy include improvement by, for instance, at least 10%, at least 25%, at least 50%, or at least 100%, such as a doubling, or trebling of efficacy or a range with any pair of those values as endpoints.

In one embodiment, the improvement seen is that compared to a control which either simply comprises the agent(s) without the addition of SFA, SCFA, and/or MCFA, particularly SFA or without the addition of PUFA, MUFA and/or LCFA. In one instance, where the test composition comprises of SFA, SCFA, and/or MCFA, the control composition comprises PUFA, MUFA and/or LCFA or vice versa. For instance, where SFA is employed it may be that the control comprises PUFA or again vice versa. Apart from that, typically the control will be the same as the composition under test.

In particularly preferred instances of the invention SFA, SCFA, and/or MCFA, particularly SFA, is used, to increase bioavailability of an agent, particularly in the serum. In a further preferred embodiment, SFA, SCFA, and/or MCFA, particularly SFA, is used to promote targeting to, or via, the liver. In a further preferred embodiment, PUFA, MUFA and/or LCFA, particularly a PUFA and/or MUFA, and especially a PUFA is used to promote bioavailability in tissues other than liver. In another preferred instance, PUFA, MUFA, LCFA, particularly PUFA and/or MUFA and especially PUFA is used to bypass delivery via the liver.

Agents to be Delivered

The invention may be employed to target agents in general to, or via, the liver. The invention may also be used to bypass the liver. Any suitable agent may be present in a composition of the invention and various different classes of agents are discussed herein. In one especially preferred instance of the invention, an agent to be delivered may be one that is insoluble in water. In other instances, the agent may be water insoluble or partially water soluble. It may be that the agent is hydrophobic. The agent may be lipophilic. The agent may be amphiphilic. A water insoluble agent encompasses situations where the agent comprises an active that is surrounded or encapsulated by a layer which means overall the resulting structure is water insoluble. Hence, in the invention the active may be something that is wholly or partially water soluble, but that it is encapsulated so that overall the agent is not water insoluble. In other instances, the agent may be a drug, compound, or other active that is itself water insoluble. The agent may be one associated with promoting or enhancing health, the agent may be a nutritional agent. An agent may be a health supplement. The agents may be, for instance, prophylactic or therapeutic. In one particularly preferred embodiment, the composition of the invention is a nutraceutical or pharmaceutical composition. In one preferred embodiment of the invention the composition is not a food stuff. In other embodiments a composition of the invention may be a food stuff comprising the recited constituents.

In one preferred instance, it may be that the agent to be delivered only undergoes activation after consumption for instance because it is a prodrug that is cleaved in the body to give the active form, or it is modified in other ways in the body, for example by modification in the liver, such as by oxidation, hydroxylation, conjugation, or metabolic conversion in the liver. In other preferred instances, the agent in a composition of the invention is already an active agent. In a further preferred instance, an agent may be one which is either included in the composition associated with a carrier or becomes associated with a carrier in the body, where the carrier is a naturally occurring one present in the body.

Illustrative types of active agents and specific agents are discussed below but the invention provided may be employed with any suitable active agent. As also discussed further below, one especially preferred embodiment of the invention is in delivery of EFAs, particularly DHA. The invention may also be employed for EPA. In one instance, a composition of the invention may comprise both DHA and EPA. In a further especially preferred embodiment of the invention where a composition comprises one or more EFA it will also comprise one or more carotenoid.

Essential Fatty Acids (EFAs) as an agent to be delivered

In one preferred instance, the active agent is an essential fatty acid (EFA) and especially an omega 3, 6 or 7 fatty acid, in particular an omega 3 fatty acid. One especially preferred source of EFAs employed in the invention is DHA. In one instance a SFA, SCFA, and/or MCFA may be used to promote the delivery of an EFA, particularly DHA. In one instance a SFA is used to promote bioavailability of such an EFA. In another an SFA may be used to promote delivery via the portal vein and hence the liver.

The amount of EFA in a composition provided may be, for instance, by weight from 5 to 95%, for example from 10 to 80%, such as from 10 to 70%. It may, for instance, be from 20 to 70%. It may be, for example, from 25 to 75%. In some instances it may be from 30 to 80%. It may be, for instance, at least any of those point values. It may be up to any of those point values.

Thus, the invention may be employed as a way of increasing the bioavailability of EFAs such as omega 3. That is important as, for instance, it is estimated that with conventional omega 3 supplements some individuals may need to consume as much as 4 grams of omega 3 oil to receive an effective amount. As omega 3 oils are often extracted from fish with the associated taste, consuming so much omega 3 oils can be unpleasant and lead to non-compliance in many individuals. It may also give rise to side-effects. By increasing the bioavailability of EFAs such as omega 3, the amount of EFA which has to be consumed to achieve the same level of EFA in the circulation drops, meaning the chance of compliance is likely to be increased and there may also be decreased side-effects. Hence, increasing bioavailability of EFAs, such as omega 3 fatty acids, has potentially very large benefits.

Amongst the things that the present invention provides include:

A SFA for use in a method of increasing the bioavailability of an EFA, in particular omega 3 fatty acids, where the SFA and EFA are administered together in the same composition.

A SFA for use in a method of targeting an EFA, such as an omega 3 fatty acid, to, or via, the portal vein and liver, where the SFA and EFA are administered together in the same composition.

A composition comprising an SFA and an EFA, particularly an omega 3 fatty acid.

An EFA, particularly an omega 3 fatty acid, for use in a method of treating any of the conditions referred to herein and in particular any of those referred to below in relation to EFAs, particularly omega 3 fatty acids, where the EFA is administered in a composition that also comprises an SFA. In a further preferred embodiment of the invention, a composition of the invention may comprise an essential fatty acid and in particular an omega 3 fatty acid and an SFA.

A composition comprising SFA and EFA for use in a method of lowering serum cholesterol, triglyceride and/or LDL levels. In a preferred instance, the EFA is an omega 3 fatty acid. In a further preferred instance, the marker lowered is serum triglyceride levels. In another instance the ratio of LDL:HDL is lowered. Such targeting to the liver is important because that is where LDL is formed.

In further especially preferred instances of the above, a carotenoid will be present in any of the above compositions. As explained elsewhere herein particularly preferred compositions of the invention comprise a carotenoid or carotenoids and EFA.

In further preferred instances, SCFA may be employed instead of SFA or in combination with SFA in any of the compositions or uses discussed above. In another preferred instance, MCFA may be used instead of SCFA or in combination with it. Hence, one two or three of SFA, SCFA and MCFA may be present in the composition.

As well as targeting to the liver, the ability of the invention to allow for bypassing the liver is also important. For instance, there are embodiments where rather than target the liver, it is more important to promote the levels of EFA at the peripheral tissues, for example to promote cognition, CNS development, eye function, skin function or any of the other conditions discussed herein. Hence, by selecting to use MUFA, PUFA and/or LCFA to give rise to targeting to the peripheral tissues agents such as EFA may be delivered preferentially to those. Hence, the present invention also provides for:

A composition comprising an MUFA, PUFA and/or LCFA, together with an EFA, particularly an omega 3 fatty acid. In a preferred instance, MUFA and/or PUFA is employed. In a particularly preferred instance PUFA is employed.

Such a composition for use in targeting the EFA to the peripheral tissues or for promoting targeting of EFA to such tissues.

Such a composition for use in enhancing or promoting cognition, CNS development, eye function or skin function.

In any of the above embodiments, the composition may be as defined elsewhere herein, for instance in terms of the amount, or identity, of the SFA, SCFA, MCFA, MUFA, PUFA and/or LCFA or other agents present in the composition and the disease to be treated. In one especially preferred instance, the agent to be delivered present in a composition of the invention may be an omega-3 polyunsaturated fatty acid. Omega-3 polyunsaturated fatty acids are a typically considered to be a family of long-chain polyunsaturated fatty acids, generally C16-C24, in particular those having a C20-C22 chain, that have in common a carbon-carbon double bond in the n-3 position, i.e. the third bond from the methyl end of the fatty acid. In one preferred instance an omega 3 fatty acid may be employed with an SFA, SCFA and/or MCFA as described herein and particularly with a SFA. In an alternative instance, a composition of the invention may comprise a MUFA, PUFA and/or LCFA as described elsewhere herein, particularly a MUFA and/or PUFA and especially a PUFA. In instances where a composition employed in the invention comprises a SFA, SCFA and/or MCFA, particularly SFA, as well as an omega 3 fatty acid amongst other benefits, unexpectedly such compositions can have a positive effect on lipid levels, such as the level of cholesterol, triglycerides and/or LDL. The compositions may, for instance, lower the ratio of LDL:HDL. That is unexpected, particularly where SFA is employed, given that SFAs would be considered, if anything, likely to increase levels of cholesterol, triglycerides and/or LDL. Hence, counterintuitively, compositions comprising SFA and omega 3 fatty acids can have a positive effect on lipid levels. As indicated above, a SCFA and/or LCFA may be employed in place of the SFA or in combination with it. In an especially preferred embodiment of the invention, a composition of the invention is used in a method of lowering serum triglyceride levels. In a particularly preferred instance, the composition will comprise both one or more EFA and one or more carotenoid, as well as the specified fats.

Examples of omega 3 oils include HTA, ALA, SDA, ETE, ETA, EPA, HPA, DPA, DHA, tetracosapentaenoic acid and tetracosapentaenoic acid, any of which may be employed in the present invention. In one preferred instance, a composition of the invention may comprise the oils ALA (alpha-linolenic acid), EPA (eicosapentaenoic acid) and/or DHA (docosahexaenoic acid) and in particular EPA and/or DHA. In one preferred instance, a composition of the invention may comprise EPA. In a further preferred embodiment, a composition of the invention may comprise DHA. In another preferred embodiment a composition may comprise both EPA and DHA. DHA is particularly a preferred agent to be employed and DHA from any of the sources mentioned herein, particularly from fish or algae and in particular from algae may be employed. Employing algae has lower environmental impact compared to employing fish oils and so is a preferred embodiment of the invention. In one preferred instance, a composition may comprise an EFA, particularly an omega 3 fatty acid, a carotenoid, and SFA. In a preferred instance the omega 3 oil is DHA.

In one preferred instance, sources of omega 3 oils for use in the invention may include synthetic or natural origin like fatty fish, flaxseed oil, walnut oil or marine plankton. In one instance, a composition of the invention may comprise a plant oil comprising ALA, or an oil comprising DHA and/or EPA from marine oils, such as those from marine algae or phytoplankton. Other sources of omega oils include walnut, edible seeds, clary sage oil, algal oil, flaxseed oil, sacha inchi oil, echium oil and hemp oil and such oils may be employed in compositions of the invention, particularly as sources of oils comprising ALA. Sources of DHA include fish oils, egg oils, squid oils and krill oil. In one preferred instance, sources of EPA and DHA which may be used in the invention, include, but are not limited to, fish, calamari, caviar, hill, seal, green shell/lipped mussels, oysters, herring, anchovy, cod, salmon, sardine, prawns, red meat, turkey, algae, eggs and oils and/or extracts derived from these sources. Synthetic omega-3 fatty acids also exist and may be employed.

Compositions comprising EFAs, such as omega 3 fatty acids, may be used to treat any of the conditions mentioned herein, with examples of preferred conditions including heart disease, hypertension, diabetes, obesity, premature aging and cancer. In a further preferred instance of the invention, compositions comprising EFAs, such as omega 3, may be used to help treat or prevent age related memory loss and cognitive impairment, for instance they may be used to treat or prevent Alzheimer's or Parkinson's, particularly Alzheimer's. Such compositions may be, in a further embodiment, used to treat conditions such as bipolar disorder, depression and/or suicidal tendencies. In a further preferred instance, the condition to be treated or prevented may be one selected from atherosclerosis, angina, heart attack, congestive heart failure, arrhythmias, stroke and peripheral vascular disease. A composition as described herein, particularly one comprising EFA, preferably omega 3 fatty acids, may be used to treat or prevent blood clotting or high blood pressure, and in some instances may be used to maintain the elasticity of artery walls. In a further preferred instance, a composition of the invention, particularly one comprising EFAs such as omega 3, may be used in treating or preventing an inflammatory condition, such as an inflammatory bowel disorder and in particular ulcerative colitis. In a further preferred instance, a composition of the invention, particularly one comprising an EFA such as omega 3, may be used to help lower cholesterol, LDL and/or triglyceride. Such a composition of the invention may be used to lower the ratio of LDL:HDL. In other instances of the invention, a composition of the invention, particularly one comprising an EFA such as omega 3 fatty acids, may be used in the treatment or prevention of ADHD.

In one preferred instance, the composition of the invention may be used to treat a condition selected from asthma, autoimmune disease, heart disease, Type II diabetes, cancer, obesity, irritable bowel syndrome, and macular degeneration. In a further preferred embodiment of the invention, a composition of the invention may be used to treat arthritis, particularly rheumatoid arthritis or osteoarthritis and in particular rheumatoid arthritis. In a further preferred embodiment, a composition of the invention, particularly one comprising an omega 3 oil, may be used to treat a condition selected from a circulatory disease, cardiovascular diseases, hypertension, angina, anxiety disorders, neurosis disorders, panic disorders, brain hemorrhage, cerebrovascular disease, cardiac failure, cerebral vasospasm, coronary heart disease, thrombosis, myocardial ischemia, myocardial infarction, arrhythmia, and related diseases, an asthmatic condition, chronic pulmonary obstructive disease, an arthritis condition or other inflammatory condition.

Given that some essential fatty acids, such as omega 3 fatty acids, are PUFAs and/or MUFAs, they may be used as a PUFA and/or a MUFA in a composition of the invention intended to promote delivery which bypasses the liver. However, in an especially preferred instance, the EFA, such as omega 3, is provided in a composition of the invention with a SFA to promote delivery to, or at least via the liver. That may, for instance, increase bioavailability of the omega 3 fatty acid boosting the advantages of the omega 3 fatty acids. In a further particularly preferred instance, a composition of the invention may comprise DHA and a carotenoid, for instance DHA and any of those mentioned herein, such as DHA and lutein.

The present invention also provides a composition comprising one or more Essential Fatty Acid (EFA) and at least 5% of saturated fatty acids (SFA) and/or short chain fatty acids (SCFA) and/or medium chain fatty acids (MCFA). The invention further provides such a composition comprising as an Essential Fatty Acid omega 3 fatty acid or acids and at least 5% of saturated fatty acids (SFA) and/or short chain fatty acids (SCFA) and/or medium chain fatty acids (MCFA). In a particularly preferred instance, at least 5% SFA may be present.

In another preferred embodiment the present invention also provides a composition comprising: (i) one or more Essential Fatty Acids (EFA); (ii) cocoa butter; and (iii) at least one carotenoid. In a particularly preferred embodiment, the present invention provides a composition comprising one or more Essential Fatty Acids (EFA); (ii) cocoa butter; and (iii) at least one of lycopene, β- or α-carotene, lutein, meso-zeaxanthin, zeaxanthin, and/or astaxanthin. In one preferred instance, the composition comprises at least one of lutein, meso-zeaxanthin, zeaxanthin, and astaxanthin. In a further preferred embodiment, the composition comprises at least two of lutein, meso-zeaxanthin, and zeaxanthin. In a particularly preferred instance, all three of lutein, meso-zeaxanthin, and zeaxanthin are present in a composition of the invention. In a further particularly preferred embodiment, a composition of the invention comprises lycopene. Hence, one preferred composition of the invention comprises: (i) at least one EFA; (ii) at least 5% of saturated fatty acids (SFA) and/or short chain fatty acids (SCFA) and/or medium chain fatty acids (MCFA); and (iii) lycopene. In a preferred instance at least 5% SFA is present and in a more preferred instance it is provided by cocoa butter.

In an especially preferred embodiment, a composition of the invention comprises one or more Essential Fatty Acids (EFA); (ii) cocoa butter; and (iii) at least one of lycopene, β- or α-carotene, lutein, meso-zeaxanthin, zeaxanthin, and astaxanthin. In one preferred instance, at least two of lutein, meso-zeaxanthin, and zeaxanthin are present. In a particularly preferred instance, lutein, meso-zeaxanthin and zeaxanthin are all present.

In one embodiment, a composition of the invention may comprise, for instance from 10 to 2500 mg of EFA. In a further embodiment, a composition may comprise from 50 to 750 mg of EFA. In a preferred embodiment, a composition of the invention may comprise from 100 to 400 mg of EFA. In one preferred embodiment, a composition may comprise from 200 to 300 mg of EFA, for instance about 250 mg of EFA. In another preferred embodiment, a composition of the invention may comprise from 50 to 200 mg of EFA. In another embodiment, it may comprise from 100 to 200 mg of EFA, for instance about 125 mg of EFA. In one especially preferred instance, a composition of the invention may comprise EFA in an amount less than 1000 mg. For instance, less than 750 mg of EFA may be present. For example, less than 500 mg of EFA may be present, such as less than 300 mg of EFA. In one instance, less than 200 mg of EFA are present. In any of those embodiments, it may be that the composition comprises a lower limit of EFA of at least 25 mg, for instance at least 50 mg of EFA. In one instance, at least 100 mg of EFA are present. In an especially preferred instance, the EFA will be DHA and/or EPA, for instance both may be present. In one preferred instance DHA is present. For instance, in a particularly preferred instance the EFA may be omega-3. In one especially preferred instance, a composition of the invention may comprise any of the amounts recited herein for EFA as such an amount of DHA.

In a preferred instance, a composition of the invention comprising an EFA will also comprise a carotenoid, such as any of those specified herein. In a particularly preferred instance, the carotenoid will be selected from lycopene, β- or α-carotene, lutein, meso-zeaxanthin, zeaxanthin, and/or astaxanthin, particularly from lycopene, lutein, meso-zeaxanthin and zeaxanthin. In one especially preferred instance, the composition will comprise one or more of lutein, meso-zeaxanthin and zeaxanthin. In a particularly preferred instance, a composition of the invention may comprise at least two of lutein, meso-zeaxanthin and zeaxanthin and preferably all three. In one preferred instance, a composition of the invention comprise a xanthophyll.

In one preferred instance of the invention, a composition of the invention may comprise EFA, lutein, meso-zeaxanthin and zeaxanthin. In one preferred instance a composition of the invention may comprise from 25 to 750 mg EFA, from 0.1 to 20 mg lutein, from 0.1 to 20 mg meso-zeaxanthin, and from 0.1 to 20 mg zeaxanthin. For instance, in one case a composition of the invention may comprise from 50 to 500 mg EFA, from 0.1 to 50 mg lutein, from 0.1 to 50 mg meso-zeaxanthin, and from 0.01 to 35 mg zeaxanthin. Such a composition may, for instance, comprise from 100 to 300 mg EFA, from 0.5 to 10 mg lutein, from 0.5 to 10 mg meso-zeaxanthin, and from 0.25 to 5 mg zeaxanthin. In one preferred instance, a composition of the invention may comprise from 150 to 400 mg EFA, from 0.1 to 20 mg lutein, from 0.1 to 20 mg meso-zeaxanthin, and from 0.05 to 5 mg zeaxanthin. For instance, a composition may comprise from 200 to 300 mg EFA, from 0.5 to 20 mg lutein, from 0.5 to 20 mg meso-zeaxanthin, and from 0.1 to 10 mg zeaxanthin. In another embodiment of the invention, a composition may comprise from 75 to 200 mg EFA, from 0.1 to 20 mg lutein, from 0.1 to 20 mg meso-zeaxanthin, and from 0.05 to 5 mg zeaxanthin. For instance, a composition of the invention may comprise 75 to 200 mg EFA, from 0.5 to 10 mg lutein, from 0.5 to 10 mg meso-zeaxanthin, and from 0.25 to 5 mg zeaxanthin. In a particularly preferred instance in such compositions the EFA is an omega 3, for instance, it may be DHA or EPA. In an especially preferred instance, the composition comprises DHA, for instance in the amounts recited above for the EFA. In a further embodiment, the composition comprises SFA and/or SCFA and/or MCFA, particularly SFA as described elsewhere herein. Hence, any of the amounts of SFA and/or SCFA and/or MCFA described herein may be present. In one preferred instance at least 5% is present. In a particularly preferred instance, at least 10% of SFA is present. In a particularly preferred embodiment such amounts of SFA are present. An especially preferred source of SFA is cocoa butter.

In some instances a composition of the invention may comprise by weight from 10 to 50% EFA, from 0.05% to 10% lutein, from 0.05% to 10% meso-zeaxanthin, and from 0.01% to 5% zeaxanthin. In some instance, a composition may comprise from 20 to 50% EFA, from 0.05% to 5% lutein, from 0.05% to 5% meso-zeaxanthin, and from 0.025% to 1% zeaxanthin. For example, a composition may comprise from 5 to 30% EFA, from 0.05% to 5% lutein, from 0.05% to 5% meso-zeaxanthin, and from 0.025% to 1% zeaxanthin. For instance, a composition may comprise from 10 to 20% EFA, from 0.05% to 2.5% lutein, from 0.05% to 2.5% meso-zeaxanthin, and from 0.025% to 5% zeaxanthin. In some instances, a composition of the invention may comprise the ratio by weight of EFA:lutein:meso-zeaxanthin:zeaxanthin of from 50 to 250:from 0.25 to 20:from 0.25 to 20:from 0.5 to 1.5. For instance, the ratio may be from 50 to 200:from 0.5 to 15:from 0.5 to 15:1. The EFA may be any mentioned herein. In one preferred instance, the EFA is omega3, particularly DHA and/or EPA, preferably DHA. In a further embodiment, the composition comprises saturated fatty acids (SFA) and/or short chain fatty acids (SCFA) and/or medium chain fatty acids (MCFA), particularly SFA as described elsewhere herein. An especially preferred source of EFA is cocoa butter. In one preferred instance, a composition of the invention may further comprise saturated fatty acids (SFA) and/or short chain fatty acids (SCFA) and/or medium chain fatty acids (MCFA) as set out herein and in particular an SFA. In a particularly preferred instance the SFA will be provided by the composition comprising cocoa butter.

Further examples of preferred compositions of the invention comprising EFA, lutein, meso-zeaxanthin, zeaxanthin, and cocoa butter include those comprising, for instance from 25 to 2500 mg EFA, from 0.05 to 50 mg lutein, from 0.05 to 50 mg meso-zeaxanthin, from 0.05 to 50 mg zeaxanthin and from 50 to 2500 mg cocoa butter. For instance, a preferred composition comprises 25 to 1000 mg EFA, from 0.1 to 25 mg lutein, from 0.1 to 25 mg meso-zeaxanthin, from 0.05 to 10 mg zeaxanthin and from 50 to 750 mg cocoa butter. One example of a preferred composition comprises 25 to 1000 mg EFA, from 0.5 to 25 mg lutein, from 0.5 to 25 mg meso-zeaxanthin, from 0.05 to 10 mg zeaxanthin and from 50 to 750 mg cocoa butter. In another preferred instance, a composition of the invention comprises 50 to 175 mg EFA, from 0.5 to 10 mg lutein, from 0.5 to 10 mg meso-zeaxanthin, from 0.25 to 3 mg zeaxanthin and from 200 to 600 mg cocoa butter. In another preferred instance, a composition of the invention comprises 150 to 300 mg EFA, from 0.11 to 10 mg lutein, from 0.1 to 10 mg meso-zeaxanthin, from 0.25 to 3 mg zeaxanthin and from 50 to 150 mg cocoa butter. In one preferred embodiment of the invention, a composition will comprise about equal amounts of lutein and meso-zeaxanthin. In one preferred instance, the amount of lutein and/or meso-zeaxanthin will be greater than the amount of zeaxanthin. For instance, the amount of lutein may be from two to ten times greater than that of zeaxanthin. For instance, it may be from two to five times greater. That may also be the case for the amount of meso-zeaxanthin compared to the amount of zeaxanthin.

Examples of further preferred formulations are indicated in Table A below. Examples of preferred compositions include compositions comprising the indicated constituents within ±50% of the indicated values. For instance, a composition provided may have within ±40% of the indicated values. It may have within ±30% of the indicated values. It may have ±20% of the indicated values. It may have within ±10%. That may be just the case for the indicated weight values. It may be just the case for the indicated % weight values. It may be just the case for the indicated ratios. In one embodiment, it may be the case for at least two of those or all three.

TABLE A

| | FORMULATION 1 | | |
|---|---|---|---|
| | DHA | Lycopene | Cocoa butter |
| weight/mg | 250 mg | 7 mg | 88 mg |
| % weight | 33% | 0.9% | 12% |
| ratio | 36 | 1 | 13 |

| | DHA | Lutein | Meso-zeaxanthin | zeaxanthin | Cocoa butter |
|---|---|---|---|---|---|
| | | | FORMULATION 2 | | |
| weight/mg | 250 mg | 3.5 mg | 3.5 mg | 1.4 mg | 93 mg |
| % weight | 33% | 0.5% | 0.5% | 0.2% | 12% |
| ratio | 180 | 2.5 | 2.5 | 1 | 66.4 |
| | | | FORMULATION 3 | | |
| weight/mg | 125 mg | 3.5 mg | 3.5 mg | 1.4 mg | 405.5 mg |
| % weight | 16% | 0.5% | 0.5% | 0.2% | 53% |
| ratio | 90 | 2.5 | 2.5 | 1 | 290 |

Typically where an amount is indicated for a carotenoid that is the actual amount of the carotenoid indicated, not the overall amount of the oil containing it.

In one preferred instance, compositions of the invention comprising EFAs, may be for use in a method of:
(a) increasing serum concentration of one or more Essential Fatty Acids, preferably wherein serum concentrations of DHA and/or EPA are increased, more preferably both;
(b) increasing serum concentration of omega 3;
(c) decreasing serum lipids, preferably decreasing triglyceride and/or LDL cholesterol levels, more preferably serum triglyceride levels;
(d) decreasing inflammatory oxidative damage; or
(e) decreasing LDL oxidation.

In one especially preferred embodiment of the invention a composition of the invention is employed to increase serum levels of one or more EFA. In a particularly preferred embodiment of the invention, a composition comprising one or more EFA, one or more carotenoid and a SFA, SCFA and or MCFA as set out herein is employed for such a purpose. In one preferred instance, a composition of the invention comprising one or more EFA, one or more carotenoid selected from lycopene, lutein, meso-zeaxanthin and zeaxanthin and cocoa butter is employed. In one preferred instance, at least two of lutein, meso-zeaxanthin and zeaxanthin are present and preferably all three. In a particularly preferred instance, a composition comprising DHA, cocoa butter, lutein, meso-zeaxanthin and zeaxanthin is employed for such a purpose, such as any such composition recited herein. In a preferred instance, serum DHA concentration is raised, preferably compared to administration of the same amount of DHA alone. Compositions of the invention may also be used to raise levels of serum EPA. In some instance, both levels of serum DHA and EPA are raised compared to a control. In preferred instance, the increase seen may be, for instance at least 2, 5, 10, 20, or 50 times greater than the increase seen with a control subject administered the EFA alone, or a range comprising any two of those values as end points. For instance, a rise of at least 5 times compared to the control may be seen. For example a rise of at least 10 times may be seen compared to the control. In some case a rise of at least 25 times may be seen compared to the rise with the control. The rise in serum concentrations may be as measure, for instance, at around four weeks after consumption.

In another embodiment, a composition of the invention is use to lower serum lipid levels. In an especially preferred embodiment of the invention, a composition of the invention is used to lower serum lipid levels, particularly serum triglyceride levels. Particularly preferred compositions for such a use include a composition of the invention comprising EFA, one or more carotenoids, and cocoa butter, particularly a composition comprising EFA, cocoa butter, and one or more carotenoids selected from lycopene, β- or α-carotene, lutein, meso-zeaxanthin, zeaxanthin, and/or astaxanthin. In a preferred embodiment at least one of lycopene, lutein, meso-zeaxanthin and zeaxanthin is present. In a preferred embodiment at least two of lutein, meso-zeaxanthin and zeaxanthin are present and preferably all three. It may be, for instance, that the decrease seen with a composition of the invention is at least 10%, 25%, 50% or 100% bigger than the decrease seen with a control subject just administered the EFA alone, that may be, for instance the case for triglyceride levels and/or LDL cholesterol levels, particularly for triglyceride levels, preferably for both. Such increases may alternatively or additionally, also be seen for the level of inflammatory oxidative damage (IOD). They may also be seen for measurement of other inflammatory markers, such as levels of LDL-Px.

As described further above and below, in a number of particularly preferred embodiments, compositions comprising Essential Fatty Acids and carotenoids are employed to help influence further where delivery occurs to. Hence, in a particularly preferred instance, a composition of the invention comprises both one or more EFA and one or more carotenoids. Various preferred instances of such compositions are described below.

In an especially preferred embodiment of the invention, where a composition of the invention comprises EFA it comprises an omega-3 fatty acid. In one particularly preferred embodiment of the invention, a composition of the invention comprising one or more EFA may be employed to increase serum concentration of the one or more EFA.

In preferred embodiments of the invention, it may be that a composition of the invention comprises from 20 to 750 mg of EFA. For instance, it may be that a composition of the invention may comprise from 25 to 400 mg of EFA. In one instance, a composition may comprise from 50 to 300 mg of EFA. In one instance, a composition of the invention may comprise from 100 to 300 mg of EFA. In some instances, about 125 mg or about 250 mg may be present in a composition of the invention. Such doses of EFA may be provided, for instance, for a composition of the invention comprising one or more EFAs and one or more carotenoids. Such amounts of SFA may be the case for any of the EFAs set out herein, particularly though omega3. In one particularly preferred embodiment, a composition of the invention may comprise such amounts of DHA.

Polyphenols as an Active Agent to be Delivered

In one particularly preferred instance, a composition of the invention may comprise a polyphenol. In one instance, a preferred polyphenol to be employed is a compound exclusively derived from the shikimate/phenylpropanoid and/or the polyketide pathway, featuring more than one phenolic unit and deprived of nitrogen-based functions. In a particularly preferred instance a polyphenol employed in the invention is one which has anti-oxidant activity. In one preferred instance, a polyphenol employed may be a naturally occurring polyphenol. In an alternative preferred instance a polyphenol employed may be a synthetic polyphenol. Hence, the invention may be employed to increase bioavailability of the polyphenol. The invention may be used to target a polyphenol or polyphenols to, or via, the liver. The levels of increased bioavailability and/or targeting may be any of those discussed herein. The relative amount of agent and SFA, SCFA, MUFA, PUFA and/or LCFA may be, for instance, any of the amounts referred to herein.

Examples of polyphenols which may be employed include, for instance, at least one of resveratrol, an anthocyanins, an anthocyanidin, and a catechins. One especially preferred polyphenol is resveratrol. Further preferred polyphenols include in particular catechins. Further examples of phenols which may be employed include polyphenols from artichoke, chlorogenic acid (for instance that extracted from the coffee plant), curcumin (for instance that extracted from the curcumin plant), daidzein (for instance as extracted from soy), catechins and epicatechins (for instance extracted from cocoa, berries, or baobab fruit), epigallocatechin-3-gallate (for instance as extracted from green tea), genistein (for instance as extracted from soy), ginsenoside (for instance as extracted from ginseng), phenethyl isothiocynate (for instance as extracted from plants such as broccoli, cabbage, Brussel sprouts, or cauliflower), pterostilbene (for instance as extracted from blueberries), sulforaphane (for instance as obtained from broccoli, cabbage or kale), quercetin (for instance as extracted from onions, buckwheat or citrus), resveratrol (for instance as extracted from red grapes, aronia, bilberries, blueberries, cranberries, barberries, cherries, sea buckthorn, or nuts), anthocyanins and anthocyanidins (for instance extracted from aubergine, berries), and lycopene (for instance as extracted from tomatoes). A further preferred polyphenol for use in the present invention is pycnogenol. Pycnogenol is extracted from the tree *Pinus pinaster*. Similar polyphenol preparations may also be generated from peanut skin, grapeseed and witch hazel bark and polyphenol from *Pinus pinaster* or the other sources may be employed. In one preferred instance therefore, any of the compositions discussed therein may comprise Pycnogenol.

In one preferred instance, the composition of the invention may be used to treat cancer, particularly where a polyphenol is employed, for instance where one of the polyphenols mentioned in this section and preferably paragraph is employed. Examples of cancers include hepatocellular carcinoma, breast cancer, lung cancer, pancreatic cancer, prostate cancer, lung cancer, skin cancer, esophageal cell carcinoma, renal cancer, glioma, colorectal cancer, pancreatic cancer or oral cancer. In one particularly preferred instance the cancer to be treated via the present invention is breast cancer or prostate cancer and even more preferably is prostate cancer.

In one preferred instance a polyphenol is employed to help treat a brain disorder and/or a neurodegenerative disorder, for instance Alzheimer's or Parkinson's or other types of cognitive impairments. Further disorders that the administration of polyphenols via the invention may be relevant to include stroke, multiple sclerosis, and Huntington's disease. In a further preferred instance, the condition to be treated or prevented is dementia. In one particularly preferred instance the polyphenol employed to treat such conditions may be any of the specific polyphenols named herein and in particular be a green or white tea polyphenol, particularly a green tea polyphenol. In a further instance the polyphenol employed to treat or prevent such conditions may be a curcumin. In a further preferred instance, the polyphenol, particularly where used to treat a neurodegenerative disorder, may be one selected from resveratrol, Baicalein, Kaempferol, acacetin, apigenin, luteolin, a soybean isoflavone, fisetin, silymarin, pterostilbene, epicatechin, xanthohumol, flavone glycoside, and quercetin.

In further preferred embodiments of the invention a polyphenol is employed, such as any named herein. Compositions of the invention, particularly those comprising polyphenols, may be used, for instance to treat a condition selected from arteriosclerosis, hypertension, pulmonary hypertension, coronary artery disease, chronic heart failure, peripheral artery disease, diabetes, chronic renal failure, retina and macular degeneration or dysfunctions and erectile dysfunction. In one preferred instance, the polyphenol in such embodiments is proanthocyanidin and/or ellagitannin and preferably both. In a further preferred instance, a polyphenol, for instance such as any of those specified herein, may be used to treat to inflammation or inflammatory damage, for instance inflammatory oxidative damage. In a further instance, the condition to be treated via employing a polyphenol may be arthritis. In a further preferred instance, the condition to be treated by employing the polyphenol is atherosclerosis.

A particularly preferred polyphenol which may be present in a composition of the invention is a trans-resveratrol. Further examples of polyphenols include capsaicin, thymol, cinnamic acid and rosmarinic acid and any of those polyphenols may be employed in compositions of the invention. Additional examples of polyphenols include tannins such as, for instance, tannic acid and ellagitannin.

The present invention also provides a composition comprising SFA, SCFA and/or MCFA, particularly SFA, and a polyphenol, particularly where the polyphenol is trans-resveratrol. The SFA, SCFA and/or MCFA, the amount of SFA, SCFA and/or MCFA, and the other parameters of such a composition may be, for instance, as defined anywhere herein for compositions of the invention. The present invention also provides for the use of a SFA, SCFA and/or MCFA, particularly SFA, for increasing the bioavailability of a polyphenol, particularly a trans-resveratrol. The present invention further provides for a method of targeting trans-resveratrol to, or via, the liver comprising administering a composition of the invention comprising SFA SCFA, and/or MCFA, particularly SFA, and tRV. In a preferred instance, bioavailability is assessed by measuring the amount of trans-resveratrol in the serum. It may be, for instance, that the serum level of a polyphenol, in particular tRV, may be increased at least two, three, four, five, ten or more fold compared to the level seen when the tRV is taken orally on its own.

In one preferred embodiment, the polyphenol is a catechin. The invention provides SFA, SCFA, and/or MCFA, particularly SFA, for use in increasing the bioavailability of catechin, by administering a composition comprising SFA, SCFA, and/or MCFA, particularly SFA and the catechin orally. The invention also provides a way of increasing the targeting of catechin to, or via, the liver following oral administrating, comprising administering a composition comprising a catechin and SFA, SCFA, and/or MCFA, particularly SFA. In one preferred embodiment, increase in bioavailability may be measured in terms of serum concentrations of catechin. In one preferred instance, the catechin is an epicatechin, or the compound measured in the serum to determine bioavailability is/are an epicatechin(s), particularly those measured in the Examples of the present application.

In one preferred instance, a composition of the invention may comprise from 1 to 1000 µg of polyphenol. For instance, a composition of the invention may comprise from 5 to 700 µg of polyphenol. It may be that, for instance, a composition of the invention comprises from 100 to 500 µg of polyphenol. In one preferred instance, the amount of polyphenol may be from 25 to 75 µg of polyphenol. In one preferred instance, a composition of the invention may comprise from 20 to 40 of µg polyphenol. In a further preferred instance, a composition of the invention may comprise about 30 µg of polyphenol. In an especially preferred embodiment of the invention, a composition may comprise such amounts of tRV. Hence, any of the compositions of the invention as set out herein may comprise such amounts of tRV. In other instances the polyphenol may comprise catechin, for instance it may comprise from 50 to 2000 µg of catechin. For example, it may comprise from 100 to 1000 µg of catechin. For instance, it may comprise from 200 to 600 µg of catechin. In one preferred instance, a composition may comprise about 400 µg of catechin.

In one especially preferred embodiment of the invention, a composition of the invention comprising a polyphenol is employed to increase the serum level of the polyphenol compared to the level seen with a control administered the same amount of polyphenol on its own. In a preferred embodiment of the invention, a composition of the invention comprising one or more polyphenols, SFA, SCFA and/or MCFA as described herein is so employed. For instance, in a preferred instance, the composition comprises SFA as set out herein. In one preferred instance, a composition comprising cocoa butter and a polyphenol is provided. In one preferred instance the composition comprises cocoa butter and tRV.

In another preferred instance the composition comprises cocoa butter and polyphenol. It may be, for instance, that the composition comprises from 100 mg to 2500 mg of cocoa butter, such as from 100 to 1000 mg of cocoa butter, preferably from 200 to 600 mg of cocoa butter, as well as the recited amounts of polyphenol set out above, for instance for tRV or catechin.

In one instance, a composition of the invention comprising catechin may following oral consumption show a serum concentration of epicatechin sulphate that is at least 25%, 50%, 75% or 100% bigger than the serum concentration seen with administration of a control composition comprising the catechin, but instead comprising MUFA, PUFA and/or LCFA as recited herein, particularly PUFA. The serum concentration compared to such a control may be, for instance at least double. It may be, for instance at least 5 times greater. In some cases it may be at least 10 times greater, such as at least 20 times greater. The serum concentration of O-methylepicatechin may also, or alternatively, show such an increase. Such increases may be seen at, for instance, one hour after oral consumption of the composition. In another instance, a composition of the invention comprising SFA, SCFA and/or MCFA, particularly SFA, as set out herein and tRV may result in a serum concentration of tRV be at least 5, 10, 20 or 50 fold greater than consumption of tRV on its own. An increase compared to an equivalent composition except it comprises PUFA may be, for instance, at least 2, 3, 4, 5 or 6 fold greater, such as at least 10 fold greater. In one instance, the increase is from 5 to 15 fold. For instance, the increase may be from 7 to 10 fold.

Carotenoids as an Active Agent to be Delivered

In one particularly preferred embodiment of the invention, a composition of the invention may comprise a carotenoid or carotenoids. Carotenoid compounds are a class of tetraterpenoids which contain long polyene chains. Carotenoids include xanthophylls such as lutein, meso-zeaxanthin, zeaxanthin and astaxanthin, and carotenes, such as beta-carotene, alpha-carotene, zeta-carotene, and lycopene and related molecules, including 1-HO-3', 4'-didehydrolycopene, 3, 1'-(HO)2-gamma-carotene, 1,1'-(HO)2-3, 4, 3', 4'-tetradehydrolycopene, 1, 1'-(HO)2-3, 4-didehydrolycopene. In one particularly preferred embodiment, the carotenoid or carotenoids employed is a carotene or carotenes, particularly where an EFA is being delivered and preferably where delivery is to, or via, the liver. In another preferred embodiment, the carotenoid or carotenoids employed is one or more xanthophyll, particularly where an EFA is being delivered, preferably where delivery is intended to bypass the liver.

Other suitable carotenoid compounds which may be used as described herein include hydrocarbons, such as lycopersene (7,8,11,12,15,7',8',11',12',15'-decahydro-γ,γ-carotene), phytofluene, hexahydrolycopene (15-cis-7,8,11,12,7', 8'-hexahydro-γ,γ-carotene), torulene (3',4'-didehydro-β,γ-carotene) and α-zeacarotene (7',8'-dihydro-ε,γ-carotene); alcohols, such as alloxanthin, cynthiaxanthin, pectenoxanthin, cryptomonaxanthin, ((3r,3'r)-7,8,7',8'-tetradehydro-β, β-carotene-3,3'-diol), crustaxanthin (β-carotene-3,4,3',4'-tetrol), gazaniaxanthin ((3r)-5'-cis-β,γ-caroten-3-ol), oh-chlorobactene (1',2'-dihydro-f,γ-caroten-1'-ol), loroxathin ((β,ε-carotene-3,19,3'-triol), lycoxanthin (γ,γ-caroten-16-ol), rhodopin (1,2-dihydro-γ,γ-caroten-1-ol), rhodopinol (aka warrningol; 13-cis-1,2-dihydro-γ,γ-carotene-1,20-diol), saproxanthin (3',4'-didehydro-1',2'-dihydro-β,γ-carotene-3, 1'-diol) and zeaxanthin; glycosides, such as oscillaxanthin (2,2'-bis(β-1-rhamnopyranosyloxy)-3,4,3',4'-tetradehydro-1,2,1',2'-tetrahydro-γ,γ-carotene-1,1'-diol), and phleixanthophyll (1'-(β-d-glucopyranosyloxy)-3',4'-didehydro-1',2'-dihydro-β,γ-caroten-2'-ol); ethers, such as rhodovibrin (1'-methoxy-3',4'-didehydro-1,2,1',2'-tetrahydro-γ,γ-caroten-1-ol) and (1-methoxy-3,4-didehydro-1,2,7',8'-tetrahydro-γ,γ-carotene), epoxides, such as diadinoxanthin (5,6-epoxy-7', 8'-didehydro-5,6-dihydro-carotene-3,3-diol), luteoxanthin (5,6: 5',8'-diepoxy-5,6,5',8'-tetrahydro-β,β-carotene-3,3'-diol), mutatoxanthin, citroxanthin, zeaxanthin (furanoxide 5,8-epoxy-5,8-dihydro-β,β-carotene-3,3'-diol), neochrome, (5',8'-epoxy-6,7-didehydro-5,6,5',8'-tetrahydro-β,β-carotene-3,5,3'-triol), foliachrome, trollichrome, and vaucheriaxanthin (5',6'-epoxy-6,7-didehydro-5,6,5',6'-tetrahydro-β, β-carotene-3,5,19,3'-tetrol); aldehydes, such as rhodopinal, wamingone (13-cis-1-hydroxy-1,2-dihydro-γ,γ-caroten-20-al), torularhodinaldehyde (3',4'-didehydro-β,γ-caroten-16'-al); acids and acid esters, such as torularhodin (3',4'-didehydro-β,γ-caroten-16'-oic acid) and torularhodin methyl ester (methyl 3',4'-didehydro-β,γ-caroten-16'-oate); ketones, such as astaxanthin, canthaxanthin (aka aphanicin), chlorellaxanthin (β,β-carotene-4,4'-dione), capsanthin ((3r,3's, 5'r)-3,3'-dihydroxy-β,κ-caroten-6'-one), capsorubin ((3s,5r, 3's,5'r)-3,3'-dihydroxy-κ,κ-carotene-6,6'-dione), cryptocapsin ((3'r,5'r)-3'-hydroxy-β,κ-caroten-6'-one), 2,2'-diketospirilloxanthin (1,1'-dimethoxy-3,4,3',4'-tetradehydro-1,2,1',2'-tetrahydro-γ,γ-carotene-2,2'-dione), flexixanthin (3,1'-dihydroxy-3',4'-didehydro-1',2'-dihydro-β,γ-caroten-4-one), 3-oh-canthaxanthin (aka adonirubin; aka phoenicoxanthin; 3-hydroxy-β,β-carotene-4,4'-dione), hydroxyspheriodenone (1'-hydroxy-1-methoxy-3,4-didehydro-1,2,1',2',7',8'-hexahydro-γ,γ-caroten-2-one), okenone (1'-methoxy-1',2'-dihydro-c,γ-caroten-4'-one), pentenolone (3,3'-dihydroxy-7',8'-didehydro-β,β-caroten-4-one), phoeniconone (aka dehydroadonirubin; 3-hydroxy-2,3-didehydro-β,β-carotene-4,4'-dione), phoenicopterone (β,ε-caroten-4-one), rubixanthone (3-hydroxy-β,γ-caroten-4'-one), siphonaxanthin (3,19,3'-trihydroxy-7,8-dihydro-β,ε-caroten-8-one); esters of alcohols, such as astacein (3,3'-bispalmitoyloxy-2,3,2',3'-tetradehydro-β,β-carotene-4,4'-dione or 3,3'-dihydroxy-2,3,2',3'-tetradehydro-β,β-carotene-4,4'-dione dipalmitate), fucoxanthin (3'-acetoxy-5,6-epoxy-3,5'-dihydroxy-6',7'-didehydro-5,6,7,8,5',6'-hexahydro-β,β-caroten-8-one), isofucoxanthin (3'-acetoxy-3,5,5'-trihydroxy-6',7'-didehydro-5,8,5',6'-tetrahydro-β,β-caroten-8-one), physalien, zeaxanthin dipalmitate ((3r,3'r)-3,3'-bispalmitoyloxy-β,β-carotene or (3r,3'r)-β,β-carotene-3,3'-diol dipalmitate) and siphonein (3,3'-dihydroxy-19-lauroyloxy-7,8-dihydro-β,ε-caroten-8-one or 3,19,3'-trihydroxy-7,8-dihydro-β,ε-caroten-8-one 19-laurate); apo carotenoids, such as β-apo-2'-carotenal (3',4'-didehydro-2'-apo-b-caroten-2'-al), apo-2-lycopenal, apo-6'-lycopenal (6'-apo-y-caroten-6'-al), azafrinaldehyde (5,6-dihydroxy-5,6-dihydro-10'-apo-β-caroten-10'-al), bixin (6'-methyl hydrogen 9'-cis-6,6'-diapocarotene-6,6'-dioate), citranaxanthin (5',6'-dihydro-5'-apo-β-caroten-6'-one or 5',6'-dihydro-5'-apo-18'-nor-β-caroten-6'-one or 6'-methyl-6'-apo-β-caroten-6'-one), crocetin (8,8'-diapo-8,8'-carotenedioic acid), crocetinsemialdehyde (8'-oxo-8,8'-diapo-8-carotenoic acid), crocin (digentiobiosyl 8,8'-diapo-8,8'-carotenedioate), hopkinsiaxanthin (3-hydroxy-7,8-didehydro-7',8'-dihydro-7'-apo-b-carotene-4,8'-dione or 3-hydroxy-8'-methyl-7,8-didehydro-8'-apo-b-carotene-4,8'-dione), methyl apo-6',lycopenoate (methyl 6'-apo-y-caroten-6'-oate), (3,5-dihydroxy-6,7-didehydro-5,6,7',8'-tetrahydro-7'-apo-b-caroten-8'-one or 3,5-dihydroxy-8'-methyl-6,7-didehydro-5,6-dihydro-8'-apo-b-caroten-8'-one) and sintaxanthin (7',8'-dihydro-7'-apo-b-caroten-8'-one or 8'-methyl-8'-apo-b-caroten-8'-one); nor and seco carotenoids, such as (3,3'-bisacyloxy-2,2'-dinor-b,b-carotene-4,4'-dione), β-carotenone (5,6:5',6'-diseco-b,b-carotene-5,6,5',6'-tetrone), peridinin (3'-acetoxy-5,6-epoxy-3,5'-dihydroxy-6',7'-didehydro-5,6,5',6'-tetrahydro-12',13',20'-trinor-b,b-caroten-19,11-olide), pyrrhoxanthininol (5,6-epoxy-3,3'-dihydroxy-7',8'-didehydro-5,6-dihydro-12',13',20'-trinor-b,b-caroten-19,11-olide), semi-α-carotenone (5,6-seco-b,e-carotene-5,6-dione), semi-β-carotenone (5,6-seco-b,b-carotene-5,6-dione or 5',6'-seco-b,b-carotene-5',6'-dione) and triphasiaxanthin (3-hydroxysemi-b-carotenone 3'-hydroxy-5,6-seco-b,b-carotene-5,6-dione or 3-hydroxy-5',6'-seco-b,b-carotene-5',6'-dione); retro carotenoids and retro apo carotenoids, such as eschschoitzxanthin (4',5'-didehydro-4,5'-retro-b,b-carotene-3,3'-diol), eschscholtzxanthone (3'-hydroxy-4',5'-didehydro-4,5'-retro-b,b-caroten-3-one), rhodoxanthin (4',5'-didehydro-4,5'-retro-b,b-carotene-3,3'-dione) and tangeraxanthin (3-hydroxy-5'-methyl-4,5'-retro-5'-apo-b-caroten-5'-one or 3-hydroxy-4,5'-retro-5'-apo-b-caroten-5'-one); and higher carotenoids, such as nonaprenoxanthin (2-(4-hydroxy-3-methyl-2-butenyl)-7',8',11',12'-tetrahydro-e,y-carotene), decaprenoxanthin (2,2'-bis(4-hydroxy-3-methyl-2-butenyl)-e,e-carotene), c.p. 450 (2-[4-hydroxy-3-(hydroxymethyl)-2-butenyl]-2'-(3-methyl-2-butenyl)-b,b-carotene), c.p. 473 (2'-(4-hydroxy-3-methyl-2-butenyl)-2-(3-methyl-2-butenyl)-3',4'-didehydro-1',2'-dihydro-b,y-caroten-1'-ol) and bacteriorurberin (2,2'-bis(3-hydroxy-3-methylbutyl)-3,4,3',4'-tetradehydro-1,2,1',2'-tetrahydro-γ,γ-carotene-1,1'-diol).

One particularly preferred carotene is lycopene. In another preferred instance one or both of lutein, or zeaxanthin is employed. Hence, in one instance a composition of the invention comprises lutein. In another instance it comprises zeaxanthin. In a further instance it comprises both lutein and zeaxanthin. In a preferred embodiment of the invention, a composition may comprise at least two of lutein, meso-zeaxanthin and zeaxanthin. In an especially preferred embodiment of the invention, a composition may comprise all three of lutein, meso-zeaxanthin and zeaxanthin.

In one particularly preferred embodiment of the invention, the composition provided comprises one or more carotenoids selected from lycopene, β- or α-carotene, lutein, meso-zeaxanthin, zeaxanthin, and/or astaxanthin. In a particularly preferred embodiment the one or more carotenoid present is selected from lycopene, lutein, meso-zeaxanthin, and zeaxanthin. In a particularly preferred embodiment at least two of lutein, meso-zeaxanthin, and zeaxanthin are present. In an especially preferred embodiment all three of lutein, meso-zeaxanthin, and zeaxanthin are present.

In one preferred instance, a composition of the invention will comprise from 0.001% to 20% by weight of carotenoid. For instance, they may comprise 0.05% to 20% by weight of carotenoid. For instance, a composition may comprise from 0.1 to 10% by weight of carotenoid. In some instances, the amount of carotenoid may be from 0.1 to 5%, such as from 0.5% to 2.5% by weight of carotenoid. In some cases the weight of carotenoid may be from 0.1 to 30 mg. For instance, the amount by weight may be from 0.5 to 15 mg. In some cases it may be from 1 to 10 mg. In some cases, it may be from 5 to 15 mg. In some cases, from 0.01 to 50 mg may be present. For instance, it may be from 0.01 to 10% by weight is present in a composition of the invention. Such values may be for a particular carotenoid in the composition. Alternatively, all the overall carotenoid content in the composition may add up to such a value.

A SFA, SCFA, and/or MCFA, particularly SFA, is provided for use in increasing the delivery of a carotenoid to, or via the liver. In one preferred instance, the invention comprises a SFA, SCFA, and/or MCFA, particularly SFA, for use in a method of increasing the bioavailability of a carotenoid, where the method comprises oral consuming a composition comprising a carotenoid and SFA, SCFA, and/or MCFA, particularly SFA. Increased bioavailability may be reflected in increased levels of carotenoid in the serum, for instance compared to a control composition lacking whichever of the SFA, SCFA, and/or MCFA is present in the test composition.

A composition as described herein may contain a single carotenoid compound or more than one carotenoid compound. For instance, a composition as described herein may comprise, one, two, three, four, five, six or more carotenoids, such as any of those numbers of the specific carotenoids specified here. A composition may in one instance comprise one, two or three carotenoids, for instance any of the specific carotenoids specified herein. In one preferred instance, a composition may comprise one carotenoid, for example where the carotenoids is any of those specified herein. In one instance, each carotenoid may be, for instance, present in a range of different isomeric forms. In an especially preferred embodiment, all three of lutein, meso-zeaxanthin, and zeaxanthin may be present. That may be the case in particular where the composition comprises one or more essentially fatty acid. Compositions comprising both one or more carotenoid and one or more Essential Fatty Acids are especially preferred compositions of the invention.

In one particularly preferred embodiment the carotenoid compound is lycopene, hence in any of the embodiments described herein where a carotenoid is present, in a preferred instance the carotenoid is lycopene or where more than one carotenoid is present lycopene may be one of the carotenoids present. Lycopene is an open-chain unsaturated $C_{40}$ carotenoid of structure I (Chemical Abstracts Service Registry Number 502-65-8).

Structure I

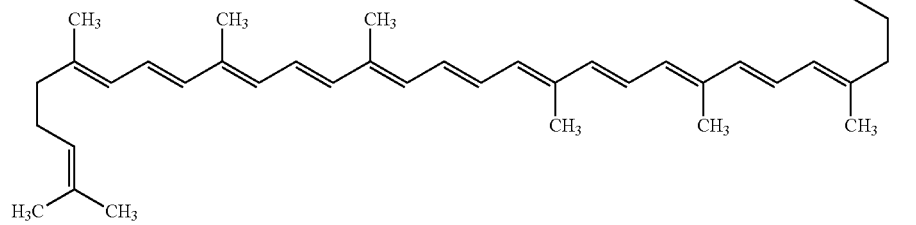

Lycopene occurs naturally in plants such as tomatoes, guava, rosehip, watermelon and pink grapefruit. Lycopene for use as described herein may, for instance comprise one or more different isomers. For example, lycopene may comprise at least 10%, at least 20%, at least 30%, at least 40%, at least 50%, at least 60%, at least 70%, at least 80%, at least 90%, or at least 95% (Z)-isomers, (all-E)-isomers, or cis-isomers, such as 5-cis- or 9-cis- or 13-cis-isomers, which have improved bioavailability relative to trans isomers. Trans isomers may isomerise into cis forms in vivo, or during storage and processing.

Carotenoid compounds for use as described herein may be natural i.e. obtained from a natural source, for example, extracted from a plant, such as a tomato or melon, particularly water melon. A range of methods for extracting, concentrating and/or purifying carotenoids from plants are known in the art. For example, solvent extraction using ethanol, DMSO, ethyl acetate, hexane, acetone, soya or other vegetable oil, or non-vegetable oils may be employed. A carotenoid compound may be isolated i.e. free or substantially free of other molecules found in its natural source or environment.

Carotenoid compounds for use as described herein may be synthetic i.e. produced by artificial means, for example, by chemical synthesis or fermentation. A range of methods for chemical synthesis of lycopene and other carotenoids are known in the art. For example, a three-stage chemical synthesis based on the standard Wittig olefination reaction scheme for carotenoid synthesis may be employed, in which an organic solution of $C_{15}$ phosphonium methanesulfonate in dichloromethane (DCM) and an organic solution of $C_{10}$ dialdehyde in toluene are produced, and the two organic solutions are gradually combined with sodium methoxide solution and undergo a condensation reaction to form crude lycopene. The crude lycopene may then be purified using routine techniques, for example by adding glacial acetic acid and deionized water to the mixture, stirring vigorously, allowing the aqueous and organic phases to separate, and extracting the organic phase containing DCM and crude lycopene with water. Methanol is added to the organic phase and the DCM removed via distillation under reduced pressure. The crude methanolic lycopene solution is then be heated and cooled to crystalline slurry that is filtered and washed with methanol. The lycopene crystals may then be recrystalized and dried under heated nitrogen. Synthetic carotenoids, such as lycopene, are also available from commercial suppliers (e.g. BASF Corp, NJ USA, DSM Nutritional Products, Basel, CH).

Synthetic carotenoids may comprise an increased proportion of cis isomers relative to natural carotenoids. For example, synthetic forms of carotenoids such as lycopene may be up to 25% 5-cis, 1% 9-cis, 1% 13-cis, and 3% other cis isomers, whilst natural forms of carotenoids, for example lycopene produced by tomatoes, may be 3-5% 5-cis, 0-1% 9-cis, 1% 13-cis, and <1% other cis isomers. Since cis-carotenoids, such as cis-lycopene, have increased bioavailability relative to trans-carotenoids, such as trans-lycopene, synthetic carotenoids may be preferred in some embodiments.

Derivatives of carotenoids as described above may be produced by chemical synthesis analogous to the synthesis described above; by chemical modification of natural carotenoids extracted from plant material or by microbial, yeast, algal, or fungal fermentation. For example, lycopene may be produced by fermentation of the fungus *Blakeslea trispora* (e.g. Lyconat™, Vitatene SA).

The composition may comprise 0.05 to 90% by weight of the carotenoid compound, preferably 0.1% to 10% by weight. For example, the population may be 0.01% or more, 0.05% or more, 0.1% or more, 0.2% or more, 0.5% or more, 1% or more, 10% or more, or 20% or more by weight of carotenoid compound. The population may be up to 90%, up to 80%, up to 70%, up to 60% up to 50%, up to 40%, up to 30%, up to 20% or up to 10% by weight of carotenoid compound.

In some embodiments, a composition of the invention may comprise carotenoid particles. The composition may contain the same or similar amounts of carotenoid compound or the amount of carotenoid compound may vary between particles in the population. Each carotenoid particle in the population may comprise 0.05 to 90% by weight of carotenoid compound. For example, each carotenoid particle in the population may be 0.05% or more, 0.1% or more, 1% or more, 10% or more, or 20% or more by weight of carotenoid molecules. Each carotenoid particle may be up to 90%, up to 80%, up to 70%, up to 60% up to 50%, up to 40% or up to 30%, up to 90% or more by weight of carotenoid compound. In one instance, from 0.1% to 15% by weight of carotenoid may be present. In a preferred instance, from 1 to 15% may be present. For example, from 5 to 10% by weight of carotenoid may be present.

In one instance, a SFA, SCFA and/or MCFA may be used to increase the delivery of a carotenoid, such as any of those specified herein, after oral administration, where bioavailability is assessed by measuring the concentration of carotenoid in the serum. In one preferred instance, a composition employed for such purpose may comprise a SFA. In one preferred instance, a composition may comprise cocoa butter as the source of SFA and one or more carotenoid, such as any of those specified herein. In one preferred embodiment, compositions of the invention are employed to increase delivery of one or more Essential Fatty Acid.

In one particularly preferred embodiment of the invention, the carotenoid employed is one or more selected from lycopene, lutein, zeaxanthin, and/or astaxanthin. In a particularly preferred embodiment the carotenoid lycopene is employed. In a further particularly preferred embodiment, all three of lutein, meso-zeaxanthin, and zeaxanthin are present in a composition of the invention. In one preferred instance, the carotenoid employed is a polar carotenoid. In one particularly preferred instance, a xanthophyll is employed in a composition of the invention.

Carotenoids are anti-oxidants. Hence, the invention may be used to increase the anti-oxidant effect of a given amount of carotenoid, for instance a composition comprising SFA and the carotenoid may be employed for that purpose. One marker that may be used to assess a reduction in Inflammatory Oxidative Damage (IOD) is the level of IOD of serum lipoproteins, for instance using the methods described herein. Given the enhancement of the anti-oxidant effect, compositions comprising SFA and a carotenoid, may, for instance, be used to improve the treatment of inflammation and oxidative inflammatory damage. As show herein, the combination of carotenoid and SFA may be used to provide enhanced reduction of triglyceride, LDL, and cholesterol levels. Hence, the invention provides a method of reducing levels of triglyceride, LDL and/or cholesterol comprising administering orally a composition of the invention comprising a carotenoid and an SFA, particularly where the method results in an increased reduction compared to an equivalent composition lacking SFA, or one which comprises PUFAs or MUFAs. The invention may also be employed to lower the ratio of LDL:HDL. In an especially preferred embodiment the invention is used to lower serum triglyceride levels.

In one particularly preferred instance, the carotenoid employed may be lycopene. In one preferred instance, the carotenoid employed is one or more of lutein, meso-zeaxanthin and zeaxanthin, such as one, two or all of those carotenoids. The combination of all three is referred to herein as LMZ. Hence, in one preferred instance a composition of the invention may be LMZ SFA, LMZ PUFA or LMZ MUFA or such a composition may be employed in the invention. A further preferred carotenoid is astaxanthin and again that carotenoid in combination with any of SFA, PUFA, MUFA or both PUFA and MUFA may be employed.

In a further embodiment of the invention, compositions comprising MUFA, PUFA, and/or LCFA and particularly PUFA and/or MUFA and preferably PUFA are employed with carotenoids, such as those described herein, to bypass the liver, for instance to bring about delivery via the lymphatic system. The amounts of MUFA, PUFA, and/or LCFA may be any of those discussed herein. The carotenoid and the amount of it may be any of those discussed herein.

In one preferred instance, a composition of the invention is employed to increase the serum level of one or more carotenoid present in a composition of the invention following consumption. In a preferred instance, a composition of the invention comprising SFA, SCFA and/or MCFA as set out herein may be employed to do so, particular one comprising SFA as set out herein. It may be that the increase is that compared to that seen with a control, such as a composition comprising the same carotenoid(s), but one comprising MUFA, PUFA and/or LCFA as set out herein, particularly compared to one comprising PUFA as set out herein and the same carotenoid or carotenoids. It may be, for instance, the increase compared to the control is at least 50%, 60%, 70%, 80%, 90%, at least 100% or at least 150%. The increase seen compared to the control may be, for instance, a range comprising any of those values as endpoints, for instance 50 to 150%. In other embodiments, such improvements may be seen for serum IOD, for instance when measure at around 2 weeks following consumption compared to a control. Such improvements may be seen, for instance, for serum triglyceride levels. They may be seen for total cholesterol.

In one particularly preferred instance, a carotenoid may be used to help protect another agent from the effect of stomach acid, particularly the carotenoid particles discussed herein which may be included in a composition of the invention.

In further preferred embodiments of the invention:
(a) the carotenoid is lycopene;
(b) the carotenoid is lutein,
(c) the carotenoid is zeaxanthin;
(d) the carotenoid is astaxanthin;
(e) the carotenoid is mesozeaxanthin;
(f) the carotenoid is β- or α-carotene;
(g) the carotenoid is another, not listed above, carotene or xanthophyll;
(h) the carotenoid is a combination of carotenoids listed above
(j) the composition comprises 0.001% or more of carotenoid(s);
(k) the composition comprises 0.01% or more of carotenoids;
(l) the composition comprises 0.1% or more of carotenoids;
(m) the composition comprises 1% or more of carotenoids; and/or
(n) the composition comprises 10% or more of carotenoids.

Examples of further preferred compositions of the invention comprising carotenoids include the following:

A composition comprising: (a) one or more Essential Fatty Acids (EFA); (b) one or more carotenoids in an amount of at least 0.001% by weight; and (c) at least 5%, preferably at least 10%, of saturated fatty acids (SFA) and/or short chain fatty acids (SCFA) and/or medium chain fatty acids (MCFA).

Such a composition, wherein the composition comprises (a) at least 10% EFA; (b) at least 0.001% carotenoid; and at least 5%, preferably at least 10%, of saturated fatty acids (SFA) and/or short chain fatty acids (SCFA) and/or medium chain fatty acids (MCFA).

Such compositions, wherein the one or more carotenes are: (a) carotenoid (s); or (b) xanthophyll(s).

Such compositions wherein the carotenoid or carotenoids are any of those described herein.

Any of the above compositions wherein: (i) at least 10% DHA as an EFA, at least 0.005% carotenoid, and at least 5%, preferably at least 10%, SFA; (ii) at least 25% DHA as an EFA, at least 0.01% carotenoid, and at least 10% SFA; or (iii) at least 50% DHA as an EFA at least 0.01% carotenoid, and at least 10% SFA.

Preferred compositions include ones where: (i) the composition comprises the carotenoid lycopene; or (ii) the composition comprises one or both of lutein and zeaxanthin. In a particularly preferred embodiment, the composition comprises all three of lutein, meso-zeaxanthin and zeaxanthin Particularly preferred compositions comprise cocoa butter.

Any of the above compositions comprising: (a) one or more Essential Fatty Acids in a total amount of from 50 to 1000 mg; (b) one or more carotenoids in a total amount of from 1 to 25 mg; and (c) cocoa butter in an amount of from 50 to 500 mg.

Any of the above compositions comprising:
  (a) 125 to 550 mg DHA, 0.1 to 25 mg, preferably 3 to 20 mg, carotenoid, and 20 to 600 mg cocoa butter;
  (b) 200 to 500 mg DHA, 1 to 20 mg, preferably from 5 to 15 mg, carotenoid, and 40 to 500 mg cocoa butter;
  (c) about 250 mg DHA, about 7 mg carotenoid, and about 80 to 100 mg cocoa butter;
  (d) about 500 mg DHA, about 14 mg carotenoid, and about 160 to 200 mg cocoa butter; and/or
  (e) a composition comprising a multiple of any of (a) to (d).

Any of the above compositions comprising one or more EFAs, one or more carotenoids and cocoa butter, where the ratio of the three is:
  (a) 1 part EFA:0.002-0.1 parts carotenoids: 0.2-2 parts cocoa butter;
  (b) 1 part EFA:0.010-0.050 parts carotenoids: 0.25-0.50 parts cocoa butter;
  (c) 1 part EFA:0.020-0.040 parts carotenoids: 0.25-0.40 parts cocoa butter;
  (d) 1 part EFA:0.025-0.030 parts carotenoids: 0.25-0.35 parts cocoa butter;
  (d) any of (a) to (d) where the EFA is DHA;
  (e) any of (a) to (d) where the carotenoids is lycopene; or
  (f) any of (a) to (d) where the EFA is DHA and the carotene is lycopene.

A composition comprising about 250 mg DHA (or another EFA, or a combination of EFAs) plus about 7 mg lycopene (or another carotene) plus about 80-100 mg cocoa butter (or another product comprising mainly saturated and/or medium fatty acids).

A composition comprising about 125-500 mg DHA (or another EFA, or a combination of EFAs) plus about 3.5-14 mg lycopene (or a carotene) plus about 60-400 mg cocoa butter (or another product comprising mainly saturated and/or medium fatty acids).

A composition comprising 1 part of DHA (or another EFA, or a combination of EFAs): about 0.002-0.1 part of lycopene (or a carotene): about 0.2-2 part of cocoa butter (or another product comprising mainly saturated and/or medium fatty acids).

A composition comprising about 250 mg DHA (or another EFA, or a combination of EFAs) plus about 7 mg lutein and 1.4 mg zeaxanthin (or a xanthophyll, or a combination of xanthophylls) plus about 90-100 mg cocoa butter (or another product comprising mainly saturated and/or medium fatty acids).

A composition comprising about 125-500 mg DHA (or another EFA, or a combination of EFAs) plus about 3.5-14 mg lutein and about 0.7-2.8 mg zeaxanthin (or a xanthophyll, or a combination of xanthophylls and carotenes) plus about 50-400 mg cocoa butter (or another product comprising mainly saturated and/or medium fatty acids).

A composition comprising about 1 part of DHA (or another EFA, or a combination of EFAs): 0.002-0.1 part of lutein (or a xanthophyll): 0.0005-0.01 part of carotene): 0.2-2 part of cocoa butter (or another product comprising mainly saturated and/or medium fatty acids).

As discussed herein cocoa butter represents an especially preferred source of fatty acids for use with the invention. That is particularly the case where the composition comprises one or more carotenoids. Examples of preferred amounts of cocoa butter in a composition of the invention include from 10 to 75% by weight, such as from 15% to 30% by weight, or from 20 to 30% by weight of cocoa butter. For instance, a composition of the invention, particularly one comprising carotenoids may comprise from 50 to 300 mg of cocoa butter, such as from 50 to 300 mg of cocoa butter and in particular from 50 to 400 mg cocoa butter. In one preferred instance, a composition may comprise from about 80 to 100 mg of cocoa butter. In another preferred instance, a composition may comprise from 60 to 400 mg cocoa butter.

In a further preferred embodiment of the invention, a composition of the invention comprising a carotenoid and PUFA is used to lower systolic blood pressure. In a further embodiment it is used to lower diastolic blood pressure. In another embodiment, both systolic and diastolic blood pressure are lowered, the decrease may be, for instance, from 5 to 30 mm Hg, such as from 10 to 25 mm Hg, for example as measured four weeks from the start of administration.

In another preferred embodiment, a composition of the invention comprising MUFA, PUFA, and/or LCFA, particularly PUFA, as described herein, and one or more carotenoid is used to treat a prostate condition. In one especially preferred embodiment, the prostate condition is prostate hyperplasia. The carotenoid may be any of those described herein. For instance, in one embodiment one or more carotenoid is present selected from lycopene, β- or α-carotene, lutein, meso-zeaxanthin, zeaxanthin, and/or astaxanthin. In a preferred instance, the composition employed is lycopene. In one instance, such treatment results in a drop in IPSS score of from 5 to 25, such as from 8 to 20, for instance from 10 to 20. In one case the decrease in IPSS score is from 10 to 15. In one instance, such improvements are seen at about three months after the start of treatment.

Vitamins and Coenzymes as the Agent to be Delivered

In a further preferred instance, a composition of the invention may comprise a vitamin. Hence, the invention provides a way to increase the bioavailability of a vitamin or vitamins comprising allowing a subject to take a composition of the invention comprising SFA, SCFA and/or MCFA, particularly SFA, and a vitamin or vitamins. The invention provides a way to target a vitamin preferentially to, or via, the liver comprising administering a composition comprising SFA, SCFA and/or MCFA, particularly SFA, together with the vitamin or vitamins. Examples of vitamins which may be employed in the invention include vitamins A, B1-B9, B12, C, D1-D2-D3, E and K. In one especially preferred instance, the vitamin may be vitamin D. In a further preferred instance, the vitamin may be a Vitamin B, particularly Vitamin B12. In some instances, more than one vitamin may be present, for instance, the composition may be a multi-vitamin composition. Such, a multi-vitamin composition may comprise at least two, four, six, eight, ten, twelve or more vitamins, or a number of vitamins in a range comprising any of those two values as end-points. In one especially preferred instance, a composition of the invention may just comprise vitamin D or just vitamin B12 or both of those vitamins. In one preferred instance, a composition of the invention may comprise a vitamin or vitamins selected from vitamin, A, D, E and K, preferably two, three or four of those vitamins. In a particularly preferred instance, a composition of the invention may comprise all of vitamins A, D, E and K. Vitamin D associates with a carrier made by the liver hence compositions comprising SFA and vitamin D are particularly preferred as promoting delivery of vitamin D to the liver leads to higher bioavailability. Hence, the invention also provides a method of increasing vitamin D delivery to, or via, the liver comprising administering a composition of the invention to a subject which comprises vitamin D and an SFA, SCFA and/or MCFA. In a preferred instance, the composition comprises vitamin D and SFA.

It may be that the vitamin is the sole agent present. For instance, the present invention provides a vitamin supplement comprising a vitamin and SFA, SCFA and/or MCFA. The invention further provides a vitamin supplement comprising a MUFA, PUFA and/or LCFA, particularly one comprising PUFA and/or MUFA and especially comprising PUFA. In other embodiments, a vitamin or vitamins may be present in addition to one or more other agents, including any of those referred to herein. The invention also provides a method of targeting a vitamin to, or via, the liver, where the method comprises administering a composition comprising SFA, SCFA and/or MCFA, particularly SFA, together with a vitamin or vitamins. The invention also provides a method for increasing the bioavailability of a vitamin, comprising administering a composition comprising SFA, SCFA and/or MCFA, particularly SFA, together with a vitamin or vitamins.

In some instances, as well as vitamins, a composition of the invention may also comprise minerals, particularly those used in supplements. Examples of such minerals include, but are not limited to, boron, calcium, chloride, chromium, copper, iron, iodine, magnesium, manganese, molybdenum, phosphorus, potassium, selenium and zinc.

In some instances, a composition of the invention comprising vitamins may comprise vitamin(s) and/or minerals that are considered beneficial for a particular group. For instance, the invention may be, for instance, applied in particular to pregnant women, the elderly (for example over 60, 65, 70 or 75 years of age), or the young. For instance, it may be that a subject has been directed to take vitamin D and/or iron during pregnancy and/or whilst breast feeding and the invention provides a way to provide that. For instance, it may be that a subject has been directed to take vitamin D and/or other vitamins and/or minerals, such as any of those mentioned herein, and the subject may, for instance, be one who has a metabolic syndrome, a fatty liver, is overweight or obese. A subject may have a history of heart disease and/or a history of high blood pressure.

In a further preferred instance, the agent present in a composition of the invention may be a coenzyme. One particularly preferred coenzyme is coenzyme Q10, which is also sometimes referred to as ubiquinone, ubidecarenone, or coenzyme Q. Other examples of coenzymes include NAD, NADP, FAD, Coenzyme A, thiamine, pyridoxine, biotin and vitamin B12. Any of those coenzymes may, for instance, be present in a composition of the invention.

A composition of the invention may comprise any coenzyme. In one particularly preferred instance, a composition of the invention comprises coenzyme Q10. For instance, a composition of the invention may comprise SFA, SCFA and/or MCFA, particularly SFA, as described herein and co-enzyme 10. For example, such a composition may comprise from 10 to 1000 mg of coenzyme Q10. It may comprise from 25 to 500 mg of coenzyme Q10. In some instances, it may comprise from 50 to 250 mg of coenzyme Q10, for example from 75 to 150 mg of coenzyme Q10. Such compositions of the invention may be employed to increase serum concentration of coenzyme Q10 following oral consumption. For example, the increase in serum concentration of coenzyme Q10 may be at least 2, 3, 4, 5, 6, 7 or more fold compared to that seen with a control not comprising the SFA. The increase may be such levels, or at least 10, 15, 20 or 25 fold, such as at least 15 fold compared to the increase from baseline seen with a composition comprising PUFA such as that set out herein.

In one preferred embodiment, a composition of the invention may comprise one or more vitamin, for example one or more vitamins selected from vitamins $D_{1-2-3}$, $B_{12}$, $K_{2-4-7}$. In particular, the vitamin may be selected from $D_{1-2-3}$ and $B_{12}$.

Further Compositions Comprising Carotenoids in Combination with Other Agents

In one preferred instance, a composition as described herein may comprise one or more carotenoids, a further agent and a fatty acid as described herein and in particular SFA, SCFA and/or MCFA, especially SFA. In alternative embodiments, rather than SFA, it may be that MUFA, PUFA and/or LCFA may be employed, particularly PUFA and/or MUFA and especially PUFA. Hence, a composition comprising a SFA, SCFA and/or MCFA, particularly SFA, may be employed, particularly to target to, or via, the liver or alternatively a composition comprising a MUFA, PUFA, and/or LCFA, particularly PUFA and/or MUFA, and especially PUFA may be employed when the intention is to bypass the liver. Such compositions may comprise one or more carotenoids and a further agent.

In one particularly preferred embodiment, the other agent may be an essential fatty acid (EFA) such as any of those described herein. In one preferred instance, a composition of the invention may therefore comprise a carotenoid, EFA, together with SFA, SCFA and/or MCFA, particularly SFA. In one particularly preferred embodiment, the composition may comprises a carotenoid, EFA and a SFA. In one preferred embodiment, the carotenoid may encapsulate the EFA or the EFA may be embedded in carotenoid particles. Methods of preparing carotenoid particles are described in WO 2012/104576 which is incorporated in its entirety, particularly in relation to the types of particles described therein. Such particles may be formulated with SFA to produce a composition of the invention. Examples of carotenoid particles which may be employed include Lycosomes® which are, for instance, described in WO 2012/104576. Instances of particle types include micelles and reverse micelles, either of which may be employed. In one especially preferred instance, the EFA in such compositions is an omega 3 fatty acid. In one especially preferred instance, such compositions may be employed to help treat or prevent elevated levels of triglycerides, LDL and/or cholesterol, particularly triglyceride levels. Such compositions may be used to decrease the ratio of LDL:HDL. For instance, by targeting to the liver through the use of SFA, SCFA and/or MCFA and in particular SFA, it is thought that triglycerides, LDL and/or cholesterol can be successfully targeted given the role of the liver in processing triglycerides, LDL and/or cholesterol. Alternatively, in some instances it may be desirable to target the EFA so that it bypasses the liver and hence instead is preferentially targeted to the tissues, such as organs other than liver. In such instances, the composition may comprise MUFA, PUFA and/or LCFA and in particular a MUFA or PUFA, particularly a PUFA. Such targeting of EFAs to the peripheral tissues may be desirable in particular in promoting any of cognition, CNS development, eye function, and skin function.

Particularly preferred carotenoids which may be employed include any of those mentioned herein, particularly lycopene, xanthophylls lutein, meso-zeaxanthin and meso-zeaxanthin. In one preferred instance, a combination of xanthophylls lutein, meso-zeaxanthin and zeaxanthin (referred to as LMZ) may be employed and that also represents a preferred combination of carotenoids for employing in the invention. Such a combination may be in particular employed to lower triglyceride, cholesterol and/or LDL levels, particularly triglyceride levels. It may be employed to lower the ratio of LDL:HDL. It may be employed to reduce levels of inflammatory oxidative damage, for instance levels of acid inflammatory damage. Such combination compositions may though be employed to prevent or treat any of the conditions mentioned herein.

Phospholipids

In a further preferred embodiment, a composition of the invention may comprise phopholipid or phospholipids. Hence, any of the compositions described herein may also comprise a phospholipid. Such phospholipids may be present as the agent or in addition to other agents described herein. Phospholipids are typically amphiphilic lipids which consist of fatty acids esterified to a glycerol or sphingosine backbone, a phosphate group and a hydrophilic residue. In one preferred instance, a phospholipid employed in the invention may be phosphatidylcholine. One source of phospholipids which may be employed is lecithin. Sources of phospholipids include natural sources, such as eggs or soy, as well as synthetic ones. Any suitable phospholipid may be employed in the invention.

The phosphatidylcholine of the invention may be obtained from various sources such as egg yolk or soybeans. The term "phosphatidylcholine" is understood herein to include lecithin, 1,2-Diacyl-sn-glycero-3-phosphocholine, choline phosphatide, lecithol, posphatidyl-N-trimethylethanolamine, phospholutein. In certain embodiments, the phosphatidylcholine is 1,2-diacyl-sn-glycero-3-phosphocholine, 10-(perfluorobutyl)decyl phosphatidylcholine, dioleoyl phosphatidylcholine. Typically, the phosphatidylcholine of the invention is a commercially available purified form. Phosphatidylcholine is a glycerophosphocholine compound of structure II having O-acyl substituents at both the 1- and 2-positions of the glycerol.

Structure II

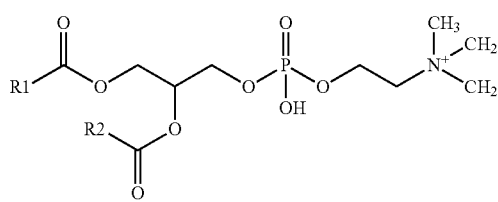

In a particularly preferred instance, phosphatidylcholine may be present as a phospholipid. The amount may be, for instance, between from 10% to 80%, for example at least 10%, 15%, 20%, 25%, 30%, 40%, 45% or more may be present. In some instances, the amount may be at least 50%, 55%, 60%, 70%, or 75%. The amount present may be in a range with any of the values mentioned in this paragraph as endpoints, for example from 10 to 20%, from 10% to 30%, from 15% to 25% and so on.

In embodiments where a phospholipid is present any of the conditions recited herein may be prevented or treated, preferred conditions include inflammation, cancer, cardiovascular disorders, neurological disorders, liver disease. Such embodiments may, in a preferred instance be used to help protect against or reduce the risk of liver disease. Such compositions may be administered to help aid or stimulate neurological development.

In one preferred instance, a composition of the invention may comprise a carotenoid and phosphatidylcholine, particularly where the carotenoid is any of those mentioned herein, preferably where it is lycopene. Such compositions may comprise any of SFA, SCFA, MCFA, MUFA, PUFA, and/or LCFA as outlined herein. Hence, preferred compositions will comprise SFA, SCFA, and/or MCFA, particularly SFA. Other preferred compositions may comprises MUFA, PUFA and/or LCFA, particularly MUFA and PUFA and preferably PUFA.

Other Active Agents to be Delivered

Whilst carotenoids, polyphenols and essential fatty acids represent particularly preferred instances of active agents to be delivered, the compositions provided may be used to deliver any suitable agent. Examples of other active agents which may be administered include:
(a) at least one of a protein, a peptide, and an amino acids, such as leucin, arginine;
(b) a nucleic acid;
(c) a polysaccharide;
(d) a natural or synthetic molecule; and/or
(e) a pharmaceutical or a nutraceutical, preferably one that is either needed by or activated in the liver.

In a further preferred instance, a statin may be used as the agent of the invention, particularly in those individuals with any of the conditions mentioned herein, such as elevated cholesterol, LDL and/or triglycerides, subjects with atherosclerosis and/or with heart disease. The subject may have an elevated ratio of HDL:LDL. A statin may be used as the sole active agent in a composition of the invention for preventing or treating a condition or may be used in combination with any of the other agents discussed herein. Any of the compositions discussed herein may therefore also comprise a statin.

In another preferred instance, the composition is one of those described herein for delivery for the liver, which additionally comprises one or more statins. Any of the compositions described herein may comprise one or more statin. In a particularly preferred instance, the composition will be one of those disclosed herein comprising a carotenoid, an EFA, and cocoa butter, particularly those comprising DHA, a carotenoid and cocoa butter and especially those described comprising DHA, lycopene and cocoa butter. In one instance, such compositions comprising statins may comprise one or more of lycopene, β- or α-carotene, lutein, meso-zeaxanthin, zeaxanthin, and/or astaxanthin. In one preferred instance, such compositions comprise at least two of lutein, meso-zeaxanthin and zeaxanthin. In a further preferred instance all three may be present.

In one preferred instance, the present invention also provides a method of delivering a statin to the liver, comprising orally administering to a subject in need thereof a composition comprising one or more EFA, a carotenoid and at least 10% SFA. In a preferred instance, the carotenoid will be a carotene, particularly lycopene. In a further preferred instance, the EFA is DHA. Examples of statins which may be present in such compositions include atorvastatin, fluvastatin, lovastatin, pravastatin, simvastatin, rosuvastatin, and pitavastatin. A composition may also comprise any combination of such statins. For instance, in some instances a composition may comprise both atorvastatin and amlodipine or both simvastatin and Etimibe. A composition of the invention comprising statins will comprise an effective dose, for example from 1 to 25 mg, such as from 5 to 20 mg or about such values. In some instances, a composition may comprise the recommended dose for a given statin.

In one particularly preferred instance, a composition of the invention may be one comprising an agent which is activated by the liver. For instance, the agent may be a pro-drug, which is only activated once it is metabolized by the liver. It may be a pro-enzyme that only becomes activated once it passes through the liver, for instance because proteolytic cleavage activates the drug in the liver. The invention provides for a method of increase activation of an agent, comprising administering a composition of the invention that comprises SFA, SCFA and/or MCFA and an agent that is activated by the liver, for instance by any of the processes for activation discussed herein. In a preferred instance, the composition comprises SFA and/or SCFA and in particular SFA. In one instance, in the invention an agent may be targeted to the liver so that it is oxidized, hydroxylated, conjugated to another entity or excreted into the bile. It may be that an agent undergoes modification which results in its activation.

In a further particularly preferred instance of the invention, a composition of the invention may comprise more than one active agent, for example one, two, three, four, five, six or seven agents or more. It may be that a composition comprises a number of agents in a range having any two of those values as endpoints. It may be that the composition, comprises from two to ten agents. For example, a composition may comprise from two to five agents. It may be that a composition comprises from two to four agents. In a preferred instance, any of the compositions discussed herein may comprise a vitamin or vitamins in addition to the other agents recited. It may be that the composition comprises a vitamin or vitamins, such as any of those mentioned herein, and a statin.

Saturated Fatty Acids (SFAs), Short Chain Fatty Acids (SCFAs) and Medium Chain Fatty Acids (MCFA)

In one instance, a composition of the invention comprises SFA, SCFA and/or MCFA and in particular SFA. Hence, any of the compositions of the invention may comprise SFA, SCFA and/or MCFA and in particular SFA, as described in this section unless otherwise stated. In one embodiment, at least 5% will be present by weight. For instance, in a preferred embodiment at least 10% will be present. In some cases, at least 25% will be present. In some preferred instances at least 50% will be present. For example, at least 50 to 99.9% may be present. For example at least 60% may be present. For instance, at least 75% may be present. In some cases, at least 80% may be present. It may be at least 90% is present. In some cases a composition may comprise at least half SFA, SCFA and/or MCFA and in particular SFA. For instance, from 50 to 95%. A composition may comprise at least 65%. For instance, from 50% to 80% may be present.

In one especially preferred instance, a composition of the invention may comprise a SFA, particularly where the composition is to promote bioavailability, particularly bioavailability at the liver. Compositions of the invention may also, in a preferred instance, comprise SFA where the aim is promote delivery to, or via, the liver. SFA may be employed to increase targeting to the liver. SFA may be employed to promote to targeting to the liver in a preferred instance where the agent being administered is one activated by the liver. An SFA may be employed in any of the embodiments of the invention unless otherwise stated, the SFA may be any suitable SFA, such as any of those mentioned herein, for example in any of the amounts specified herein. In a particularly preferred instance a composition of the invention may comprise at least 5% SFA. In a particularly preferred instance a composition of the invention may comprise at least 10% SFA.

In one especially preferred embodiment of the invention cocoa butter may be employed in the composition of the invention, for instance as a way to provide SFA. In a further preferred embodiment of the invention, coconut butter may be employed in a composition of the invention. In other preferred embodiments, $C_{12}$-$C_{18}$ and/or $C_4$-$C_{16}$ short- or medium fatty acids may be employed, particularly provided in the form of a product rich in such fatty acids. In one particularly preferred instance, the amount or percentage amount of SFA recited may therefore be provided by cocoa butter. It may be a composition is at least, for instance, 10% cocoa butter. It may be at least 25%. For instance, it may be at least 40% cocoa butter. A composition may be at least 50% cocoa butter. For instance, a composition may be at least 60%, 65%, 70% or 75% cocoa butter in some cases.

In one instance, a composition of the invention may comprises at least 5%, 10%, 15%, 20%, 25%, 30%, 35%, 40%, 50%, 55%, or at least 60% SFA. In one particularly preferred embodiment, the amount of SFA may be at least 5% by weight. In an especially preferred embodiment the amount of SFA may be at least 10% by weight. In further instances, the amount of SFA may be at least 65%, 70%, 75% or at least 80%. The amount of SFA may, for instance, be in a range comprising any of the values specified in this paragraph as endpoints. In a preferred instance, the amount of SFA in a composition of the invention may be at least 10%. In a further preferred embodiment the amount of SFA in a composition of the invention may be at least 20%. In a further preferred instance the amount of SFA may be at least 25%. In one embodiment, a composition may have any of such percentage values for the amount of saturated fat in the composition. In some cases, the amount may be at least 50% by weight.

In a further embodiment, a composition of the invention may comprise a substance which comprises SFA such as any of those specified herein. In one instance, a composition of the invention may comprises at least 5%, 10%, 15%, 20%, 25%, 30%, 35%, 40%, 50%, 55%, or at least 60% of such a substance. In further instances, the amount of SFA may be at least 65%, 70%, 75% or at least 80% of such a substance. The amount of such a substance may, for instance, be in a range comprising any of the values specified in this paragraph as endpoints. In a preferred instance, the amount of such a substance in a composition of the invention may be at least 10%. In a further preferred embodiment the amount of such a substance in a composition of the invention may be at least 20%. In a further preferred instance the amount of such a substance may be at least 25%. The substance may be any of those mentioned herein as comprising SFA, with preferred instances including chocolate, cocoa butter, butter, oils, and the other fat associated food products.

As will be appreciated, the ability to promote bioavailability can help increase the efficacy of an agent. Further, the ability to target to the liver offers a way to selectively targets agent in general to that organ, or such that the pass into the blood stream via that organ represents a powerful tool as well. The simplicity of the approach in simply being able to mix the active agent and SFA is also a large advantage compared to more complex formulation approaches. It may mean that less agent needs to be used and/or that a bigger effect may be achieved for the same amount of agent. The fact that less composition may be needed to achieve the same effect may also help with compliance.

Any suitable SFA may be employed in the invention. A SFA (saturated fatty acid) is one where the fatty acids all have single bonds and hence do not comprise double carbon bonds. Also included are esters, re-esterified triglycerides or salts thereof. In one preferred instance, the SFAs comprise, or are, $C_4$-$C_{18}$ fatty acids, for instance $C_4$-$C_{18}$ fatty acids, for instance $C_6$-$C_{18}$ fatty acids, such as $C_8$-$C_{18}$ fatty acids, preferably $C_{10}$-$C_{18}$ fatty acids and more preferably $C_{12}$-$C_{18}$ fatty acids. Examples of SFAs that may be employed include butyric acid (which contains four carbons and is found, for instance, commonly in butter), lauric acid (which contains twelve carbons and is found, for instance, in coconut oil, palm kernel oil, and breast milk), myristic acid (which contains fourteen carbon atom and is found, for instance, in cow's milk and other dairy products), palmitic acid (which contains 16 carbons and is contained in palm oil and meat) and stearic acid (which contains 18 carbons and is found, for instance, in meat and cocoa butter). Any of those SFAs or combinations thereof may be, for instance, employed in the invention and they may be, for instance, obtained from such sources as those specified. Synthetic SFAs may also be employed. Examples of SFAs which may be used include those comprising animal or plant fats. In one especially preferred instance a cocoa butter may be employed which comprises SFAs. In other instances, other animal or plant fats may be used, for instance, the composition may comprise a dairy fat or palm oil. Any suitable SFA may be employed.

In one instance, the composition employed may comprise at least 20%, at least 30%, at least 40%, at least 50% or at least 60% by weight of SFAs or in another instance a range having any combination of those values as endpoints. In other embodiments, the composition may, for instance, comprise at least 25%, 35%, 45%, 55% or 65% SFA by weight or in another instance may comprise a range having any combination of those values as endpoints. In one preferred instance, the composition comprises from 25 to 75% SFA, in particular from 30% to 60% SFA and preferably from 30% to 60% SFA by weight. In a particularly preferred instance, the composition comprises at least 30% by weight SFA. In a further preferred embodiment, a composition of the invention comprises at least 50% by weight of SFA.

In some instances, a composition of the invention may comprise not just SFAs but also other fatty acids such as MUFAs and PUFAs, but the amount of SFA will be any of the possible amounts by weight specified herein. In a particularly preferred embodiment, the amount of SFA will be at least 5%, 10%, 20%, 50% or 100% more than the amount of other fatty acids present and in a further preferred embodiment the amount of SFA present will be at least double of that of the other fatty acids present in the composition. In a further preferred embodiment other fatty acids than SFAs are not present, or at least are present in an amount less than 20%, preferably less than 15%, more preferably less than 10% and even more preferably less than 10% by weight. In other instances, the amount of other fatty acids than SFAs is less than 10%, less than 5%, less than 2% or less then 1% by weight.

Examples of compositions of the invention comprising SFAs, include a composition comprising SFA and a carotenoid, such as any of those mentioned herein. Further, examples include a composition comprising SFA and a polyphenol, such as any of those described herein. A further preferred composition is one comprising SFA and essential fatty acid, omega-3. In any of the compositions mentioned herein, the composition may further comprise a surfactant. In a particularly preferred instance the surfactant is phophatidylcholine, such as, for instance, lipoid P20 phophatidylcholine 20%. In one preferred instance, the amount of surfactant, for instance phosphatidylcholine, is in the range of from 2 to 20%, for instance, from 3 to 15%, preferably from 5% to 15% and more preferably from 5 to 10%. Hence, in one preferred instance a composition may comprise at least 30% SFA and from 5 to 10% surfactant, for instance where the surfactant is phosphatidylcholine. In a further preferred instance, the composition may comprise at least 50% SFA and from 5 to 10% of surfactant, such as, for instance, phophatidylcholine. In one preferred instance, the agent and SFA are blended together, particularly provided in capsules, such as gelatin capsules.

In other instances of the invention Short Chain Fatty Acids (SCFA) and/or Medium Chain Fatty Acids may be used instead of SFA or with SFA. Hence, in any of the embodiments discussed herein where SFA may be employed, SFA, SCFA, and/or MCFA may be employed. In one preferred instance, at least one, two or three of SFA, SCFA, and/or MCFA are employed. In one preferred instance, SFA may be employed, in a further preferred instance SCFA may be employed and in a further preferred instance MCFA may be employed.

SCFAs are typically fatty acids which are triglycerides comprising a glycerol backbone and three fatty acids with an aliphatic tail of less than six carbon atoms, they are also sometimes referred to as volatile fatty acids. Examples of SCFAs which may be employed include formic acid, acetic acid, propionic acid, butyric acid, isobutryic acid, valeric acid and isovaleric acid, in one preferred instance the SCFA employed comprises acetic acid, propionic acid and/or butyric acid. Any suitable source of SCFA may be employed in the invention. MCFA are typically fatty acids typically have chain lengths of six to 12 carbons in length, again having a glycerol backbone with three fatty acid chains. Examples of MCFA include caproic acid (C6), caprylic acid (C8), capric acid (C10) and lauric acid (C12), any of which may be employed in the compositions of the invention.

In one instance, a composition of the invention may comprises at least 5%, 10%, 15%, 20%, 25%, 30%, 35%, 40%, 50%, 55%, or at least 60% SCFA. In further instances, the amount of SCFA may be at least 65%, 70%, 75% or at least 80%. The amount of SCFA may, for instance, be in a range comprising any of the values specified in this paragraph as endpoints. In a preferred instance, the amount of SCFA in a composition of the invention may be at least 10%. In a further preferred embodiment the amount of SCFA in a composition of the invention may be at least 20%. In a further preferred instance the amount of SCFA may be at least 25%. In one embodiment, a composition may have any of such percentage values for the amount of saturated fat in the composition. In an alternative instance, a composition of the invention may comprise such amounts of MCFA.

In a further embodiment, a composition of the invention may comprise a substance which comprises SCFA such as any of those specified herein. In one instance, a composition of the invention may comprises at least 5%, 10%, 15%, 20%, 25%, 30%, 35%, 40%, 50%, 55%, or at least 60% of such a substance. In further instances, the amount of SCFA may be at least 65%, 70%, 75% or at least 80% of such a substance. The amount of such a substance may, for instance, be in a range comprising any of the values specified in this paragraph as endpoints. In a preferred instance, the amount of such a substance in a composition of the invention may be at least 10%. In a further preferred embodiment the amount of such a substance in a composition of the invention may be at least 20%. In a further preferred instance the amount of such a substance may be at least 25%. Again, in an alternative instance, a composition of the invention may comprise such amounts of SCFA.

In some instances, a composition may comprise more than one of SFA, SCFA and MCFA, for example: (i) SFA and SFC; (ii) SFA and MCFA; or (iii) SFA, SFC and MCFA. In one instance, the amount of (i), (ii) or (iii) present may cumulatively be any of the values given herein for the amount of SFA present or each of SFA, SCFA, and MCFA, if present, may be present in one of the values specified herein for SFA. For example, the amount of SFA, SCFA and MCFA present may total 5%, 10%, 15%, 20%, 25%, 30%, 35%, 40%, 50%, 55%, or at least 60%. In further instances, the total amount may be at least 65%, 70%, 75% or at least 80%. The amount may, for instance, be in a range comprising any of the values specified in this paragraph as endpoints. In a preferred instance, the total amount may be at least 10%. In a further preferred embodiment the total amount in a composition of the invention may be at least 20%. In a further preferred instance the total amount may be at least 25%.

In some embodiments of the invention, a composition may provide from 100 to 200 mg of EFA, particularly DHA. For instance, in some instances a composition may provide from 100 to 150 mg EFA and particularly DHA. In other instances, the composition may provided from 150 to 300 mg of EFA, particularly DHA. In other instances, the amount provided may be from 200 to 300 mg, such as from 225 to 275 mg or about 250 mg. In other instances, the EFA may be EHA and may be present in any of the amounts specified herein. The above amounts may, for instance, correspond to the amount provided in a capsule or tablet or other dosage form. In some instances, any of the agents employed in compositions of the invention may be in the above amounts.

Polyunsaturated Fatty Acids (PUFAs) and Monounsaturated Fatty Acids (MUFAs)

As discussed above, a particularly preferred embodiment of the invention is to use SFA, SCFA and/or MCFA to target to the liver and/or to increase bioavailability. In another preferred instance though PUFA, MUFA and/or LCFA, particularly PUFA and/or MUFA and in particular PUFA may be used to target an agent away from the liver. Hence, unless otherwise stated, a composition of the invention may be one comprising PUFA, MUFA and/or LCFA, particularly PUFA, as described in this section.

In one instance, a composition of the invention comprises PUFA, MUFA and/or LCFA, particularly PUFA. In one embodiment, at least 5% will be present by weight. For instance, in a preferred embodiment at least 10% will be present. In some cases, at least 25% will be present. In some preferred instances at least 50% will be present. For example, at least 50 to 99.9% may be present. For example at least 60% may be present. For instance, at least 75% may be present. In some cases, at least 80% may be present. It may be at least 90% is present.

Any of the agents mentioned herein may be targeted in such a way to preferentially bypass the liver. Hence, in a further preferred instance, a composition of the invention may comprise PUFAs, MUFA and/or LCFA, particularly PUFA and/or MUFA and especially PUFA, particularly where the composition is for bypassing delivery via the liver, for instance where delivery is to be via the lymph and typically then via the circulation to other tissues. In a particularly preferred instance PUFAs and/or MUFA are present, particularly PUFA, especially where the intention is for delivery to bypass or to favour bypassing delivery via the liver. PUFAs are fatty acids that comprise more than one carbon to carbon double bond in their backbone and MUFAs are fatty acids that comprise a single carbon to carbon double bond in their backbone. PUFAs and MUFAs include esters, re-esterified triglycerides, or salts thereof. Promoting the bypassing of the liver may be one way to help promote the bioavailability of an agent at a given tissue.

Examples of PUFAs which may be employed include:
  omega 3 fatty acids, for instance HTA, ALA, SDA, ETE, ETA, EPA, HPA, DPA, DHA, tetracosapentaenoic acid and tetracosahexaenoic acid;
  omega 6 fatty acids, for instance, linoleic acid, GLA, eicosadienoic acid, DGLA, AA, docosadienoic acid, adrenic acid, docosapentaenoic acid, tetracosatetraenoic acid, and tetracosapentaenoic acid;
  omega 9 fatty acids include, for instance, mead acid;
  conjugated fatty acids, such as, for instance, rumenic acid, alpha-calendic acid, beta-calendic acid, jaric acid, alpha-eleostearic acid, beta eleostearuc acid, catalpic acid, punicic acid, rumelenic acid, alpha parinaric acid, beta-parinaric acid and bosseopentaenoic acid; and
  other PUFAs such as pinolenic acid or podocarpic acid.

Any suitable PUFAs may be employed, including for instance any of those named above and in one preferred instance omega 3 fatty acids. In one particularly preferred instance, the composition comprises an oil or other fat comprising PUFAs.

In one instance, the composition employed may comprise at least 20%, at least 30%, at least 40%, at least 50% or at least 60% by weight of PUFA or in another instance a range having any combination of those values as endpoints. In other embodiments, the composition may, for instance, comprise at least 25%, 35%, 45%, 55% or 65% PUFA by weight or in another instance may comprise a range having any combination of those values as endpoints. In one preferred instance, the composition comprises from 25 to 75% PUFA, in particular from 30 to 60% PUFA and preferably from 30% to 60% PUFA by weight. In a particularly preferred instance, the composition comprises at least 30% by weight PUFA. In a further preferred embodiment, a composition of the invention comprises at least 50% by weight of PUFA. In some instances, a composition of the invention may comprise not just PUFAs but also other fatty acids such as SFAs and MUFAs, but the amount of PUFA will be any of the possible amounts by weight specified herein. In a particularly preferred embodiment, the amount of PUFAs will be at least 10%, 20%, 50% or 100% more than the amount of other fatty acids present and in a further preferred embodiment the amount of PUFA present will be at least double of that of the other fatty acids present in the composition. In a further preferred embodiment other fatty acids than PUFAs are not present, or at least are present in an amount less than 20%, preferably less than 15%, more preferably less than 10% and even more preferably less than 10% by weight. In other instances, the amount of other fatty acids than PUFAs is less than 10%, less than 5%, less than 2% or less then 1% by weight.

In one instance, a composition of the invention may comprises at least 5%, 10%, 15%, 20%, 25%, 30%, 35%, 40%, 50%, 55%, or at least 60% PUFA. In further instances, the amount of PUFA may be at least 65%, 70%, 75% or at least 80%. The amount of PUFA may, for instance, be in a range comprising any of the values specified in this paragraph as endpoints. In a preferred instance, the amount of PUFA in a composition of the invention may be at least 10%. In a further preferred embodiment the amount of PUFA in a composition of the invention may be at least 20%. In a further preferred instance the amount of PUFA may be at least 25%. In one embodiment, a composition may have any of such percentage values for the amount of polyunsaturated fat in the composition.

In a further embodiment, a composition of the invention may comprise a substance which comprises PUFA such as any of those specified herein. In one instance, a composition of the invention may comprises at least 5%, 10%, 15%, 20%, 25%, 30%, 35%, 40%, 50%, 55%, or at least 60% of such a substance. In further instances, the amount of PUFA may be at least 65%, 70%, 75% or at least 80% of such a substance. The amount of such a substance may, for instance, be in a range comprising any of the values specified in this paragraph as endpoints. In a preferred instance, the amount of such a substance in a composition of the invention may be at least 10%. In a further preferred embodiment the amount of such a substance in a composition of the invention may be at least 20%. In a further preferred instance the amount of such a substance may be at least 25%. The substance may be any of those mentioned herein as comprising PUFA.

In a further preferred instance, a MUFA may be present in a composition of the invention. Examples of MUFAs which may be employed include palmitic acid, palmitoleic acid, oleic acid, vaccenic acid, gamma-linolenic acid (GLA), gadoleic acid, and erucic acid. In some instances, the MUFA may be provided in the form of an oil, examples of these include olive oil, peanut oil, canola oil, sesame oil, and sunflower oil. Sunflower oil may be used as an oil which has PUFAs predominating, whilst olive oil may be used as an example of an oil where MUFAs predominate. Other examples of such oils include the high oleic variety of sunflower oil, canola oil, and cashew nut oil. Further examples of oils comprising MUFAs that may be employed include avocado oil, macadamia nut oil, grapeseed oil, peanut oil, sesame oil, corn oil, popcorn oil, whole grain wheat oil, safflower oil, almond oil, and hemp oil. In a preferred instance canola oil, olive oil or peanut oil is used.

In one instance, the composition employed may comprise at least 20%, at least 30%, at least 40%, at least 50% or at least 60% by weight of MUFA or in another instance a range having any combination of those values as endpoints. In other embodiments, the composition may, for instance, comprise at least 25%, 35%, 45%, 55% or 65% MUFA by weight or in another instance may comprise a range having any combination of those values as endpoints. In one preferred instance, the composition comprises from 25 to 75% MUFA, in particular from 30 to 60% MUFA and preferably from 30% to 60% MUFA by weight. In a particularly preferred instance, the composition comprises at least 30% by weight MUFA. In a further preferred embodiment, a composition of the invention comprises at least 50% by weight of MUFA. In some instances, the amount of MUFA present may be any of the amounts specified herein for SFA or PUFA.

In a further embodiment, a composition of the invention may comprise a substance which comprises MUFA such as any of those specified herein. In one instance, a composition of the invention may comprises at least 5%, 10%, 15%, 20%, 25%, 30%, 35%, 40%, 50%, 55%, or at least 60% of such a substance. In further instances, the amount of MUFA may be at least 65%, 70%, 75% or at least 80% of such a substance. The amount of such a substance may, for instance, be in a range comprising any of the values specified in this paragraph as endpoints. In a preferred instance, the amount of such a substance in a composition of the invention may be at least 10%. In a further preferred embodiment the amount of such a substance in a composition of the invention may be at least 20%. In a further preferred instance the amount of such a substance may be at least 25%. The substance may be any of those mentioned herein as comprising MUFA.

In some instances, a composition of the invention may comprise not just MUFAs but also other fatty acids such as SFAs and PUFAs, but the amount of PUFA will be any of the possible amounts by weight specified herein. In a particularly preferred embodiment, the amount of MUFAs will be at least 10%, 20%, 50% or 100% more than the amount of other fatty acids present and in a further preferred embodiment the amount of MUFA present will be at least double of that of the other fatty acids present in the composition. In a further preferred embodiment other fatty acids than MUFAs are not present, or at least are present in an amount less than 20%, preferably less than 15%, more preferably less than 10% and even more preferably less than 10% by weight. In other instances, the amount of other fatty acids than MUFAs is less than 10%, less than 5%, less than 2% or less than 1% by weight.

In some instances, a composition of the invention may comprise both PUFAs and MUFAs, for instance, where the combined amount of PUFA and MUFA is any of the values specified above for compositions comprising PUFA. In one preferred instance, a composition of the invention comprises an oil comprising both PUFAs and MUFAs but where the amount of PUFA is greater than the amount of MUFA that includes oils where the amount of PUFA is any of the values for PUFA specified herein. In one especially preferred embodiment the oil employed is sunflower oil.

Examples of compositions of the invention comprising PUFAs, include a composition comprising PUFA and a carotenoid, such as any of those mentioned herein. Further, examples include a composition comprising PUFAs and a polyphenol, such as any of those described herein. A further preferred composition is one comprising PUFAs and omega 3 fatty acids. In any of the compositions mentioned herein, the composition may further comprise a surfactant, particularly phosphatidylcholine, such as, for instance, lipoid P20 phosphatidylcholine 20%. In one preferred instance, the amount of surfactant, such as for instance phosphatidylcholine, is in the range of from 2 to 20%, for instance, from 3 to 15%, preferably from 5% to 15% and more preferably from 5 to 10%. Hence, in one preferred instance a composition may comprise at least 25% PUFAs and from 5 to 10% of surfactant, for instance phosphatidylcholine. In a further preferred instance, the composition may comprise at least 40% PUFAs and from 5 to 10% of a surfactant, for instance phosphatidylcholine.

In one particularly preferred instance of the invention a composition may comprise sunflower oil and a surfactant, particularly phosphatidylcholine, for instance, a composition may comprise from 40 to 99% sunflower oil, for example from 60 to 95% sunflower oil, preferably from 70 to 95% sunflower oil and more preferably from 80 to 90% sunflower oil by weight. Such compositions, may for instance comprise a surfactant, particularly phosphatidylcholine, in the range of from 2 to 20%, for instance, from 3 to 15%, preferably from 5% to 15% and more preferably from 5 to 10% by weight. In a further preferred embodiment of the invention a composition may comprise olive oil, rather than sunflower oil, for instance in the amounts specified herein for sunflower oil and may, for instance include a surfactant, for instance phophatidylcholine, for example in any of the amounts specified herein, particularly as specified herein in relation to compositions comprising sunflower oil.

In one particularly preferred instance, where MUFA and/or PUFA is employed, the target tissue may be the prostate, for instance compositions comprising MUFA and/or PUFA may be used to preferentially target a therapeutic agent, such as any of those discussed herein and in particular carotenoids such as those specified herein, to the prostate. Such an approach may, for instance, be used to treat any of the prostate conditions mentioned herein. In an especially preferred instance, such an approach is used to treat prostate conditions, particularly prostate hyperplasia. In one preferred instance, in such embodiments a carotenoid will be employed, such as any of those referred to herein. In a preferred instance, lycopene will be employed.

In one preferred instance, where a PUFA and/or a MUFA is employed the composition or method may be for reducing blood pressure or preventing high blood pressure. For instance, it may be employed to treat hypertension or prevent the onset of that condition. Alternatively, the method may be one for preventing or reducing hypoxia and/or helping to prevent tissue damage, such as that caused by hypoxia. The method may be one for improving tissue oxygenation.

In another instance, a composition of the invention may comprise a long chain fatty acid (LCFA), typically fatty acids where the carbon chain length is 13 carbons or greater. Where LCFA is present, rather than PUFA and MUFA, the amount of LCFA may be any of those values mentioned herein for PUFA or any of the values mentioned herein for MUFA. For instance, a composition of the invention may comprise LCFA in an amount of at least 5%, 10%, 15%, 20%, 25%, 30%, 35%, 40%, 50%, 55%, or at least 60% of such a substance. In further instances, the amount of LCFA may be at least 65%, 70%, 75% or at least 80%. Hence, in any of the embodiments described herein as employing a PUFA or MUFA it is possible to employ LCFA in their place with the amount and other parameters otherwise being the same. In other instances, LCFA may be employed with MUFA and/or PUFA. For example, the total amount of LCFA, MUFA and/or PUFA present may be any of the values outlined herein for PUFA or MUFA or it may be that each of PUFA, MUFA and/or LCFA has such values.

Formulation

Compositions of the invention may typically comprise, for instance, one or more pharmaceutically or nutraceutically acceptable carriers, excipients, buffers, adjuvants, stabilisers, or other materials, as described herein. The term "pharmaceutically acceptable" as used herein typically pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts, for example, Remington's Pharmaceutical Sciences, 18th edition, Mack Publishing Company, Easton, Pa., 1990. The term "nutraceutically acceptable" as used herein typically pertains to compounds, materials, compositions, and/or dosage forms which are in common or widespread usage in food and dietary products and are generally considered non-toxic, for example, compounds may have the US FDA designation "GRAS" (Generally Recognised as Safe), or equivalent food additive status in other jurisdictions. In one instance, a composition of the invention may just comprise the recited constituents, or consist essentially of the recited constituents. A composition may in particular be formulated in a preferred instance in a form suitable for oral administration, for instance inside a pill case suitable for oral administration. Oral administration is the especially preferred route of administration for compositions of the invention.

The formulations may conveniently be presented in unit dosage form and may be prepared by any methods well known in the art of pharmacy, food science or nutrition. Such methods include the step of incorporating a carrier which may constitute one or more accessory ingredients.

Formulations may be in the form of food products, beverages, liquids, solutions, suspensions, emulsions, elixirs, syrups, tablets, lozenges, granules, powders, capsules, cachets, pills, ampoules, ointments, gels, pastes, creams, sprays, mists, foams, lotions, oils, boluses, electuaries, or aerosols. A composition of the invention may be preferably in a form which is suitable for administration orally for delivery via the gastro-intestinal tract. Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste. In one particularly preferred instance, a formulation of the invention may be provided in a capsule, hence the present invention provides a capsule comprising a composition of the invention. Formulations of the invention will, in particular, be suitable for oral administration. Oral administration is the most preferred route of administration for the invention. In one instance, a composition of the invention is in liquid form. In one embodiment a composition of the invention is in liquid form inside a capsule. The invention therefore also comprises a capsule comprising a liquid of the invention.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Compositions for oral administration may further comprise sweeteners, texture modifiers, colourings and flavourings.

As used herein, the term "effective amount" refers to a quantity sufficient to achieve a desired effect and in particular a desired therapeutic and/or prophylactic effect. In some instances, an effective amount may refer to an amount of SFA, SCFA and/or MCFA, particularly SFA, needed to increase bioavailability of the agent being administered. A "therapeutically effective amount" may be, for instance, the amount needed to reduce or eliminate the presence, frequency, or severity of one or more signs, or symptoms of the conditions mentioned herein. In some embodiments, the amount of a formulation administered to the subject will depend on the type, degree, and severity of the disease and on the characteristics of the individual, such as general health, age, sex, body weight and tolerance to drugs. The skilled person will be able to determine appropriate dosages depending on these and other factors. Also provided herein is an oral pharmaceutical dosage form comprising any of the compositions described herein, particular a capsule comprising one of the compositions described herein, particularly a capsule provided a daily dose of an agent as described herein. In other embodiments, an effective amount may refer to the amount of PUFA, MUFA and/or LCFA, particularly PUFA and/or MUFA and especially PUFA. It may also refer to the amount of agent present.

Any suitable amount of a composition of the invention may be administered. The amount administered may, for instance, take into account the increased bioavailability seen, for instance be including the amount of agent necessary to include the same effect as a composition which does not take advantage of the invention. In other instances, the same amount of agent may be used and, preferably, a greater effect is achieved. The amount of the agent may be defined by the nature of the agent, for instance, by the recommended dose of the agent to treat the condition. Examples of doses include, for instance, from 0.1 to 10 g, from 0.2 to 5 g, from 0.5 to 1 g. In other instances, the dose may be from 1 to 500 mg, such as from 1 to 250 mg, for instance from 1 to 100 mg. In other instances the dose of the agent may be from 10 to 1000 µg, such as from 50 to 750 µg, or from 100 to 500 µg. In some instances, the amount of agent may be in a range defined by any two of the values mentioned by this paragraph. The amount of agent though will depend on the nature of the agent though, ideally an effective amount will be administered, such as a therapeutically effective amount. In one instance, where a carotenoid is being administered. The amount may, for instance, be from 1 mg to 50 mg, preferably from 1 to 25 mg, such as from 1 to 15 mg, such as from 1 to 10 mg. In one instance, a composition provides from 5 to 10 mg of carotenoid. In one instance, where the agent is a catechin or other polyphenol, the amount of the agent may be from 100 to 1000 µg, such as from 250 to 750 µg, or for instance from 300 to 600 µg. In one instance, where the agent is a polyphenol, such as trans-resveratrol, the amount present in a composition of the invention may be from 10 to 100 µg, such as from 10 to 50 µg, for instance about 10, 20, 30, 40 or 50 µg of carotenoid. In a further preferred embodiment, where the agent is an EFA, such as an omega 3 oil, the amount, may for instance, be from 0.1 to 5 g, such as from 100 mg to 1000 mg, for example from 250 to 750 mg. A composition of the invention may be in unit dose form, it may provide the recommended daily amount of an agent.

As used herein, the phrase "pharmaceutical composition" encompasses "nutritional compositions" or "nutritional supplements." However, any of the compositions described herein may be provided as a nutritional composition or supplement. A composition of the invention may be a "nutraceutical" and that term may includes: food products, foodstuffs, dietary supplements, nutritional supplements or a supplement composition for a food product or a foodstuff.

In one particularly preferred instance of the invention, a composition of the invention is prepared by blending the constituents present in the composition. In one particularly preferred instance of the invention the composition is then provided in tablet form or as a capsule containing a composition of the invention. In one instance, the compositions of the invention do not comprise micelles or reverse micelles. In an alternative embodiment they do so. In a further preferred instance of the invention, the active agent is whey. In an alternative preferred embodiment, the active agent to be delivered is not whey. In one preferred instance, a composition of the invention may be provided in an enteric soft capsule shell. The shell of a capsule may be, for instance, made of naturally occurring ingredients. In one preferred instance, a method of the invention may comprise taking a composition of the invention after a meal. A composition of the invention may be, for instance, given on a daily basis, for examples after meals, or for instance at any appropriate intervals such as at weekly, fortnightly or monthly intervals. In one preferred instance, the agent or agent is incorporated directly into the matrix of the substance comprising the SFA, SCFA, and/or MCFA, particularly directly into the matrix of cocoa butter. In another preferred instance the agent or agents is incorporated directly into the matrix of the substance comprising the MUFA, PUFA and/or LCFA, particularly directly into the matrix of the substance comprising the PUFA.

In one preferred instance, a composition of the invention may be one that does not need to be prescribed by a doctor to be administered. For instance, in a preferred embodiment of the invention a composition of the invention is a supplement. It may be that the composition is one sold as an over the counter medicine. It may be that the composition is a nutraceutical. In one preferred instance, a composition of the invention is not one that requires regulatory approval prior to marketing. In a particularly preferred instance, any such compositions may be ones which increase the bioavailability of the agent. However, the invention may be also applied to pharmaceutical products, such as those that have to be prescribed. A composition of the invention may be one with an active agent such as that the composition requires regulatory approval.

In any of the embodiment described herein an agent may be one that is associated with a carrier, for instance bound to a carrier. It may be that the carrier is one found naturally in the body and the administered agent associates with the carrier after administration. It may be that the carrier is administered with the agent.

In one embodiment, the invention provides a composition or method as substantially described herein, for instance as described herein in the Examples of the present application. Further Examples of Preferred Embodiments Employing Carotenoids As discussed elsewhere herein, in an especially preferred instance of the present invention a composition of the invention comprises one or more carotenoids. In some instances, the presence of carotenoid(s) may be used to further influence delivery. The following section sets out some preferred examples of compositions comprising carotenoids and their uses.

In one preferred instance, the present invention provides a composition comprising: (a) one or more Essential Fatty Acids (EFA); (b) a carotene in an amount of at least 0.001% by weight; and (c) one or more Saturated Fatty Acids (SFA)

in an amount of at least 5% by weight. In one preferred instance the amount of SFA is at least 10% by weight. In a particularly preferred instance the composition is for use in a method of increasing the bioavailability and/or activity of one or more Essential Fatty Acids (EFA) or in facilitating their delivery to, or via, the liver, of the EFA. Hence, the composition may be for increasing the bioavailability of the EFA or other active present. It may be for increasing the activity of the EFA in the body. In a preferred instance, it may be for use in facilitating the delivery of EFA to, or via, the liver. In a particularly preferred instance, the composition is one for oral administration.

In one preferred instance, the present invention therefore provides a composition for use in a method of increasing the bioavailability and/or activity of one or more Essential Fatty Acids (EFA) or in facilitating their delivery to, or via, the liver, of the EFA wherein the composition is administered orally and comprises: (a) one or more Essential Fatty Acids (EFA); (b) a carotene in an amount of at least 0.001% by weight; and (c) one or more Saturated Fatty Acids (SFA) in an amount of at least 5% by weight. In a particularly preferred instance, the SFA is present in an amount of at least 10% by weight. The carotene may be, for instance, any of those discussed herein. The SFA may be, for instance, any of those discussed herein.

In preferred instances of such compositions the composition comprises: (i) DHA as an EFA; (ii) a carotene, preferably where the carotene is lycopene; and (iii) cocoa butter as a source of SFA. In a particularly preferred instance, the composition comprises DHA, lycopene and cocoa butter. In other preferred instances, one or more carotenoid present is selected from lycopene, β- or α-carotene, lutein, meso-zeaxanthin, zeaxanthin, and/or astaxanthin. In a particularly preferred instance, at least one of lutein, meso-zeaxanthin and zeaxanthin is present. Preferably at least two of those carotenoids are present. More preferably all three of those carotenoids are present in a composition of the invention, particularly one comprising an EFA, particularly DHA and EPA, preferably one comprising DHA. As indicated above, preferably cocoa butter is employed as the source of SFA.

Further preferred instances of the invention include compositions where:
  the composition comprises: (a) one or more Essential Fatty Acids in a total amount of from 50 to 1000 mg; (b) one or more carotenes in a total amount of from 1 to 25 mg; and (c) cocoa butter in an amount of from 50 to 500 mg.
  the composition comprises: (a) 125 to 550 mg DHA, 3 to 20 mg carotene, and 20 to 600 mg cocoa butter; (b) 200 to 500 mg DHA, 5 to 15 mg carotene, and 40 to 500 mg cocoa butter; (c) about 250 mg DHA, about 7 mg carotene, and about 80 to 100 mg cocoa butter; (d) about 500 mg DHA, about 14 mg carotene, and about 160 to 200 mg cocoa butter; (e) a composition comprising a multiple of any of (a) to (d); (f) any of (a) to (f) where the carotenoid is lycopene.
  the composition comprises one or more EFAs, one or more carotenes and cocoa butter, where the ratio of the three is: (a) 1 part EFA:0.002-0.1 parts carotene:0.2-2 parts cocoa butter; (b) 1 part EFA:0.010-0.050 parts carotene:0.25-0.50 parts cocoa butter; (c) 1 part EFA: 0.020-0.040 parts carotene:0.25-0.40 parts cocoa butter; (d) 1 part EFA:0.025-0.030 parts carotene:0.25-0.35 parts cocoa butter; (d) any of (a) to (d) where the EFA is DHA; (e) any of (a) to (d) where the carotene is lycopene; or (f) any of (a) to (d) where the EFA is DHA and the carotene is lycopene.

Other preferred instances of the invention include a composition comprising 250 mg DHA plus 7 mg lycopene (or a carotene) plus 80-100 mg cocoa butter, or about such values. A further specific composition includes one comprising 25-500 mg DHA plus 3.5-14 mg lycopene (or a carotene) plus 60-400 mg cocoa butter or about such values. Another preferred embodiment is a composition comprising 1 part of DHA: 0.002-0.1 part of lycopene (or a carotene): 0.2-2 part of cocoa butter. Such compositions may be, for instance, employed in particular in helping to deliver the DHA to, or via, the liver. They may also be employed to help increase the bioavailability of the DHA or the same approach may be used to do so for other EFAs.

In instances of the invention where EFAs are being delivered to the liver, any of the conditions herein may be treated, particularly those discussed in relation to targeting the liver elsewhere in the present application. Preferred instances, include, using compositions comprising EFAs to reduce triglyceride levels. In cases where a carotenoid with anti-oxidative activity is employed, a method of the invention may in one preferred instance, reduced LDL oxidation, particularly where the carotenoid is lycopene.

In other preferred embodiments compositions comprising xanthophylls are provided. For instance, the present invention also provides a composition comprising (a) one or more Essential Fatty Acids (EFA); (b) one or more xanthophyll in an amount of at least 0.001% by weight; and (c) one or more Saturated Fatty Acids (SFA) in an amount of at least 10% by weight. In a particularly preferred instance, such a composition may be employed in a method of bypassing the liver following oral administration of the composition. Hence, in a preferred instance, the present invention provides a method of bypassing the liver following oral administration of the composition, wherein the composition comprises: (a) one or more Essential Fatty Acids (EFA); (b) one or more xanthophyll in an amount of at least 0.001% by weight; and (c) one or more Saturated Fatty Acids (SFA) in an amount of at least 5%, preferably at least 10% by weight.

In further preferred embodiments, such compositions, particularly those for bypassing the liver, may be:
  a composition comprising: (i) DHA as an EFA; (ii) lutein, zeaxanthin or a combination of both as the xanthophyll; and (iii) cocoa butter as a source of SFA (preferably such a composition will comprise all three of lutein, meso-zeaxanthin, and zeaxanthin as carotenoids present);
  a composition comprising DHA, cocoa butter, and one or both of lutein and zeaxanthin (preferably such a composition will comprise all three of lutein, meso-zeaxanthin, and zeaxanthin as carotenoids present);
  a composition comprising: (a) one or more Essential Fatty Acids in a total amount of from 50 to 1000 mg; (b) one or more xanthophylls in a total amount of from 1 to 25 mg; and (c) cocoa butter in an amount of from 50 to 500 mg.
  a composition comprising: (a) 125 to 550 mg DHA, 3 to 20 mg of xanthophyll, and 20 to 600 mg cocoa butter; (b) 200 to 500 mg DHA, 5 to 15 mg xanthophyll, and 40 to 500 mg cocoa butter; (c) about 250 mg DHA, about 7 mg xanthophyll, and about 80 to 100 mg cocoa butter; (d) about 500 mg DHA, about 14 mg xanthophyll, and about 160 to 200 mg cocoa butter; (e) a composition comprising a multiple of any of (a) to (d); or (f) any of (a) to (f) where the xanthophyll is lutein, zeaxanthin or both;

a composition comprising one or more EFAs, one or more carotenes and cocoa butter, where the ratio of the three is: (a) 1 part EFA:0.002-0.1 parts carotene:0.2-2 parts cocoa butter; (b) 1 part EFA:0.010-0.050 parts carotene:0.25-0.50 parts cocoa butter; (c) 1 part EFA:0.020-0.040 parts carotene:0.25-0.40 parts cocoa butter; (d) 1 part EFA:0.025-0.030 parts carotene:0.25-0.35 parts cocoa butter; (d) any of (a) to (d) where the EFA is DHA; (e) any of (a) to (d) where the carotene is lycopene; or (f) any of (a) to (d) where the EFA is DHA and the carotene is lycopene.

a composition comprising: (a) about 250 mg DHA, about 7 mg lutein and about 1.4 mg zeaxanthin, and about 90-100 mg cocoa butter; (b) about 125-500 mg DHA, about 3.5-14 mg lutein, about 0.7-2.8 mg zeaxanthin, and about 50-400 mg cocoa butter; or (c) the ratio of DHA:lutein:cocoa butter is 1 part of DHA: 0.002-0.1 part of lutein (or a xanthophyll): 0.0005-0.01 carotene: 0.2-2 part of cocoa butter.

Particularly preferred embodiments for delivery bypassing the liver include a composition comprising 250 mg DHA, 7 mg lutein, 1.4 mg zeaxanthin (or a xanthophyll, or a combination of xanthophylls), and 90-100 mg cocoa butter. Another preferred embodiment, particularly for delivery bypassing the liver, is a composition comprising 125-500 mg DHA, plus 3.5-14 mg lutein, 0.7-2.8 mg zeaxanthin (or a xanthophyll, or a combination of xanthophylls carotene), and 50-400 mg cocoa butter or about such amounts. A further preferred embodiment, particularly for bypassing the liver comprises 125-500 mg DHA, 3.5-14 mg lutein and 0.7-2.8 mg zeaxanthin (or a xanthophyll, or a combination of xanthophylls carotene), and 50-400 mg cocoa butter or about such amounts. Another preferred embodiment, particularly for delivery bypassing the liver, is a composition comprising 125-500 mg DHA, plus 0.5-14 mg lutein, 0.5-14 mg meso-zeaxanthin, 0.7-2.8 mg zeaxanthin (or a xanthophyll, or a combination of xanthophylls carotene), and 50-400 mg cocoa butter or about such amounts. A further preferred embodiment, particularly for bypassing the liver comprises 125-500 mg DHA, 0.5-14 mg lutein, 0.5-14 mg meso-zeaxanthin, and 0.7-2.8 mg zeaxanthin (or a xanthophyll, or a combination of xanthophylls carotene), and 50-400 mg cocoa butter or about such amounts.

Any of the compositions described in this section may also comprise one or more other active agents such as any described herein, in addition to the recited constituents. Hence, such compositions may be not just for delivering the EFA, but also the other active agent as well.

In one preferred embodiment, any of the compositions defined herein may be considered as a unit dose and the invention further provides a pack or kit comprising enough unit doses for a week, month, or three months or a range comprising any of those time points as endpoints, such as from a one to three months worth of unit doses, particularly unit doses for about a month.

Compositions of the invention comprising EFAs and particularly those comprising carotenoids may be, in one embodiment, employed to provide a daily dose of EFA to an individual.

An EFA present in any of the above compositions may be any of those described herein and in one particularly preferred instance DHA. In one especially preferred embodiment the EFA is omega 3.

Subjects and Conditions to be Treated

In one preferred instance, a composition of the invention may be administered not to treat a condition, but, for instance to simply ensure that a subject is given an agent with appropriate pharmacokinetic profile and level of bioavailability. For instance, the compositions of the invention may be employed as supplements, such as nutritional supplements or nutraceuticals. Hence, in one embodiment, the subject may be a healthy subject. In another preferred instance, a composition of the invention may be a vitamin supplement and the composition is taken simply to ensure the subject receives the vitamins it contains. In other embodiments, compositions of the invention may be used prophylactically, to help prevent or reduce the risk of developing a condition, such as any of those mentioned herein. In other embodiments, a composition may be used to treat any of the conditions mentioned herein. A composition of the invention may be given to help maintain the health of an individual.

Any of the compositions provided may be used to treat or prevent any of the conditions mentioned herein. As discussed above in relation to particular active agents, they may be useful in particular for treating particular disorders. Treatment may, for instance, also include prophylaxis as well as treatment once an individual actually has a condition. Any of the methods discussed herein may be used to prevent, or delay the onset of, a condition, such as the conditions specified or to treat the condition once it has arisen in an individual. Prevention and treatment includes reducing or eliminating symptoms of a particular condition, including any of the symptoms mentioned herein. In some instances, treatment may include, for instance, elimination of a condition or reducing the severity of the condition. It may, for instance, involve elimination or reduction of a symptom or symptoms of the condition. Treatment may include bringing about regression of a disorder. In one instance, the effect seen may be greater than if the same amount of an agent was administered without the SFA, SCFA, MCFA, MUFA, PUFA or LCFA. In a preferred instance, the effect seen may be a synergistic effect and so be greater than when either agent is administered individually. The synergy may be, for instance, in terms of increased bioavailability. It may additionally, or alternatively, be synergy in terms of better selective targeting. It may be, additionally or alternatively, synergistic in terms of the effect in preventing or treating the condition and its symptoms.

Compositions as described herein, particularly those intended to promote delivery to the liver, may be useful in the treatment or prevention of cardio- and cerebro-vascular disorders, hypertriglyceridemia, hypertension, metabolic syndrome, high blood pressure, pre-diabetes and type II diabetes, being overweight (e.g. BMI>25), obesity (e.g. BMI>30) or other medical conditions such as anaemia, rheumatism, rheumatoid arthritis, non-rheumatoid arthritis, prostate or testes malfunctions, liver diseases and disorders, erectile dysfunctions, loss of libido, cellulite, eczema, sarcopenia and cachexia. In one instance, the condition is hypercholesterolemia.

In some instances, the subject the invention is applied to may have an auto-immune disease; an allergic condition; hypertension; atherosclerosis; cardio pathologies, such as Coronary Heart Disease; vascular pathologies, such as endocarditis, myocarditis, heart failure, heart valve disease, arrhythmias, atherosclerosis, hypertension, vasculitis, endarteritis, varicose veins, endophlebitis, endothelial damage; cerebral pathologies; obesity; diabetes type 2; cancer, sarcopenia; metabolic dysfunction; Metabolic Syndrome; cellulite and aging tissue degradation; gastritis; stomach or duodenum ulcers; or arthritis; or dermatitis, psoriasis, acne, chronic skin ulcerations, or other age-related or skin conditions, including skin and other tissues burns and wounds;

sport, trauma, operation and other injuries; cachexia, side-effects of chemotherapies and radiation treatment, or radiation exposure; the subject may be at risk of such a condition. In one preferred instance, the subject may have diabetes or pre-diabetes. In a further preferred instance, the subject may be one at risk of diabetes.

The invention may also be used to treat conditions where increased oxygen transport may be beneficial. For instance, a subject with a respiratory disorder such as emphysema, COPD, cystic fibrosis, asthma, or ARDS or any other condition with coexisting hypoxia. The subject may have reduced lung function, for instance due to lung damage or lung cancer. In one instance, the subject may be a smoker. The invention may also be employed to help treat inflammatory or autoimmune disorders, for instance arthritis, inflammatory bowel disease and atherosclerosis.

The invention may also be used to treat impairment of tissue oxygenation, for instance due to reduction of blood supply due to circulatory dysfunction or circulatory disease. The subject may have had an injury, disease or disorder causing reduced blood flow, for instance one that results from blood flow to an organ and/or tissue being reduced or cut-off. The invention may be used to increase tissue oxygenation and treat circulatory disease. In one instance the circulatory disorder may be due to traumatic, compressive, occlusive, tumors/malformations and/or vasospastic reduction in oxygenation. The subject may have atherosclerosis resulting in reduced tissue oxygenation or DVT. The subject may be one with angina, such as angina pectoris, acute coronary syndrome, or had a myocardial infraction, endothelial dysfunction or tissue (preferably skin) healing insufficiencies. The invention may also be used to treat individuals with tissue inflammation due to ongoing inflammatory conditions or processes in the tissue, such as any of those referred to herein.

The invention may also be used to oxygen transport and tissue oxygenation in conditions accompanied by clinical or subclinical peripheral tissue hypoxia, such as skeletal muscle wasting conditions, age-related or functional, for example caused by weightlessness, or temporally reduced mobility caused by disease, trauma or operation. It could be conditions associated with irreversible loss of mobility caused by disease, trauma or operation, or advance age sarcopenia. The invention may also be used to improve physical and cognitive performance by boosting oxygen transport and tissue oxygenation, for example in sport, extreme physical and mental challenges.

In one preferred instance, particularly where the composition of the invention is being used to selectively deliver an active agent to the liver, the subject may be one who has a liver disorder. Examples of liver disorders include hepatitis, alcoholic liver disease, fatty liver disease, Wilson's disease, gilbert's syndrome, cirrhosis, liver cancer such as hepatocellular carcinoma or cholangiocarcinoma, primary biliary cirrhosis, and inflammation of the liver. In any of such embodiments, the agent being delivered preferentially to the liver may be one intended to treat the condition. In one preferred instance, the subject has cirrhosis, particularly alcoholic cirrhosis and the active agent is a drug to treat that condition. In any of the conditions where the intention is to promote delivery to the liver, a composition comprising an SFA as described herein may be preferentially employed. In further preferred instances where the composition employed is one intended to promote delivery to the liver, the condition to be treat may in a particularly preferred instance be elevated cholesterol, LDL and/or triglyceride levels and in particular elevated triglyceride levels. It may be used to lower the ratio of HDL:LDL. In a further preferred instance, the condition may be an inflammatory condition and in particular any of the inflammatory conditions mentioned herein.

In a further particularly preferred embodiment, the disorder to be treated may be a prostate disorder, particularly where the composition is one comprising a PUFA or MUFA and is intended to bypass delivery to the liver. In a preferred instance the composition will be one comprising a PUFA and/or MUFA and a carotenoid, particularly where the composition is one comprising a PUFA and a carotenoid. An example of a preferred composition is one comprising sunflower oil, lycopene and phosphatidylcholine, particular to treat or prevent a prostate condition. Examples of prostate conditions which may be treated include prostate inflammation (prostatitis), non-cancerous enlargement of the prostate (benign prostatic hyperplasia or BPH) and prostate cancer, any of those conditions may be treated and in a particularly preferred instance BPH is treated. Hence, the present application also provides a method for treating a prostate condition comprising administering a composition as described herein, particularly one comprising a PUFA as described herein, including where the condition to be treated is prostatitis, BPH or prostate cancer and especially where the condition is BPH. A particularly preferred carotenoid for use in such instances is one selected from lycopene, lutein, zeaxanthin, and/or astaxanthin. In a particularly preferred embodiment the carotenoid lycopene is employed.

In a further particularly preferred instance, the invention also provides a method for treating high blood pressure comprising administering a composition of the invention, particularly one comprising a PUFA and preferably one comprising a PUFA and carotenoid. A particularly preferred carotenoid for use in such instances is one selected from lycopene, lutein, zeaxanthin, and/or astaxanthin. In a particularly preferred embodiment the carotenoid lycopene is employed. In a further preferred embodiment, a combination of lutein, meso-zeaxanthin, and zeaxanthin is employed.

In particularly preferred embodiments of the invention, preferably where the composition is one for preferential delivery to the liver, the composition is employed in a method of: (a) promoting incorporation of carotenoid into low density lipoprotein particles, LDL to promote its bioavailability; (b) promoting protection of low density lipoproteins from peroxidation; (c) reducing elevated total cholesterol; and/or (d) reducing elevated LDL-cholesterol; (e) reducing oxidative damage reactions in the liver and/or metabolic consequences resulting from oxidative damage; and/or (f) reducing inflammatory oxidative damage reactions in the liver and/or metabolic consequences resulting from oxidative damage. In a further preferred embodiment, particularly where the composition is one for preferential delivery to the liver, the composition is for use in a method for: (a) reduction of elevated triglycerides; (b) increasing insulin sensitivity; (c) reduction of fasting glucose; and or (d) treatment or assisting to treat metabolic syndrome In further preferred embodiments, particularly where the composition is for delivery bypassing the liver, the method is for: reducing oxidative damage reactions in the peripheral outside liver organs and tissues; reduction of inflammatory oxidative damage reactions in other organs and tissues than liver and associated with this hypoxic and metabolic consequences. In further preferred embodiments the active agent is a carotenoid, preferably lycopene, and the method is for improvement of clinical and sub-clinical hypoxia and depressed oxygen tissue saturation, preferably to improve physical and mental performance or to prevent, alleviate or treat a condition selected from clinical and sub-clinical tissue hypoxia, age-associated skeleton muscle wasting conditions, sarcopenia, cachexia, heart failure, cancer, and a chronic organ/tissue wasting condition or disease. In a particularly preferred instance, the active agent delivered is lutein and or zeaxanthin, or other carotenoids, which can contribute into the health of the neurons, brain and its organs such as eye retina, and others. A composition of the invention, particularly one comprising EFA may in one instance be used to provide cognitive support. It may be, in another instance, used to prevent vision deterioration.

The invention may be applied to any suitable subject, individual or patient, they can be, for instance, an individual organism, a vertebrate, a mammal, or a human. In a particularly preferred instance, the invention is applied to a human. However, the invention may, for instance, also be applied to non-human animals, such a pets or commercial animals, such animals include, for instance, dogs, cats, cattle, pigs and sheep. In some instances, the subject may be elderly, for instance over 60, 65, 70, 75 or 80 years of age. The subject may be male or female. In some instances, the subject is pregnant. In some instances, the subject is under 18 years of age. For instance, the subject may be under 16 years, under 14 years, under 10 years or under 5 years. In one instance, the subject is under three.

In one embodiment, the condition to be treated is not a neurodegenerative condition or a condition affecting the nerves. In one embodiment, the condition is not an autoimmune condition. In one embodiment, the condition is none of a neurodegenerative condition, a condition affecting the nerves, and an autoimmune condition.

In one preferred instance, a composition of the invention may help reduce or prevent a side-effect or unwanted feature of an existing composition. For instance, a composition of the invention comprising EFA, particularly omega-3, may help avoid an increase of LDL, diarrhea, reflux, fishy taste or nausea. In one preferred instance, because less EFA, particularly omega 3, is needed a composition of the invention may not have, or have less of a, fishy taste. A composition of the invention may be less likely to induce nausea compared to simple administration of fish oil comprising a similar amount of omega 3 oil.

In one particular preferred instance of the invention, a composition of the invention may result in delivery of a higher amounts/ratio of the ingested DHA/EPA and/or other agents to peripheric tissues, among other brain, eye including eye retina, muscles, skin, and other organs and tissues. A composition of the invention may enhance the blood bioavailability level of the agent when compared to reference, control products, particularly where a composition of the invention comprises an EFA, especially an EFA.

In an especially preferred embodiment of the invention, a composition of the invention comprising one or more EFA and one or more carotenoid, may be employed to lower serum lipid levels. In a particularly preferred embodiment, such a composition may be one comprising SFA, SCFA, and/or MCFA, particularly SFA, as described herein. In particular, the composition will be one comprising DHA as described herein. In a preferred instance, the composition will comprise cocoa butter, Various further aspects and embodiments of the present invention will be apparent to those skilled in the art in view of the present disclosure. Unless context dictates otherwise, the descriptions and definitions of the features set out above are not limited to any particular aspect or embodiment of the invention and apply equally to all aspects and embodiments which are described. All documents mentioned in this specification are incorporated herein by reference in their entirety. The specific compositions described in the Examples of the application are also provided as compositions of the invention.

Additional Numbered Embodiments of the Invention

The following represent additional numbered preferred embodiments of the invention:

1. A composition comprising: (a) one or more Essential Fatty Acids (EFA); (b) one or more carotenoids in an amount of at least 0.001% by weight; and (c) at least 10% by weight of saturated fatty acids (SFA) and/or short chain fatty acids (SCFA) and/or medium chain fatty acids (MCFA).
2. The composition of (1), wherein the composition comprises (a) at least 10% EFA by weight; (b) at least 0.001% by weight of carotenoid; and at least 10% by weight of saturated fatty acids (SFA) and/or short chain fatty acids (SCFA) and/or medium chain fatty acids (MCFA).
3. The composition of (1) or (2), wherein the one or more carotenes are: (a) carotenoid(s); or (b) xanthophyll(s).
4. The composition of any one of (1) to (3), wherein:
   (i) at least 10% DHA as an EFA, at least 0.005% carotenoid, and at least 10% SFA;
   (ii) at least 25% DHA as an EFA, at least 0.01% carotenoid, and at least 10% SFA; or
   (iii) at least 50% DHA as an EFA at least 0.01% carotenoid, and at least 10% SFA.
5. The composition of any one of (1) to (5), wherein:
   (i) the composition comprises the carotenoid lycopene; or
   (ii) the composition comprises one or both of lutein and zeaxanthin.
6. The composition of any one of (1) to (5), wherein the composition comprises cocoa butter, preferably where the cocoa butter is the source of SFA, SCFA and/or MCFA and in particular SFA.
7. The composition of any one of (1) to (6) comprising:
   (a) one or more Essential Fatty Acids in a total amount of from 50 to 1000 mg;
   (b) one or more carotenoids in a total amount of from 1 to 25 mg; and
   (c) cocoa butter in an amount of from 50 to 500 mg.
8. The composition of any one of (1) to (7), wherein the composition comprises:
   (a) 125 to 550 mg DHA, 3 to 20 mg carotenoid, and 20 to 600 mg cocoa butter;
   (b) 200 to 500 mg DHA, 5 to 15 mg carotenoid, and 40 to 500 mg cocoa butter;
   (c) about 250 mg DHA, about 7 mg carotenoid, and about 80 to 100 mg cocoa butter;
   (d) about 500 mg DHA, about 14 mg carotenoid, and about 160 to 200 mg cocoa butter; and/or
   (e) a composition comprising a multiple of any of (a) to (d).
9. The composition of any one of (1) to (8), wherein the composition comprises one or more EFAs, one or more carotenoids and cocoa butter, where the ratio of the three is:
   (a) 1 part EFA:0.002-0.1 parts carotenoids: 0.2-2 parts cocoa butter;
   (b) 1 part EFA:0.010-0.050 parts carotenoids: 0.25-0.50 parts cocoa butter;
   (c) 1 part EFA:0.020-0.040 parts carotenoids: 0.25-0.40 parts cocoa butter;
   (d) 1 part EFA:0.025-0.030 parts carotenoids: 0.25-0.35 parts cocoa butter;
   (d) any of (a) to (d) where the EFA is DHA;
   (e) any of (a) to (d) where the carotenoids is lycopene; or (f) any of (a) to (d) where the EFA is DHA and the carotene is lycopene.

10. A composition for use in a method of increasing the bioavailability and/or activity of one or more Essential Fatty Acids (EFA) or in facilitating their delivery to, or via, the liver, of the EFA wherein the composition is administered orally and comprises:
(a) one or more Essential Fatty Acids (EFA);
(b) a carotene in an amount of at least 0.001% by weight; and
(c) at least 10% of saturated fatty acids (SFA) and/or short chain fatty acids (SCFA) and/or medium chain fatty acids (MCFA).

11. The composition of (10), wherein the composition comprises one or more Saturated Fatty Acids (SFA) in an amount of at least 10% by weight 12. The composition of (10) or (11), wherein the composition comprises:
(i) DHA as an EFA;
(ii) a carotene, preferably where the carotene is lycopene; and
(iii) cocoa butter as a source of SFA.

13. The composition of any one of (10) to (12), wherein the composition comprises DHA, lycopene and cocoa butter.

14. The composition of any one of (10) to (13) comprising:
(a) one or more Essential Fatty Acids in a total amount of from 50 to 1000 mg;
(b) one or more carotenes in a total amount of from 1 to 25 mg; and
(c) cocoa butter in an amount of from 50 to 500 mg.

15. The composition of any one of (10) to (14), wherein the composition comprises:
(a) 125 to 550 mg DHA, 3 to 20 mg carotene, and 20 to 600 mg cocoa butter;
(b) 200 to 500 mg DHA, 5 to 15 mg carotene, and 40 to 500 mg cocoa butter;
(c) about 250 mg DHA, about 7 mg carotene, and about 80 to 100 mg cocoa butter;
(d) about 500 mg DHA, about 14 mg carotene, and about 160 to 200 mg cocoa butter;
(e) a composition comprising a multiple of any of (a) to (d); or
(f) any of (a) to (f) where the carotenoid is lycopene.

16. The composition of any one of (10) to (15), wherein the composition comprises one or more EFAs, one or more carotenes and cocoa butter, where the ratio of the three is:
(a) 1 part EFA:0.002-0.1 parts carotene:0.2-2 parts cocoa butter;
(b) 1 part EFA:0.010-0.050 parts carotene:0.25-0.50 parts cocoa butter;
(c) 1 part EFA:0.020-0.040 parts carotene:0.25-0.40 parts cocoa butter;
(d) 1 part EFA:0.025-0.030 parts carotene:0.25-0.35 parts cocoa butter;
(d) any of (a) to (d) where the EFA is DHA;
(e) any of (a) to (d) where the carotene is lycopene; or
(f) any of (a) to (d) where the EFA is DHA and the carotene is lycopene.

17. A composition for use in a method of bypassing the liver following oral administration of the composition, wherein the composition comprises:
(d) one or more Essential Fatty Acids (EFA);
(e) one or more xanthophyll in an amount of at least 0.001% by weight; and
(f) one or more Saturated Fatty Acids (SFA) in an amount of at least 10% by weight.

18. The composition of (17), wherein the composition comprises one or more Saturated Fatty Acids (SFA) in an amount of at least 10% by weight 19. The composition of (18), wherein the composition comprises:
(i) DHA as an EFA;
(ii) lutein, zeaxanthin or a combination of both as the xanthophyll; and
(iii) cocoa butter as a source of SFA.

20. The composition of (19), wherein the composition comprises DHA, cocoa butter, and one or both of lutein and zeaxanthin.

21. The composition of any one of (17) to (20) comprising:
(a) one or more Essential Fatty Acids in a total amount of from 50 to 1000 mg;
(b) one or more xanthophylls in a total amount of from 1 to 25 mg; and
(c) cocoa butter in an amount of from 50 to 500 mg.

22. The composition of any one (17) to (21), wherein the composition comprises:
(a) 125 to 550 mg DHA, 3 to 20 mg of xanthophyll, and 20 to 600 mg cocoa butter;
(b) 200 to 500 mg DHA, 5 to 15 mg xanthophyll, and 40 to 500 mg cocoa butter;
(c) about 250 mg DHA, about 7 mg xanthophyll, and about 80 to 100 mg cocoa butter;
(d) about 500 mg DHA, about 14 mg xanthophyll, and about 160 to 200 mg cocoa butter;
(e) a composition comprising a multiple of any of (a) to (d); or
(f) any of (a) to (f) where the xanthophyll is lutein, zeaxanthin or both.

23. The composition of any one of (17) to (22), wherein the composition comprises one or more EFAs, one or more carotenes and cocoa butter, where the ratio of the three is:
(a) 1 part EFA:0.002-0.1 parts carotene:0.2-2 parts cocoa butter;
(b) 1 part EFA:0.010-0.050 parts carotene:0.25-0.50 parts cocoa butter;
(c) 1 part EFA:0.020-0.040 parts carotene:0.25-0.40 parts cocoa butter;
(d) 1 part EFA:0.025-0.030 parts carotene:0.25-0.35 parts cocoa butter;
(d) any of (a) to (d) where the EFA is DHA;
(e) any of (a) to (d) where the carotene is lycopene; or
(f) any of (a) to (d) where the EFA is DHA and the carotene is lycopene.

24. The composition of (23), wherein the composition comprises:
(a) about 250 mg DHA, about 7 mg lutein and about 1.4 mg zeaxanthin, and about 90-100 mg cocoa butter;
(b) about 125-500 mg DHA, about 3.5-14 mg lutein, about 0.7-2.8 mg zeaxanthin, and about 50-400 mg cocoa butter; or
(c) the ratio of DHA:lutein:cocoa butter is 1 part of DHA: 0.002-0.1 part of lutein (or a xanthophyll): 0.0005-0.01 carotene:0.2-2 part of cocoa butter.

25. A composition for use in a method of delivering a statin to the liver, the method comprising administering to a subject in need thereof a composition comprising
(a) one or more Essential Fatty Acids (EFA);
(b) a carotene in an amount of at least 0.001% by weight;
(c) at least 10% of saturated fatty acids (SFA) and/or short chain fatty acids (SCFA) and/or medium chain fatty acids (MCFA); and
(d) a statin or statins.

26. The method of (25), wherein the composition comprises the constituents set out in any one of (10) to (16) and a statin.

Further numbered embodiments of the invention include:
1. A composition for use in a method of targeting a water insoluble agent or agents, wherein:
(a) the method is for targeting the agent or agents to, or via, the liver, where the composition comprises: (i) at least 10% of saturated fatty acids (SFA) and/or short chain fatty acids (SCFA) and/or medium chain fatty acids (MCFA); and (ii) the water insoluble agent or agents; or
(b) the method is for targeting the agent or agent(s) so that it bypasses the liver, where the composition comprises: (i) at least 10% of monounsaturated fatty acids (MUFA), polyunsaturated acids (PUFA) and/or long chain fatty acids (LCFA); and (ii) the water insoluble agent or agents
2. A composition for use in the method of (1), wherein the method results in an increase in bioavailability and/or activity of the water insoluble agent or agents.
3. A composition for use in the method of claim 1) or (2), wherein the agent or agents are hydrophobic, lipophilic and/or amphiphilic.
4. A composition for use in any one of the preceding claims, wherein the agent or agents is/are selected from health supporting agent(s), health enhancing agent(s), nutritional agent(s), agents which are nutritional agent(s), preventative agent(s) and therapeutic agent(s).
5. The composition for use in the method of any one of (1) to (4), wherein the composition comprises:
(a) a surfactant, for example phosphatidylcholine and/or other phospholipids with similar structure-functional properties; and/or
(b) more than one agent.
6. The composition for use in the method of any one of (1) to (5), wherein the method is for targeting the agent or agents to, or via, the liver.
7. The composition for use in the method of (6), wherein:
(a) the saturated fatty acids are $C_{12}$-$C_{18}$ fatty acids;
(b) the saturated fatty acids are $C_4$-$C_{16}$ short- or medium fatty acids,
(c) the composition comprises 30% or more SFA, SCFA and/or MCFA; and/or
(d) the composition comprises 50% or more SFA, SCFA and/or MCFA.
8. The composition for use in the method of (6) or (7), wherein the composition comprises an agent selected from an essential fatty acid, a polyphenol, a carotenoid and a vitamin.
9. The composition for use in the method of any one of (6) to (8), wherein the composition comprises self assembled carotenoid entities with:
(a) an omega 3 DHA, or EPA, or other EFA, polyunsaturated molecules and their combinations, preferably where an anti-oxidant and/or chaperone is also present;
(b) a vitamin, for example vitamins $D_{1\text{-}2\text{-}3}$, or $B_{12}$,
(c) a carotene, for example lycopene;
(d) a xanthophyll, for example lutein, or meso-zeaxanthin, or zeaxanthin or astaxanthin,
(e) a combination of (c) and (d);
(f) at least one of resveratrol, an anthocyanin, an anthocyanidin, and a catechin;
(g) at least one of a protein, a peptide, and an amino acid, such as luceine, arginine;
(h) a nucleic acid;
(i) a polysaccharide;
(j) a co-enzyme;
(k) a natural or synthetic molecule; and/or
(l) a pharmaceutical or a nutraceutical, preferably one that is either needed by or activated in the liver.
10. The composition for use in any one of (6) to (9), wherein the agent is a carotenoid, preferably selected from lycopene, lutein, meso-zeaxanthin, zeaxanthin, and/or astaxanthin.
11. The composition for use in the method of claim any one of (6) to (10), wherein the method is for:
(a) promoting incorporation of a carotenoid into low density lipoprotein particles, LDL to promote its bioavailability;
(b) promoting other hydrophobic, or amphilic molecules, for example resveratrol, to be incorporated, or associated with lipoproteins produced by the liver to boost their bioavailability, concentration in the circulation and delivery level to other organs and tissues;
(c) promoting other hydrophobic, or amphilic molecules, for example catechins, to be metabolically activated by the liver to boost their bioavailability, concentration in the circulation and delivery level to other organs and tissues after passage via the liver;
(d) promoting protection of low density lipoproteins from peroxidation;
(e) reducing elevated total cholesterol;
(f) reducing elevated LDL-cholesterol;
(g) reducing the ratio of LDL:HDL;
(h) reducing oxidative damage reactions in the liver and/or metabolic consequences resulting from oxidative damage;
(i) reducing inflammatory oxidative damage reactions in the liver and/or metabolic consequences resulting from oxidative damage;
(j) improving bioavailability of Omega 3 and other EFA;
(k) neutralising Omega 3 side effects, for instance increase of LDL, diarrhea, or nausea; and/or
(l) reducing metabolically/therapeutically effective doses of Omega 3 and other EFA, which can improve their compliance.
12. The composition for use in the method of any one of (6) to (11), wherein the method is for:
(a) reduction of elevated triglycerides;
(b) increasing insulin sensitivity;
(c) reduction of fasting glucose; and/or
(d) treatment or assisting to treat metabolic syndrome.
13. The composition for use in the method of any one of (1) to (12), wherein the method is for targeting the therapeutic agent or agent(s) so that it bypasses the liver.
14. The composition for use in the method of (13), wherein:
(a) the saturated fatty acids are long chain fatty acids which are $C_{19}$ or longer fatty acids;
(b) the composition comprises 30% or more MUFA, PUFA and/or LCFA; and/or
(c) the composition comprises 50% or more MUFA, PUFA and/or LCFA.
15. The composition for use in the method of (13) or (14), wherein the delivery is via chylomicron particles that bypass liver.
16. The composition for use in the method of any one of (13) to (15), wherein the method is for:
(a) reducing oxidative damage reactions in the peripheral organs and tissues;
(b) reduction of inflammatory oxidative damage reactions in organs other than the live and tissues associated with hypoxic and metabolic consequences;
17. The composition for use in the method of any one of (13) to (16), wherein the active agent is a carotenoid, preferably lycopene, and the method is for improvement of clinical and sub-clinical hypoxia and depressed oxygen tissue saturation, preferably to improve physical and mental performance or to prevent, alleviate or treat a condition selected from clinical and sub-clinical tissue hypoxia, age-associated skeleton muscle wasting conditions, sarcopenia, cachexia, heart failure, cancer, and a chronic organ/tissue wasting condition or disease.

18. The composition for use in the method of any one of (13) to (17), wherein:
   (a) the agent is lutein and or zeaxanthin, or other carotenoids, which can contribute into the health of the neurons, brain and its organs such as eye retina, and others;
   (b) the agent is selected from resveratrol, anthocyanins, anthocyanidins, or a catechins;
   (c) the agent is selected from a protein or peptides or amino acids, such as leucine, or arginine;
   (d) the agent is selected from a nucleic acids, polysaccharides, natural or synthetic molecules;
   (e) the agent is selected from a pharmaceutical or nutraceuticals.

19. A composition comprising an omega 3 fatty acid or acids and at least 10% of saturated fatty acids (SFA) and/or short chain fatty acids (SCFA) and/or medium chain fatty acids (MCFA).

Further preferred embodiments include a composition for use in a method of targeting an agent or agents, to, or via, the liver, where the composition is administered orally in the method and the composition comprises: (a) at least 0.001%, preferably 1% at least 3% carotenoid and 15%, preferably at least 20% and more preferably at least 25% saturated fatty acid (SFA); and (b) an EFA, or EFAs, to be delivered.

In another preferred instance, in a composition of the invention, The composition for use in the method of claim 1 or 2, where: (a) the saturated fatty acids are $C_{12}$-$C_{18}$ fatty acids; (b) the saturated fatty acids are $C_4$-$C_{16}$ short-or medium fatty acids, (c) the composition comprises 30% or more SFA; and/or (d) the composition comprises 50% or more SFA.

EXAMPLES

Example 1 Preparation of Capsules Comprising the Carotenoid Lycopene and Cocoa Butter as an Example of a SFA The following provides an illustration of one approach for generating a composition of the present invention where a formulation comprising lycopene and cocoa butter, as an example of a SFA (Saturated Fatty Acid) rich constituent is prepared. In particular capsules were prepared containing lycopene using the following materials and equipment.

| Materials: | Equipment: |
|---|---|
| Lycored Lyc-O-Mato 15% | Temperature controlled incubator |
| Lipoid P20 phosphatidylcholine 20% | Laboratory balances |
| Cocoa butter | High speed hand blender |
| Size 00 gelatin capsules | Pipettors and tips |
| Beef gelatin | Capsule racks |
| | Capsule sealing machine |

Where capsules are to be used as part of a blinded study they can be prepared using red coloured size 00 gelatine capsules so that the appearance of the contents of the capsules does not mean the test capsules are different from the placebo. Lycored Lyc-O-Mato 15% is warmed to 50° C. following removal from 4-8° C. storage and mixed thoroughly. Each capsule generated comprises 7 mg lycopene and 10 mg phosphatidylcholine. The formulation for 300 capsules is determined as follows:

| 1 capsule | | ×300 capsules |
|---|---|---|
| 47 mg | Lyc-O-Mato 15% | 14.1 g |
| 50 mg | Lipoid P20 phosphatidylcholine 20% | 15.0 g |
| 650 mg | Cocoa butter | 195.0 g |

The cocoa butter is dispensed into a mixing bowl and placed in an incubator at 40° C. to melt the cocoa butter. Whilst the cocoa butter is still molten the Lycored Lyc-O-Mato 15% and the Lipoid P20 phosphatidylcholine 20% are added. The mixture is blended thoroughly using a high speed hand blender and the temperature of the mixture is maintained at 30 to 40° C. to ensure that it remains in a liquid state whilst it is dispensed. Using a microbalance a pipette is set to dispense 747 mg mass of the blended mixture. Size 00 capsules are placed in capsule rack. The bulk mixture is stirred with a silicone spatula during the dispensing in capsules to ensure uniformity of mixture during the dispensing process. 747 mg of the mixture is dispensed into each size 00 capsule. Caps are then placed on the capsules in a vertical position and the capsules are maintained in a vertical position in the capsule racks. The mixture in the capsules should then set at an ambient temperature of 25° C.

A mixture of 6 g beef gelatin/40 ml distilled water at 70° C. is then prepared and dissolved completely. The gelatin mixture is maintained at 60° C. in a water bath to keep the gelatin in a liquid state. Use a 200 µl pipette tip a thin seal of liquid gelatin is applied to each capsule. The gelatin seal is then allowed to dry at ambient temperature, with the seal preventing any leakage of blended mixture. The capsules are then sealed in blister packs with heat seal foil on capsule sealing machine and packed into boxes of 30 capsules and labeled ready for use.

The experiments described in subsequent Examples using cocoa butter comprising formulations as an example of SFA containing formulations were generated by the protocol described in this Example.

Example 2 Preparation of Capsules Comprising the Carotenoid Lycopene and Sunflower Oil as an Example of a PUFA The following provides an illustration of one approach for generating a composition of the present invention where a formulation comprising lycopene and a sunflower oil, as an example of a PUFA (Polyunsaturated Fatty Acid) rich constituent is prepared. In particular capsules can be prepared containing lycopene using the following materials and equipment.

| Materials: | Equipment: |
|---|---|
| Lycored Lyc-O-Mato 15% | Temperature controlled incubator |
| Lipoid P20 phosphatidylcholine 20% | Laboratory balances |
| Sunflower oil | High speed hand blender |
| Size 00 gelatin capsules | Pipettors and tips |
| Beef gelatin | Capsule racks |
| | Capsule sealing machine |

Where capsules are to be used as part of a blinded study they can be prepared using red coloured size 00 gelatine capsules so that the appearance of the contents of the capsules does not mean the test capsules are different from the placebo. Lycored Lyc-O-Mato 15% is warmed to 50° C. following removal from 4-8° C. storage and mixed thoroughly. Each capsule generated comprises 7 mg lycopene lycopene and 10 mg phosphatidylcholine. The formulation for 300 capsules is determined as follows:

| 1 capsule | | ×300 capsules |
|---|---|---|
| 47 mg | Lyc-O-Mato 15% | 14.1 g |
| 50 mg | Lipoid P20 phosphatidylcholine 20% | 15.0 g |
| 650 mg | Sunflower oil | 195.0 g |

The sunflower oil is mixed in a mixing bowl followed by the Lycored Lyc-O-Mato 15% and the Lipoid P20 phosphatidylcholine 20%. The mixture is blended thoroughly using a high speed hand blender. Using a microbalance a pipette is set to dispense 747 mg mass of the blended mixture. Size 00 capsules are placed in capsule rack. The bulk mixture is stirred with a silicone spatula during the dispensing in capsules to ensure uniformity of mixture during the dispensing process. 747 mg of the mixture is dispensed into each size 00 capsule. Caps are then placed on the capsules in a vertical position and the capsules are maintained in a vertical position in the capsule racks.

A mixture of 6 g beef gelatin/40 ml distilled water at 70° C. is then prepared and dissolved completely. The gelatin mixture is maintained at 60° C. in a water bath to keep the gelatin in a liquid state. Use a 200 µl pipette tip a thin seal of liquid gelatin is applied to each capsule. The gelatin seal is then allowed to dry at ambient temperature, with the seal preventing any leakage of blended mixture. The capsules are then sealed in blister packs with heat seal foil on capsule sealing machine and packed into boxes of 30 capsules and labeled ready for use.

The same protocol is employed for generating capsules comprising lycopene and olive oil as an example of a MUFA (monounsaturated fatty acid) rich constituent with the only change to the above protocol being the substitution of sunflower oil with olive oil.

Experiments in subsequent Examples employing sunflower oil and olive oil comprising compositions were all performed using capsules generated as described in the present Example.

Example 3 Study of SFA, MUFA and PUFA Mediated Delivery of Carotenoids and Identification of SFA as a Way to Facilitate Delivery to the Liver 3.1 Introduction Lycopene is a molecule belonging to the carotene group of compounds, is an oxygen free carotenoid and was chosen as a model carotenoid for the present study. Lycopene is one of the most potent antioxidants. Due to its highly hydrophobic properties Lycopene may be most effective within lipid or membrane cell structures. Due to those same hydrophobic properties lycopene cannot enter directly into existing lipid structures, but is incorporated at the time the structures are assembled.

Low Density Lipoproteins, LDL, are the main carrier of cholesterol in the circulation. Elevated LDL cholesterol is considered as one of the main risk factors in the development of atherosclerosis. However, unmodified LDL itself is a normal metabolite and is not harmful or pathogenic. At the same time, a modified, and in particular oxidized form of LDL, even at non-elevated level, is a strongly damaging and pathogenic molecule. LDLs are also the main carrier of triglycerides in the fasting plasma/serum. Elevated level of lipids is one of the main signs of the Metabolic Syndrome and a risk factor for development of not only atherosclerosis, but also Type 2 Diabetes. 90% of LDL in the body is produced in the liver. LDL is also one of the main carriers of Lycopene in the circulation.

In order to provide a delivery means for Lycopene and other carotenoids, a formulation comprising Lycopene embedded into predominantly saturated fatty acids (SFA) and in particular triglycerides with SFA, such as cocoa butter, was generated. It was found that such formulations of lycopene and SFA showed improved delivery via the portal vein and hence the liver. In particular, formulations with 20% or more SFA were found to be particularly effective at facilitating driving of molecules embedded into them predominantly to the portal vein system, and then to the liver. As an illustration of this formulations of Lycopene were also generated with predominantly polyunsaturated fatty acids (PUFA) such as sunflower oil and with monounsaturated fatty acids (MUFA) such as olive oil. It was found that SFA, MFA and PUFAs target the Lycopene differently and by selecting which is employed, it is possible to selectively target molecules via such "intelligent delivery". The results obtained are presented below.

3.2 Serum Lycopene Concentrations

A comparison was performed of the impact of SFA, MUFA and PUFA formulations containing lycopene on serum lycopene concentrations. As indicated above: cocoa butter was used as a model for SFA; olive oil was used as a model for MUFA; and sunflower oil was used as a model for PUFA. Table 1 below shows that the cocoa butter (SFA) Lycopene formulation provided the highest increase in serum lipoproteins of the Lycopene concentration, 380±39 ng/ml, against 200±21 ng/ml for the sunflower oil (PUFA) Lycopene formulation and 100±14 ng/ml the olive oil (MUFA) Lycopene formulation. The p values for the difference between effects of SFA formulation and PUFA was p<0.01 and between SFA and MUFA formulations was p<0.001. As serum concentrations of Lycopene are a measure of delivery via the portal vein and liver, the results obtained show that SFA provides improved delivery via that route compared to MUFA and PUFA formulations.

TABLE 1

Changes in serum lycopene concentration after supplementation with formulations of different fatty acids - 4 weeks trial.

| | | Serum Lycopene concentration, in ng/ml | | |
|---|---|---|---|---|
| Products | n | 0 weeks | 2 weeks | 4 weeks |
| Lycopene SFA | 8 | 460 ± 50 | 620 ± 64 Δ = 160 | 840 ± 86 Δ = 380 |
| Lycopene MUFA | 8 | 310 ± 34 | 480 ± 61 Δ = 170 | 420 ± 53 Δ = 110 |
| Lycopene PUFA | 8 | 300 ± 41 | 390 ± 49 Δ = 90 | 500 ± 52 Δ = 200 |

*Lycopene - 7 mg daily dose in one capsule.

3.3 Lipoprotein Mediated Protection from Oxidation

Next, the impact of the formulation on oxidation was measured, given the strong anti-oxidant activity of Lycopene, as a further way to study selective delivery to the serum via the portal vein and liver. Table 2 below shows that the cocoa butter (SFA) Lycopene formulation provided the fastest and the deepest inhibition of IOD (Inflammatory Oxidative Damage) in serum lipoproteins, by 51±5.2 µM on the second week of supplementation, while the olive oil MUFA formulation gave a lower inhibition by 30±3.1 and the sunflower oil PUFA formulation only displayed inhibition by 1±2.2 µM. By the end of the trial the final level of IOD for the formulations was that SFA was 45% of the baseline, MUFA 57% and PUFA 51%. The SFA formulation therefore again outperformed the MUFA and PUFA formulations in terms of promoting better delivery to the serum and hence a greater anti-inflammatory effect.

TABLE 2

Changes in the level of inflammatory oxidative damage in serum of volunteers after supplementation with lycopene formulated with different fatty acids - 4 weeks trial

| Products | n | Serum IOD in MDA µM | | |
|---|---|---|---|---|
| | | 0 weeks | 2 weeks | 4 weeks |
| Lycopene SFA | 8 | 121 ± 11 | 70 ± 8 (45%) Δ = −51 p < 0.05 | 54 ± 6 (45%) Δ = −67 p < 0.01 |
| Lycopene MUFA | 8 | 114 ± 10 | 84 ± 9 (74%) Δ = −30 p < 0.05 | 65 ± 7 (57%) Δ = −49 p < 0.01 |
| Lycopene PUFA | 8 | 132 ± 12 | 131 ± 11 (99%) Δ = −1 p > 0.05 | 67 ± 7 (51%) Δ = −65 p < 0.01 |

*Lycopene - 7 mg daily dose in one capsule.

3.4 Cholesterol and Triglyceride Reduction

The effect of the different formulations of Lycopene on liver-centered lipid metabolism were also studied with the results presented in the Table 3 below. Significant reductions of both cholesterol and triglycerides by some of these formulations was seen. The reduction of the total cholesterol for the SFA Lycopene formulation was by 26±2.9 mg/dL, the reduction for the PUFA formulation was only 65% of that seen with the previous product, specifically a reduction by 17±2.0 mg/dL, and the reduction seen for the MUFA was almost five times lower, specifically a reduction by 5±1.4 mg/dL.

The reduction of triglycerides seen for the SFA Lycopene formulation was 39±4.2 mg/dL, for the MUFA formulation it was only 38% of the previous product, specifically by 15±1.9 mg/dL, and for PUFA it was more than 10 times lower, specifically by only 3±0.6 mg/dL. The results obtained therefore again indicated that Lycopene formulation with SFA not only provided the highest level of incorporation of Lycopene into serum lipoproteins, which happens in the liver, but, probably as a result of that, provided the most effective lipoprotein protection from the Inflammatory Oxidative Damage (IOD). Overall, the other independent indication that SFA is more effective facilitator of the delivery of Lycopene to the liver, rather than MUFA or PUFA formulations, is that SFA had a significantly more profound effect on two other liver centered processes, namely cholesterol and triglyceride synthesis. The results seen therefore provide an illustration of the use of SFA as a way to selectively target a compound to the liver.

Example 4a. Study of SFA and PUFA Mediated Delivery of Trans-Resveratrol and Catechins

4.1 Introduction

The impact of SFA and PUFA formulations on delivery of trans-resveratrol and catechins was study. The results obtained are described further below, but in summary further confirm the ability SFA as a way to promote delivery to the liver, metabolic activation of polyphenols in this organ, and ultimately to increase their bioavailability.

4.2 Catechins

It is known that polyphenols in general, and Catechins in particular, have poor bioavailability when they are ingested in isolated or extracted form from food matrixes. Liver is one of the main organs which can enzymatically activate them and turn them into transportable molecules in forms of sulphated, glucuronidated and methylated epicatechins. We conducted a pharmacokinetic cross-over study on six volunteers, three men and three women, 35-55 years old. As a source of Catechins, and in particular of epicatechins we have chosen proprietary extract from berries of aronia, *Aronia Melanocarpa*. We prepared PUFA and SFA formu-

TABLE 3

Changes in total cholesterol and triglycerides concentration in serum of volunteers after supplementation with lycopene formulated with different fatty acids - 4 weeks trial

| Products | n | Total Cholesterol, mg/dL | | | Triglycerides, mg/dL | | |
|---|---|---|---|---|---|---|---|
| | | 0 weeks | 2 weeks | 4 weeks | 0 weeks | 2 weeks | 4 weeks |
| Lycopene SFA | 8 | 293 ± 23 | 274 ± 21 (94%) Δ = −19 p < 0.05 | 267 ± 21 (91%) Δ = −26 p < 0.01 | 212 ± 20 | 176 ± 18 (83%) Δ = −36 p < 0.01 | 173 ± 17 (82%) Δ = −39 p < 0.01 |
| Lycopene MUFA | 8 | 308 ± 21 | 298 ± 19 (97%) Δ = −10 p > 0.05 | 291 ± 18 (94%) Δ = −17 p < 0.05 | 135 ± 12 | 127 ± 10 (94%) Δ = −8 p < 0.05 | 120 ± 10 (89%) Δ = −15 p < 0.05 |
| Lycopene PUFA | 8 | 199 ± 16 | 194 ± 15 (97%) Δ = −5 p > 0.05 | 194 ± 15 (97%) p > 0.05 | 218 ± 18 | 216 ± 17 (99%) Δ = −2 p > 0.05 | 215 ± 16 (99%) Δ = −3 p > 0.05 |

*Lycopene - 7 mg daily dose in one capsule.

lations of with this extract, and also made control samples with extract only. Each capsule contained 400 μm of total catechins.

Each volunteer, after fasting for 12 hours, ingested in the morning, without breakfasts, one capsule of one of 3 products. All capsules were blinded and volunteers did not have knowledge of what particular formulation they were taking. Just before the ingestion of the capsules the first sample of venous blood was collected. After the ingestion the blood samples were collected every hour for 4 hours. Then these samples were centrifuged, serum was collected, aliquoted and frozen at −80° C. To help to ingest volunteers used still water. For the duration of this post-ingestion period no food was allowed but only water. This experiment was repeated with different formulations once every week. Then all frozen serum samples were sent for the chemical analysis. All samples were coded, hence blinded, and analysed at the same time.

Results from the experiment are presented on the FIG. 1. This graph shows mean value of the serum concentration of the volunteers after one hour of the ingestion of the capsules. From left to right in each group of the three columns in FIG. 1, the graph gives results for the catechin formulation with SFA, a control catechin formulation and a formulation with PUFA and catechins. The SFA formulation of the extract resulted in superior level of epicatechins bioavailability for all three forms of epicatechins measured. That superior level of epicatechin availability was seen on every time point when the blood was collected after ingestion of the products (results not shown).

4.3 Resveratrol

Bioavailability of trans-Resveratrol, t-RSV, in its isolated or extracted forms, as most of the polyphenols, is very poor. t-RSV is highly hydrophobic molecule and cannot be circulated in blood in a free form but only in an association with lipoprotein molecules. 90% lipoproteins are synthesized and produced by the liver. Hence, in order to boost bioavailability of t-RSV it needed to be directed after its absorption to this organ.

To verify this hypothesis we formulated t-RSV with SFA, and as a control we have its formulation with PUFA. As the source of resveratrol we used again aronia extract or particular cultivar, which contained unusually high level of this polyphenol. One capsule contained extract with 30 μg of t-RSV. Pharmacokinetics of these products was studied in the cross-over clinical trial of the same design as we did with catechin preparations (see above). Results of this study are presented in the table 4a. This table shows that formulation with SFA made trans-resveratrol 10 time more bioavailable, in terms of area under the curve, AUC, than with PUFA.

TABLE 4a

Pharmacokinetics of trans-Resveratrol in human serum in cross-over study.

| Product | AUC 0-4 hours, in ng/ml |
|---|---|
| trans-Resveratrol control | 0 |
| trans-Resveratrol SFA | 340 ± 41 |
| trans-Resveratrol PUFA | 34.5 ± 6.2 |

Example 4b. Study of SFA and PUFA Mediated Delivery of Ubiquinol, Coenzyme Q10

It is known that Coenzyme Q10 has a poor bioavailability. One of the factors, which may affect this, is that in order to be circulated in blood this molecule should be associated with proteins synthesised in the liver. Hence, in order to increase not its concentration in blood hence to enable Q10 to reach peripheral tissues it is important to direct delivery of this molecule after its absorption to the liver.

To verify this hypothesis we formulated Q10 with SFA, and as a control we have its formulation with PUFA. Pharmacokinetics of these two formulations together with commercial Q10, Solgar, was studied in 4-week parallel clinical trial. Results of this study are presented in the table 4b. This table shows that formulation with SFA made Q10 3 time more bioavailable, than with PUFA or the control product.

TABLE 4b

Comparison of Pharmacokinetics of different formulation of Q10 during 4 weeks of supplementation.

| | | | Serum Q10, in ng/ml | |
|---|---|---|---|---|
| | | | Incremental changes against the baseline | |
| Products | n | Baseline | 2 weeks | 4 weeks |
| 100 mg Q10 control* | 8 | 284 + 33 | 476 ± 52 $p < 0.01$ | 416 ± 45 $p < 0.01$ |
| 100 mg Q10 in SPA | 8 | 480 ± 51 | 1,339 ± 151 $p < 0.001$ | 1,418 ± 172 $p < 0.001$ |
| 100 mg Q10 in PUFA | 8 | 131 ± 18 | 379 ± 44 $p < 0.01$ | 451 ± 56 $p < 0.01$ |

Example 5 Use of SFA for Targeting Delivery, Boosting Efficacy and Reducing Side Effects of Essential Fatty Acids

5.1 Overview

Essential Fatty Acids, EFA, are important for humans as structural and functional molecules, and involved in many metabolic and physiological processes in our body. This encompasses, but is not limited to, the control of triglyceride synthesis and cellular membrane signaling, being critical structural element in nervous and other tissues, regulation of inflammatory reactions via modulation of the prostaglandin metabolism, etc. [1-5]. Since humans cannot synthesis EFA they can only get them from food, and in particular from plant, animal, fish or seafood products. Alternative or additional sources of EFA are nutraceuticals comprising EFAs, which may, for instance, include concentrated extracts from the above mentioned food sources or synthetic molecules.

5.2 Nutraceutical/Pharmaceutical EFA, Particularly Omega 3, Challenges

Whilst EFA supplements, and particularly omega 3 supplements, are widely used there are a number of challenges associated with their use which are discussed below.

5.1.1 High Dose

Advanced forms of EFA Omega-3 formulations have been registered as pharmaceutical products, for example Lovaza® and Epanova®. The metabolically active daily dose for triglyceride reduction is 4 grams. Weekly administration of this dose is more than 10 times higher than the one, which could be provided by daily consumption of 150 g of Alaska salmon for the same period. There are a number of reasons why extracted Omega 3 needs to be taken in such increased dose over the form, which is present in the food matrix [6, 7].

One of the reasons is that Omega 3, like other EFA, has a high number of unsaturated double bonds which can be easily oxidized by the stomach acid. When Omega 3 is ingested in an extracted and isolated form it is much more vulnerable to stomach degradation than when it ingested as a part of a food matrix. This could be due to at least two factors, one is that the pH of the stomach acid, when it is empty is pH 1.5-2. When stomach is full its pH can be 3-3.5 and the acid will not be so aggressive in its oxidising activity. The second factor is the presence of other molecules, such as antioxidants or chaperones, which can be co-present in the food, and which can protect or slow down loss of Omega 3, not only from the oxidation, but enzymatic degradation too. The other reason for why such a high dose of Omega 3 is needed to be administered to achieve triglyceride lowering effect is not related to the fact of its higher to the gastrointestinal modifying factors. It is due to the fact of indiscriminate, around the body, distribution of these fatty acids after their absorption via chylomicrons and passage into the lymphatic system. As result of this only a smaller part of these molecules can reach the liver as the main organ, which is responsible for synthesis of triglycerides.

The high dose daily intake present a significant impact on the compliance of the regular administration of Omega 3 products in their effective metabolic, therapeutic doses. As a result of this the target for the treatment of the serious metabolic/medical conditions may not be achieved, and their use for prevention has often been limited to the doses which are hardly expected to be efficient. It has also an effect on the overall cost of the omega 3 preparations as a multi capsule dose has to be taken daily to reach the desired tryglyceride reduction effect. There is therefore a need to boost the liver bioavailability of EFAs such as omega 3 fatty acids.

Hence, it is clearly desirable in one instance to provide a way to promote delivery of essential fatty acids, such as omega 3, to the liver, for instance to help lower LDL, cholesterol and/or triglyceride levels. The ability of the approach discussed herein of employing SFA, SCFA and/or MCFA as a way to target to, or via, the liver allows for that. Conversely, there are other instances, where it is more preferable to target essential fatty acids, such as omega 3, to the peripheral tissues, for instance to help improve cognition and nerve development. The ability to selectively target essential fatty acids to where it is most needed and also to minimize loss is therefore clearly important.

5.12 Side-Effects

Another challenge in the administration of Omega 3 is a number of side-effects, which can cause either withdraw of the patients from of the treatment, or serious concern by doctors which recommend this product. The side effects of products, which can be observed and experienced by patients are diarrhea, nausea, abdominal discomfort, fish taste reflux, fish taste in the mouth etc. If these effects are associated with the high amount of these oil-based products, another potential adverse reaction is intrinsically metabolic and are not normally noticed by the patient, but only by their doctor. In particular, it is an elevation in the concentration of the Low Density Lipoproteins, LDL, in the plasma of the persons who are taking Omega 3, particularly the increase in the ratio of LDL:HDL. Therefore, any prescription or recommendation for administration of these products in their metabolic/therapeutic doses must be accompanying by regular monitoring of the LDL blood level [8,9]. If this level starts to rise to a noticeable degree, then administration of Omega 3 should be terminated, even before it has achieved its treatment target. We offer a completely new way to overcome the above challenges. Any of the compositions of the invention, particularly those mentioned herein comprising EFA and especially omega 3, may be used to prevent or treat the above side-effects, for instance in eliminating or reducing them or ameliorating their severity.

5.2 Use of SFA with EFAs

As discussed further below, our approach shows that SFAs may be used for, amongst other things, any of the following:
  facilitating delivery of essential fatty acids to the liver not only without reducing but even increasing their availability for other organs and tissues;
  enhancing the ability of EFAs to reduce serum triglycerides which allows for use of a significantly lower metabolic active/therapeutic dose of EFA;
  not only to neutralize adverse reaction of Omega 3 on the LDL blood level, but achieve an opposite effect, namely its significant reduction; and/or
  enhancing antioxidant and anti-inflammatory efficacy of EFA.

5.3 the Principle of the Technology

EFA are PUFA, which would tend to be absorbed predominantly with larger chylomicrons, which would preferably go to the circulation via lymph system, rather than the portal vein. In order to facilitate the liver targeting delivery of these molecules we have used SFA. To further promote this we used self-assembling carotenoids, which have good affinity to interact with a broad range of lipids, including SFA and PUFA.

The other beneficial property of these carotenoids is that they are much more resistant to the stomach acidity and gut enzymes. Therefore their use to create self-assembling entities, Lycosomes, which can capture EFA, could help to protect these fatty acids from gastrointestinal oxidation and degradation [10].

We have already described above how SFA can facilitate liver targeting delivery of carotenoids themselves. In this case we have a new application for the delivery of their complexes with EFA. The other important factor is that it is not only possible, with our technology, to direct the most EFA molecules to the liver, it also highly desirable to let these fatty acids by-pass the liver and go via lymph system to circulation, where they can reach directly such other important organs and tissues, from the brain to the heart, from skeletal muscle to the skin. Therefore, we tried to introduce only a smaller percentage of SFA to the whole fatty acid content of the compositions we tested.

5.4 Method and Composition

The following provides an illustration of one approach for generating two compositions of the present invention where formulations comprising DHA, carotenoid and Cocoa Butter as a source of SFA were prepared. In one formulation the carotenoid was a carotene lycopene, and in another it was a combination xanthophylls Lutein, Meso-Zeaxanthin and Zeaxanthin, LMZ. In particular capsules can be prepared containing DHA-lycopene-Cocoa butter using the following materials and equipment.

Formulation 1

| Materials: | Equipment: |
|---|---|
| DSM life's DHA 40% | Temperature controlled |
| Lycored Lyc-O-Mato 15% | incubator |
| Cocoa Butter | Laboratory balances |
| Beef gelatine | High speed hand blender |
| Size 00 gelatin capsules | Pipettors and tips |
| | Capsule racks |
| | Capsule sealing machine |

Where capsules are to be used as part of a blinded study they can be prepared using red coloured size 00 gelatine capsules so that the appearance of the contents of the capsules does not mean the test capsules are different from the placebo. DHA should be allowed to thaw and warm up to ambient temperature following removal from −20° C. storage and is mixed thoroughly. Lycored Lyc-O-Mato 15% should be warmed to 50° C. following removal from 4-8° C. storage and mixed thoroughly. Each capsule is to contain 250 mg DHA and 7 mg lycopene. Formulation for 300 capsules is determined as follows:

| 1 capsule | | ×300 capsules |
|---|---|---|
| 625 mg | DSM life's DHA 40% | 187.5 g |
| 47 mg | Lycored Lyc-O-Mato 15% | 14.1 g |
| 88 mg | Cocoa Butter | 26.4 g |

Method:

The DHA and Cocoa Butter are dispensed into a mixing bowl followed by the Lycored Lyc-O-Mato 15%. They are blended thoroughly using a high speed hand blender. Microscopy verification of lycopene-based Lycosome™ assembly of required density may be performed by visualizing the particles.

Using a microbalance set a pipette to 752 mg mass of the blended mixture is dispensed. Size 00 capsules are set out in capsule racks. The blended mixture is dispensed as 752 mg per size 00 capsule. The bulk mixture is stirred with a silicone spatula to ensure uniformity of mixture during dispense process. Caps are placed on capsules and maintain capsules in a vertical position in the capsule racks. A mixture of 6 g beef gelatine/40 ml distilled water at 70° C. is prepared and dissolved completely. The gelatine mixture is maintained at 60° C. in a water bath to keep the gelatine in a liquid state. A 200 µl pipette tip is used to apply a thin seal of liquid gelatine to each capsule. The gelatine seal is allowed to dry at ambient temperature. The gelatine seal prevents leakage of blended mixture from capsules. The capsules are sealed in blister packs with heat-seal foil on capsule sealing machine. Boxes of 30 capsules are then packed and labeled.

Formulation 2

In particular capsules can be prepared containing DHA-LMZ-Cocoa butter using the following materials and equipment.

| Materials: | Equipment: |
|---|---|
| DSM life's DHA 40% | Temperature controlled |
| Lycored Lyc-O-Lutein 20% | incubator |
| PIVEG MariZ Zeaxanthin 20% | Laboratory balances |
| Cocoa Butter | High speed hand blender |
| Size 00 gelatin capsules | Pipettors and tips |
| Beef gelatine | Capsule racks |
| | Capsule sealing machine |

Where capsules are to be used as part of a blinded study they can be prepared using red coloured size 00 gelatine capsules so that the appearance of the contents of the capsules does not mean the test capsules are different from the placebo. DHA is allowed to thaw and warmed up to ambient temperature following removal from −20° C. storage. It is then mixed thoroughly. Lycored Lyc-O-Lutein 20%, which naturally contain its isomer Meso-Zeaxanthin in a ratio 50:50, is warmed to 50° C. following removal from 4-8° C. storage and mixed thoroughly. PIVEG MariZ zeaxanthin 20% is warmed to 50° C. following removal from 4-8° C. storage and mixed thoroughly.

Each capsule made contains 250 mg DHA and 7 mg lutein/1.4 mg zeaxanthin. Formulation for 300 of such capsules is determined as follows:

| 1 capsule | | ×300 capsules |
|---|---|---|
| 625 mg | DSM life's DHA 40% | 187.5 g |
| 35 mg | Lycored Lyc-O-Lutein 20% | 10.5 g |
| 7 mg | PIVEG MariZ zeaxanthin 20% | 2.1 g |
| 93 mg | Cocoa Butter | 27.9 g |

Method:

DHA and sunflower oil are dispensed into a mixing bowl followed by the Lycored Lyc-O-Lutein 20% and PIVEG MariZ zeaxanthin 20%. They are blended thoroughly using a high speed hand blender. Microscopy verification of LMZ-based Lycosome™ assembly of required density may be performed. Then the same procedure is performed as described above for formulation 1.

Formulation 3

Each capsule made contained 125 mg DHA and 7 mg lutein/1.4 mg zeaxanthin. Formulation for 300 of such capsules was as follows:

| 1 capsule | | ×300 capsules |
|---|---|---|
| 312.5 mg | DSM life's DHA 40% | 93.75 g |
| 35 mg | Lycored Lyc-O-Lutein 20% | 10.5 g |
| 7 mg | PIVEG MariZ zeaxanthin 20% | 2.1 g |
| 405.5 mg | Cocoa Butter | 121.65 g |

There were two objectives to create this formulation of DHA-LMZ-Cocoa. The first one was to verify whether increase of the DHA in blood and maybe some its effects, after its ingestion in our formulations, have some dose dependency.

The second objective was to increase SFA presence over PUFA. The commercial preparation of DHA contains two types of these fatty acids, 40% DHA and 60% Sunflower oil.

In addition, both lutein and zeaxanthin commercial products contained 80% of PUFA where these carotenoids were suspended.

Therefore in the Formulation 2 the ratio between SFA and PUFA was:
93 mg: [625±52.5=677.5] mg, or 1:7.28; and the product was where the PUFA was the dominant matrix.

with the dose of 250 mg, 124.6 µg/ml, but 2 fold higher than for 500 mg of the control DHA.

A similar dose dependent effect was observed for the serum EPA concentrations. The combined increase seen was 23.7 µg/ml for the ingested dose of 125 mg, and 40.8 µg/ml for 250 mg. The increase in the EPA for the control 500 mg DHA was only half of 125 mg our formulation, 11.6 µg/ml.

TABLE 5

Comparison of pharmacokinetics of DHA and EPA after 4 weeks of supplementation with different doses of DHA and its different carotenoid-SFA formulations

| Product | n | Serum DHA µg/ml | | | Serum EPA µg/ml | | |
|---|---|---|---|---|---|---|---|
| | | 0 w | 2 w | 4 w | 0 w | 2 w | 4 w |
| DHA 500 mg | 8 | 106 ± 11 | 134 ± 12 $\Delta$ = +28 | 108 ± 12 $\Delta$ = +2 | 56.5 ± 6.2 | 68.1 ± 7.4 $\Delta$ = +11.6 | 35.8 ± 5.3 |
| DHA 250 mg + Lycopene 7 mg PUFA:SFA = 7:1 | 8 | 95.7 ± 6.8 | 90.0 ± 9.4 | 92.0 ± 8.7 | 33.2 ± 6.4 | 33.1 ± 8.3 | 31.0 ± 7.9 |
| DHA 250 mg + LM 7 mg + Z 1.4 mg PUFA:SFA = 7:1 | 8 | 94.2 ± 12.5 | 117 ± 10.1 $\Delta$ = +22.8 | 196 ± 21.6 $\Delta$ = +101.8 | 49.5 ± 7.8 | 43.2 ± 3.2 | 90.3 ± 9.5 $\Delta$ = +40.8 |
| DHA 125 mg + LM 7 mg + Z 1.4 mg PUFA:SFA = 0.9:1 | 8 | 88.8 ± 8.5 | 109 ± 10.5 $\Delta$ = +20.2 | 129 ± 11.6 $\Delta$ = +40.2. | 26.1 ± 2.5 | 24.4 ± 2.3 | 49.8 ± 4.5 $\Delta$ = +23.7 |

In the Formulation 3 the ratio was:
405.5 mg: [312.5±52.5=365] mg, 1:0.90; in other words SFA was exceeding PUFA in this formulation.

We considered that if SFA can shift delivery of DHA, which is a PUFA itself, to the liver that could be used to increase its efficacy in targeting metabolic and inflammatory pathways in this organ.

Materials, equipment, methodology and product verification were the same as in preparation of the Formulation 2.

5.5 Clinical Validation

5.4.1 DHA and EPA Pharmacokinetics

The Data presented in the Table 5 demonstrates that daily administration of 500 mg of DHA alone resulted in a small increase in serum of DHA, by 26%, and EPA, by 21%, on the second week of the trial, and by the end of it, by week 4, their concentrations almost returned to the baseline level. Administration of the formulation of 250 mg DHA with Lycopene and SFA resulted in neither reduction nor increase of DHA and EPA in the serum of the patients. However, 250 mg DHA formulated with LMZ and SFA resulted in a significant steady increase in both DHA and EPA during whole trial period. The result seen represent an impressive observation given administration of this formulation, with only half of the control dose of DHA, resulted in 4 fold increased in the delivery of this fatty acid.

When supplementation was made with formulation containing 125 mg of DHA the combined increase in serum DHA for week 2 and week 4 was 60.4 µg/ml. This was about 50% lower than the increase observed for our formulation The DHA-carotenoid-SFA composition can also improve significantly pK profile and blood bioavailability of DHA and EPA at the blood level. Hence, the invention may be used to give a particular pK profile and/or bioavailability at the blood level, particularly by formulating essential fatty acids-carotenoids and SFA, SCFA and/or MCFA together. In a particularly preferred instance the EFA in such compositions is any of those mentioned herein, particularly DHA. In a further preferred instance SFA and/or SCFA and in particular SFA may be employed.

5.4.2 Effect on Liver Lipid Metabolism—Triglycerides and LDL

Comparison of results on the effects of SFA formulations of EFA on liver lipid metabolism are presented in the Table 6 below. DHA administration of 500 mg daily resulted in a significant reduction of serum triglycerides by 13 mg/dL. At the same time both of the SFA formulations of DHA, containing only half of the control dose, demonstrated significant triglyceride lowering effect, for DHA-LMZ reduction was by 17 mg/dL and for DHA-Lycopene by 25 mg/dL. In the control groups, when either lycopene or LMZ were administered in the same doses as they were present in the DHA formulations, there were no significant change in the triglyceride concentrations by the end of the trial. Since the liver is the main organ synthesizing triglycerides and produced into the circulation in lipoprotein particles, these results strongly indicate that the level of DHA and/or its efficacy in this organ was increased, when it was administered in these formulations comprising SFA.

TABLE 6

Comparison of effects on serum triglyceride and LDL level of DHA and its different carotenoid-SFA formulations - trial for 4 weeks.

| Product | n | Triglycerides, mg/dL | | LDL cholesterol, mg/dL | |
|---|---|---|---|---|---|
| | | 0 w | 4 w | 0 w | 4 w |
| DHA 500 mg | 8 | 197 ± 18 | 184 ± 17 (93%)<br>Δ = −13<br>p < 0.05 | 154 ± 16 | 149 ± 15<br>Δ = −5<br>p > 0.05 |
| DHA 250 mg +<br>Lycopene 7 mg<br>PUFA:SFA = 7:1 | 8 | 181 ± 19 | 156 ± 16 (86%)<br>Δ = −25<br>p < 0.01 | 141 ± 14.5 | 120 ± 12.5<br>Δ = −21<br>p < 0.01 |
| DHA 250 mg +<br>LM 7 mg + Z 1.4 mg<br>PUFA:SFA = 7:1 | 8 | 194 ± 17 | 177 ± 18 (91%)<br>Δ = −17<br>p < 0.05 | 141 ± 15 | 132 ± 13<br>Δ = −9<br>p < 0.05 |
| DHA 125 mg +<br>LM 7 mg + Z 1.4 mg<br>PUFA:SFA = 0.9:1 | 8 | 149 ± 15 | 130 ± 13 (87%)<br>Δ = −19<br>p < 0.01 | 138 ± 15 | 112 ± 12<br>Δ = −16<br>p < 0.01 |
| Lycopene 7 mg | 8 | 155 ± 12 | 150 ± 13 (97%)<br>Δ = −5<br>p > 0.05 | 158 ± 17 | 154 ± 16<br>Δ = −4<br>p < 0.05 |
| LM 7 mg + Z 1.4 mg | 8 | 188 ± 18 | 187 ± 18 (99%)<br>Δ = −1<br>p > 0.05 | 188 ± 18 | 185 ± 119<br>Δ = −3<br>p > 0.05 |

Administration of DHA in 500 mg dose did not affected LDL level in the serum of the participants. However, both our SFA formulations significantly reduced this parameter, the DHA-LMZ one by 9 mg/dL and the DHA-lycopene by 21 mg/dL. Administration of either Lycopene or LMZ themselves, for the same period of time and in the same doses, as they present in DHA formulations, did not affect level of LDL.

An interesting effect was observed, when the dose of the DHA was further reduced to 125 mg, in our clinical experiment, lipid-lowering effect was even stronger than of 250 mg dose, for triglycerides by 19 mg/dL and for LDL cholesterol by 16 mg/dL. This effect was observed despite a lower level of incremental serum DHA after administration of the former formulation than of the latter (please see above).

Since LDL and triglycerides are predominantly synthetized in the liver, one of the possible explanations of why the lower dose of 125 mg was stronger than 250 mg could be the fact that the reduced amount of DHA was "compensated" by addition of extra SFA, blended into our formulation, which resulted in more efficient delivery of DHA to its metabolic targets in this organ. In other words, these data confirm a dose dependency of SFA as a facilitator of the liver targeting delivery. Its nearly 4-fold dose increase in 125 mg formulation, and reduction of a ratio of the accompanying PUFA therein, resulted in 11% stronger for triglyceride- and 77% for LDL-lowering effect than its double dose of 250 mg formulation.

The importance of these observations is two-fold.

First, like for triglycerides liver is the main organ responsible for production of LDL. Hence significant changes in the level of these lipoproteins confirm observation above the liver-tropism of these new DHA-SFA formulations.

Second is that these new products were not just not affecting LDL level, which would be beneficial itself, by neutralising one of the main metabolic side effects of DHA, but actively reducing level of these lipoproteins.

This unexpected new property expands the use of DHA from not just triglyceride applications, but cholesterol/LDL lowering applications. In other words, the DHA-carotenoid-SFA products could be considered as a group of new interventional tools for comprehensive management of lipid metabolism. Hence, any of the compositions of the invention and particularly those involving EFA, such as those employing EFA, carotenoid and with SFA, SCFA and/or MCFA (particularly SFA) may be used to effect triglyceride, cholesterol and/or LDL. In particular, such compositions may be used to reduce serum triglyceride, serum cholesterol and/or LDL. Such compositions may be used to reduce levels of lipoproteins as described above.

Inflammation and Oxidative Damage

Since DHA itself has antioxidant and anti-inflammatory properties it was important to assess whether its formulation with carotenoids and SFA would change them. Comparison of the effects of DHA and its new formulations on blood markers of oxidative and inflammatory damage is presented in Table 7.

TABLE 7

Effects of DHA and its different carotenoid-SFA formulations on antioxidant and inflammatory blood markers - trial for 4 weeks.

| Product | n | IOD in MDA μM | | LDL-Px in ELISA × $10^3$ | |
|---|---|---|---|---|---|
| | | 0 w | 4 w | 0 w | 4 w |
| DHA 500 mg | 8 | 165 ± 18 | 107 ± 11 (65%)<br>Δ = −58<br>p < 0.01 | 700 ± 76 | 265 ± 27 (38%)<br>Δ = −435<br>p < 0.001 |

TABLE 7-continued

Effects of DHA and its different carotenoid-SFA formulations on antioxidant and inflammatory blood markers - trial for 4 weeks.

| Product | n | IOD in MDA μM | | LDL-Px in ELISA × 10³ | |
|---|---|---|---|---|---|
| | | 0 w | 4 w | 0 w | 4 w |
| DHA 250 mg + Lycopene 7 mg PUFA:SFA = 7:1 | 8 | 102 ± 10 | 37 ± 4.59 (36%) Δ = −65 p < 0.01 | 710 ± 74 | 98 ± 9 (14%) Δ = −612 p < 0.001 |
| DHA 250 mg + LM 7 mg + Z 1.4 mg PUFA:SFA = 7:1 | 8 | 111 ± 12 | 59 ± 6 (53%) Δ = −52 p < 0.01 | 1,110 ± 122 | 352 ± 15 (32%) Δ = −758 p < 0.001 |
| DHA 125 mg + LM 7 mg + Z 1.4 mg PUFA:SFA = 0.9:1 | 8 | 151 ± 14 | 92 ± 8.5 (61%) Δ = −59 p < 0.01 | 490 ± 55 | 167 ± 15 (34%) Δ = −323 p < 0.001 |
| Lycopene 7 mg | 8 | 111 ± 12 | 79 ± 9 (71%) Δ = −32 p < 0.05 | 133 ± 19 | 115 ± 14 (86%) Δ = −18 p > 0.05 |
| LM 7 mg + Z 1.4 mg | 8 | 72 ± 6 | 42 ± 4.5 (58%) Δ = −30 p < 0.05 | 447 ± 46 | 262 ± 29 (59%) Δ = −185 p < 0.001 |

These results demonstrate that LMZ-DHA-SFA formulation has comparable anti-IOD activity with DHA alone or with preparation, which contained only LMZ blend. It was interesting to note that Lycopene-DHA-SFA formulation was significantly stronger than either DHA or lycopene itself.

A synergetic affect was observed with regard of anti-inflammatory properties of DHA for its both carotenoid-SFA formulations. After 4 weeks of supplementation with DHA-Lycopene-SFA the level of this marker was reduced by 612×10³ ELISA units, which is stronger by 159×10³ ELISA units if effects of DHA alone and lycopene were added. For DHA-LMZ-SFA synergetic impact was also observed albeit of a slightly lower value of 138×10³ ELISA units. It is worth pointing out that the real synergetic effect may be even more profound, because in both of those carotenoid-SFA formulations only half of the dose of the control DHA was used.

Example 6 Facilitation of Delivery Via Non-Liver Routes 6.1 Overview

There are four organs in the human body which have the highest level of carotenoid receptors—they are the liver, adrenal glands, testes and prostate. Having identified how to selectively target to the liver, the possibility of reducing carotenoid "traffic" to the liver was investigated as a way to bypass liver delivery and hence instead increase delivery to the peripheral organs and tissues. Two formulations comprising Lycopene embedded into predominantly MUFA or PUFA were generated as a model for facilitate driving of the molecules embedded into them to the lymph system and so to reduce transport via the portal vein. These formulations were hence investigated for their ability to bypass delivery to the liver and instead increase its delivery to the peripheral tissues. Just as SFA were identified as a way to increase delivery via the liver, the use of MUFA and PUFA formulations of carotenoids, such as Lycopene, do the converse.

6.2 Lymph Chylomicron Transport

As mentioned above, delivery via the portal vein to the liver can be promoted using SFA. The ability of MUFA and PUFA to switch delivery away from that route was studied using postprandial crossover studies on 10 volunteers. In the first experiments Lycopene concentration was determined in postprandial blood after the volunteers had ingested one capsule of 7 mg of lycopene in MUFA formulation. After a one week break, the same volunteers were asked to ingest one capsule of 7 mg of Lycopene, but this time instead in a SFA formulation, rather than a MUFA formulation. In both experiments, the appearance of chylomicrons in the blood of the volunteers could not be identified and no changes were seen in the serum lycopene concentration of the volunteers.

In the next study, it was decided to boost bioavailability of Lycopene in both formulations, but to keep the same fatty acid environment. In the same crossover design, 10 volunteers were again asked to ingest the same 7 mg Lycopene MUFA, as in the above experiment, but at the same time with 50 g of virgin olive oil. After one week rest, the same volunteers were asked to ingest a 7 mg lycopene formulation in SFA with 50 g of cocoa butter. As indicated above, olive oil provides MUFA and cocoa butter SFA. The results of the study are presented in Table 8 below. They show that ingestion of 50 g of virgin olive oil resulted in a significant appearance of chylomicrons in the blood of the volunteers, with the maximum value at three hours after ingestion of the oil. The concentration of chylomicrons after ingestion of the same amount of the fat, but this time in a form of cocoa butter, resulted in the three fold lower number of these molecules (please see the top half of Table 8).

TABLE 8

Postprandial concentration of chylomicrons and lycopene after its ingestion with MUFA or SFA
top table - changes in serum chylomicron concentration, in terms of nephelometry
light scattering; bottom table - changes in serum lycopene concentration.

| Lycopene MUFA Chylomicron Light Scattering Δ in nephelometric units, LSI | | | | Lycopene SFA Chylomicron Light Scattering Δ in nephelometric units, LSI | | | |
|---|---|---|---|---|---|---|---|
| Postprandial time | | | AUC | Postprandial time | | | AUC |
| 1 h | 2 h | 3 h | 1-3 hours | 1 h | 2 h | 3 h | 1-3 hours |
| 89 ± 9.3 | 158 ± 17.3 | 168 ± 18.2 | 415 ± 42.5 | 25 ± 3.1 | 55 ± 6.0 | 57 ± 6.2 | 137 ++± 14.3 |
| Lycopene MUFA Increment Δ in serum lycopene concentration, in ng/ml | | | | Lycopene SFA Increment Δ in serum lycopene concentration, in ng/ml | | | |
| Postprandial time | | | AUC | Postprandial time | | | AUC |
| 1 h | 2 h | 3 h | 1-3 hours | 1 h | 2 h | 3 h | 1-3 hours |
| 17.8 ± 2.1 | 33.3 ± 3.8 | 42.2 ± 4.5 | 93.3 ± 9.7 | 12.2 ± 1.3 | 30.0 ± 3.5 | 14.4 ± 1.6 | 56.6 ± 6.3 |

*Lycopene dose 7 mg with 50 g of olive oil or 50 g of cocoa butter.

Changes in concentration of Lycopene were detectable this time in both experiments (see the bottom half of Table 8). Ingestion of lycopene in MUFA provided significantly higher increase in the postprandial serum than its ingestion in SFA, 1.65 times difference with p<0.01.

6.3 Peripheral Tissue Concentrations

To validate that the boost in bypassing liver traffic of lycopene by chylomicrons with predominantly unsaturated fatty acids benefits the access of carotenoid, we next decided to measure for the possible appearance in the ear wax, or cerumen, of Lycopene. Table 9 below summarizes the results obtained and demonstrates that lycopene in PUFA formulation, after supplementation for 4 weeks, provided the highest increase in the ear wax of the lycopene concentration, 116±12.3 ng/mg, against MUFA based formulation, 65±7.3 ng/ml, p<0.01. The increment in the increase of lycopene concentration in the cerumen, after the same period of supplementation with SFA formulation, was lowest amongst all three products. Hence, again, the results show that it is possible to bypass delivery via the liver, instead targeting delivery into the peripheral tissues, through the use of PUFA or MUFA, rather than SFA.

TABLE 9

Changes in serum lycopene concentration after supplementation
with formulations of different fatty acids - 4 weeks trial.

| | | cerumen lycopene concentration, in ng/mg | | |
|---|---|---|---|---|
| Products | n | 0 weeks | 2 weeks | 4 weeks |
| Lycopene SFA | 8 | 53 ± 6.4 | 51 ± 5.9 | 102 ± 11.5 Δ = 49 |
| Lycopene PUFA | 8 | 29 ± 8.3 | 80 ± 9.1 Δ = 49 | 145 ± 16.2 Δ = 116 |
| Lycopene MUFA | 8 | 0 | 11 ± 6.7 Δ = 11 | 65 ± 7.8 Δ = 65 |

*Lycopene - 7 mg daily dose in one capsule

6.4 Blood Pressure Control

Carotenoid rich adrenal glands are essential in controlling a number of essential physiological processes in the body, including blood pressure (BP). Hence, again the ability to selectively target carotenoids represents a significant advantage. There are a number of publications that lycopene supplementation or tomato-rich diet can improve impaired parameters of the vasculature system, and BP in particular [11, 12]. However, these results are not always reproducible, and this could be due to variable dietary factors, differences in food matrices, which often are incomparable to variable supplement excipients [13, 14]. Given the results seen above, we further studied the ability of our approach as a possible way to produce formulations of lycopene that maximize its delivery to the main circulation, bypassing the liver, so providing the maximum chance for those other organs and tissues rich with carotenoid receptors to benefit from this extra available lycopene. To verify this possibility, the impact of the formulations on the parameters of systolic and diastolic blood pressure in volunteers with pre-hypertension was studied. PUFA based formulations of lycopene, which from the previous results discussed above facilitate the direct delivery to the main circulation, were compared with SFA formulations.

The data in Table 10 below indicated that four weeks of supplementation with lycopene-PUFA resulted in significantly stronger reduction of the elevated systolic and diastolic blood pressure than supplementation with the same dose of lycopene but in the SFA formulation. The reduction of the systolic BP for the former with 20 mg of lycopene was by 10±2.4 mmHg, and for the later formulation, with the same amount of this carotenoid, by 2.1±1.8 mmHg, p<0.005. Reduction of the diastolic BP lycopene PUFA was by 7.1±1.1 mmHg and for the lycopene-SFA 2.2±0.4 mmHg, p<0.01. Hence, again, PUFA based formulations were capable of promoting delivery of lycopene in such a way as to bypass the liver and have more impact on peripheral tissues, with the results showing the utility of such an approach on impacting on blood pressure. It was also interesting to note that there was a good lycopene dose dependent effect. When the dose of lycopene was increased to 40 mg, the reduction of elevated blood pressure was even more profound, by 15.1 mmHg for the systolic, and by 12.2 mmHg for diastolic BP. Furthermore, when the dose of lycopene was increased up to 60 mg per day the reduction for the systolic blood pressure was even more pronounced, by 20.6 mmHg. There was no additional decrease in the diastolic blood pressure.

The data obtained indicates that unsaturated, particularly polyunsaturated fatty acid (PUFA) formulations can be effective facilitator for lycopene. Indeed, in these experiments lycopene served as a model compound and the results obtained may also be applied to other compounds, for instance examples of other compounds that the approach may be employed to include other carotenoid and hydrophobic/lipophilic molecules. Hence, by choosing whether a SFA, PUFA or MUFA is employed it appears possible to select whether delivery is to the portal vein and hence the liver or alternatively to select bypass of the liver with increased delivery to the peripheral tissues. Further, the results show that such selective delivery may be used to help target a particular parameter, in this case using PUFA or MUFA to reduce transport to the liver, make lycopene more available for other organs and tissues has been shown as a way to help control vasculature functions and the blood pressure.

TABLE 10

Changes in systolic and diastolic blood pressure in volunteers with pre-hypertension after supplementation with lycopene formulated with different fatty acids - 4 weeks trial.

| Products | n | Systolic Blood Pressure, in mm Hg | | Diastolic Blood Pressure, in mm Hg | |
|---|---|---|---|---|---|
| | | 0 w | 4 w | 0 w | 4 w |
| Lycopene* PUFA | 6 | 135.2 ± 11.4 | 125.2 ± 10.8 $\Delta = -10$, $p < 0.001$ | 86.1 ± 8.3 | 79.0 ± 7.8 $\Delta = -7.1$, $p < 0.01$ |
| Lycopene** PUFA | 6 | 137.5 ± 12.3 | 122.4 ± 10.8 $\Delta = -15.1$, $p < 0.001$ | 87.2 ± 8.9 | 75.0 ± 7.7 $\Delta = -12.2$, $p < 0.01$ |
| Lycopene*** PUFA | 6 | 138.8 ± 13.1 | 118.2 ± 11.0 $\Delta = -20.6$, $p < 0.001$ | 85.9 ± 8.9 | 74.0 ± 7.7 $\Delta = -11.9$, $p < 0.01$ |
| Lycopene* SFA | 6 | 137.1 ± 12.3 | 135.0 ± 12.1 $\Delta = -2.1$, $p > 0.05$ | 84.5 ± 7.6 | 82.3 ± 8.1 $\Delta = -2.2$, $p > 0.05$ |

*Lycopene - 20 mg daily dose in one capsule;
**Lycopene - 40 mg daily dose in one capsule;
***Lycopene - 60 mg daily dose in one capsule.

6.5 Targeting Tissue Hypoxia

The ability to selectively target delivery was next studied as a way to restore oxygen saturation, $StO_2$, in a hypoxia stress-test, which represents an important tissue parameter. Hence, PUFA and MUFA formulations of lycopene which bypass the liver were again compared with an SFA Lycopene formulation that does not. The data obtained is presented below in Table 11 demonstrated that that supplementation of the volunteers with MUFA and in particular with PUFA formulation of lycopene resulted in a significantly higher increase in $StO_2$, than in the group which took SFA lycopene.

It was interesting to note that although the impact of MUFA on $StO_2$ was only slightly higher than that seen for the SFA formulation, the impact of the MUFA formulation in terms of boosting oxygen transport in circulation as measured per every nanogram increase in of lycopene was 2.5 times higher than for the PUFA formulation and 3.6 greater than that seen for the SFA formulations.

TABLE 11

Changes in plasma oxygen supply and tissue oxygen saturation in skin, subcutaneous fat and skeletal muscles in volunteers after supplementation with lycopene formulated with different fatty acids 4 weeks trial.

| Products | n | Tissue Oxygen Saturation $StO_2$, in AUC mm | | $\Delta$ in plasma oxygen µM $O_2/\Delta$ in lycopene concentration in ng |
|---|---|---|---|---|
| | | 0 weeks | 4 weeks | |
| Lycopene PUFA | 8 | 64 ± 4.9 | 89 ± 6.6 ($\Delta = +25$) $p < 0.01$ | 1.7 µM $O_2$:1 ng Lyc |
| Lycopene MUFA | 8 | 62 ± 5.1 | 80 ± 7.4 ($\Delta = +20$) $p < 0.01$ | 4.3 µM $O_2$:1 ng Lyc |
| Lycopene SFA | 8 | 56 ± 4.2 | 75 ± 5.5 ($\Delta = +19$) $p < 0.01$ | 1.2 µM $O_2$:1 ng Lyc |

*Lycopene - 7 mg daily dose in one capsule.

The results obtained therefore indicate that MUFA and in particular PUFA embedment/formulation provides an effective way to bypass liver delivery and so allow for more effective delivery to the peripheral tissues, including as a way to influence oxygen saturation. Hence, through the choice of formulation, the approach provided can be used as a way for management, for example, of age-associated or disease related sub-clinical or clinically manifested hypoxic conditions or pathologies, such as sarcopenia or cancer.

6.6 Prostate Hyperplasia

There is a significant body of literature linking higher level of lycopene with lower incidence of the prostate cancer [15-18]. However, interventional studies with s lycopene rich dietary products or supplements with this carotenoid showed either positive or not beneficial, i.e. inconclusive results [19, 20]. Again this could be due to variability in dietary factors, differences in food matrixes, which often are incomparable to variable supplement excipients [13, 14]. One of the main reasons behind prostate hyperplasia is a development of hypoxic conditions in the prostate tissue [21,22].

To assess and compare possible effects of two lycopene formulations on symptoms patients with benign prostatic hyperplasia (BPH) we did a proof of concept double-blind study using PUFA and SFA formulations. The study therefore recruited 8 men of 51 to 70 years old, with moderate International Prostate Symptom Score, IPSS, of >16. Apart for BPH the subjects did not have any other medical conditions and were not taking any medications or lycopene supplements. The individuals were split into two groups of 4 and randomized on their age and body mass. The trial lasted for 3 months.

The results of the study are presented below in Table 12. They show that both PUFA and SFA lycopene formulations make a significant improvement of the IPSS. However, the effect of the former PUFA formulation was three times more effective than the latter, p<0.001.

TABLE 12

Changes in the total prostate function, IPSS, in volunteers with prostate hypertrophy after supplementation with lycopene formulated with different fatty acids - 3 months trial

| Products | n | IPSS Baseline | IPSS After 3 months |
|---|---|---|---|
| Lycopene PUFA | 4 | 19.4 ± 4.1 | 7.1 ± 2.2<br>Δ = −12.3<br>p < 0.001 |
| Lycopene SFA | 4 | 18.5 ± 4.3 | 14.4 ± 3.7<br>Δ = −4.1<br>p < 0.05 |

*Lycopene - 40 mg daily dose in one capsule.

The small scale trial performed on the 8 subjects provided an indication that peripheral organs as the prostate can benefit more when more lycopene was transported to the circulation by chylomicrons, than when it went to the liver first.

Example 7 Studies with Other Carotenoids—Astaxanthin, Lutein, Meso Zeaxanthin and Zeaxanthin 7.1 Introduction Astaxanthin, Lutein, its isomer Meso-Zeaxanthin, which typically occur in naturally extracted lutein preparations, and Zeaxanthin are molecules belonging to xanthophyll group of compounds of oxygenated carotenoids. Astaxanthin, Lutein, Meso-Zeaxanthin and Zeaxanthin are potent antioxidants and like other hydrophobic carotenoids are most effective within lipid or membrane cell structures. Due to the same hydrophobic properties as Lycopene both of them do not enter directly into existing lipid structures, but are instead incorporated at the time of their assembly. Lycopene, astaxanthin, lutein, meso-zeaxanthin and Zeaxanthin are the main hydrophobic carotenoids in the human body and are present in almost all of its organs and tissues. As in the case of lycopene, the liver is the main organ which can effectively excrete excessive lutein and zeaxanthin back to the intestine via biliary system. Whilst lycopene is predominately carried by LDL, astaxanthin, lutein and zeaxanthin can be incorporated and carried by any lipoprotein particles. Another difference of lutein and zeaxanthin compared to lycopene is that due to their charged hydroxyl groups, these two carotenoids more easily cross the blood-brain barrier (BBB) compared to lycopene. That fact allows them to be among the main carotenoids in the brain and retina tissues.

To boost chylomicron transport of the absorbed molecules of astaxanthin, lutein and zeaxanthin, and facilitate their by-passing of the liver, formulations of these carotenoids were developed with unsaturated fatty acids, MUFA and PUFA. We compared the pharmacokinetics and pharmacodynamics of those formulations with carotenoids embedded into SFA, which from the studies described above facilitate transport via the portal vein system and then directly to the liver.

7.2 Plasma Concentration

Table 13 below demonstrates that after 4 weeks of supplementation the PUFA lutein, meso-zeaxanthin-zeaxanthin, LMZ, formulation provided the highest increase of lutein concentration in the serum, by 540±5.4 ng/ml, against 400±4.1 ng/ml for SFA formulation. For zeaxanthin the pharmacokinetics were slightly different. The maximum concentration was again for the PUFA formulation, with it reaching its peak at the second week of supplementation, by 29 ng/ml. By the fourth week of supplementation with the PUFA zeaxanthin formulation the concentration in the serum went down, and the difference with the baseline level was reduced to 22 ng/ml. For the MUFA formulation the maximum of the zeaxanthin concentration was by 25 ng/ml on the $4^{th}$ week.

Overall, the SFA formulation provided the lowest increment in the zeaxanthin concentration, 13 ng/ml, by the end of the trial.

TABLE 13

Changes in serum lutein concentration after supplementation with formulations of different fatty acids - 4 weeks trial.

| Products | n | serum lutein concentration, in ng/ml | | | serum zeaxanthin concentration, in ng/ml | | |
|---|---|---|---|---|---|---|---|
| | | 0 weeks | 2 weeks | 4 weeks | 0 weeks | 2 weeks | 4 weeks |
| LMZ MUFA | 8 | 150 ± 16 | 410 ± 53<br>Δ = 260 | 540 ± 57<br>Δ = 390 | 18 ± 1.9 | 28 ± 2.3<br>Δ = 10 | 43 ± 4.1<br>Δ = 25 |
| LMZ PUFA | 8 | 190 ± 21 | 720 ± 69<br>Δ = 530 | 730 ± 70<br>Δ = 540 | 21 ± 2.3 | 50 ± 4.8<br>Δ = 29 | 43 ± 3.9<br>Δ = 22 |
| LMZ SFA | 8 | 150 ± 17 | 520 ± 55<br>Δ = 370 | 550 ± 61<br>Δ = 400 | 22 ± 1.9 | 41 ± 35<br>Δ = 19 | 35 ± 3.3<br>Δ = 13 |

*Lutein:meso-zeaxanthin 50%:50% 7 mg combined 7 mg and Zeaxanthin 1.4 mg - daily dose in one capsule.

Table 14 demonstrates that after 4 weeks of supplementation the PUFA astaxanthin, formulation provided the highest increase of astaxanthin concentration in the serum, by 40 ng/ml, against 21 ng/ml for SFA formulation

TABLE 14

Changes in serum astaxanthin concentration after supplementation with formulations of different fatty acids - 4 weeks trial.

| | | serum lutein concentration, in ng/ml | |
|---|---|---|---|
| Products | n | 0 weeks | 4 weeks |
| Astaxanthin PUFA | 8 | 0 | 40 + 3.9 |
| Astaxanthin MUFA | 8 | 0 | 39 + 3.7 |
| Astaxanthin SFA | 8 | 0 | 21 + 2.8 |

7.3 Lipoprotein Protection from Oxidation

Next a study of the ability of the formulations to protect from oxidation was made. Table 15 summarizes the results and demonstrates that MUFA LMZ formulation provide the fastest and the deepest inhibition of LDL peroxidation, LDL-Px, by $95 \pm 10.1 \times 10^{-3}$ as measured by ELISA on the second week of supplementation. By the end of the trial the inhibition for that formulation was by $208 \pm 22.3 \times 10^{-3}$ ELISA.

For the PUFA formulation the reduction for the same period by the end of the trial of this parameter was $65 \pm 9.2$, $p<0.01$ against the MUFA formulation and for the SFA formulation the inhibition was $100 \pm 6.8 \times 10^{-3}$ ELISA, $p<0.001$ against the MUFA formulation and $p<0.05$ against the PUFA formulation.

TABLE 15

Changes in the level of LDL-peroxidation in the serum of volunteers after supplementation with LMZ formulated with different fatty acids - 4 weeks trial

| | | LDL-Px × $10^{-3}$ ELISA | | |
|---|---|---|---|---|
| Products | n | 0 weeks | 2 weeks | 4 weeks |
| LMZ MUFA | 8 | 237 ± 32 | 142 ± 16 (60%) $\Delta = -95$ $p < 0.001$ | 29 ± 11 (12%) $\Delta = -208$ $p < 0.001$ |
| LMZ PUFA | 8 | 147 ± 18 | 138 ± 15 (94%) $\Delta = -9$ $p > 0.05$ | 62 ± 9 (42%) $\Delta = -65$ $p < 0.01$ |
| LMZ SFA | 8 | 290 ± 34 | 232 ± 25 (80%) $\Delta = -58$ $p < 0.01$ | 190 ± 22 (66%) $\Delta = -100$ $p < 0.001$ |

* Lutein:meso-zeaxanthin 50%:50% 7 mg combined and Zeaxanthin 1.4 mg - daily dose in one capsule.

7.4 Inflammatory Oxidative Damage

Astaxanthin is not only powerful antioxidant it is also has strong anti-inflammatory properties. We assess impact of formulation of this carotenoid with different fatty acids on this dual activity by measuring changes IOD in the blood of people who were positive on the presence of this marker. Results presented in the table 16 indicate that astaxanthin PUFA was two times stronger than its SFA formulation. After 4 weeks of supplementation the former product inhibited IOD by 125 µM, but the latter by 58 µM.

TABLE 16

Changes in the level of Inflammatory Oxidative Damage in the serum of volunteers after supplementation with astaxanthin formulated with different fatty acids - 4 weeks trial.

| | | IOD in MDA µM | |
|---|---|---|---|
| Products | n | 0 weeks | 4 weeks |
| Astaxanthin PUFA | 8 | 227 ± 23 | 102 ± 7 $\Delta = -125$ $p < 0.001$ |
| Astaxanthin MUFA | 8 | 199 ± 19 | 120 ± 12 $\Delta = -79$ $p < 0.005$ |
| Astaxanthin SFA | 8 | 188 ± 18 | 130 ± 14 $\Delta = -58$ $p < 0.01$ |

Tissue Hypoxia Target

From the results presented above, it was found that unsaturated, in particular polyunsaturated fatty acid formulations, are effective facilitators of the chylomicron transportation of lycopene, with the formulations increasing availability of the carotenoids for other organs and tissues. To verify further that the approach can be applied for lutein and zeaxanthin, we also compared the efficacy of PUFA and MUFA formulation of those carotenoids with a SFA formulation on the important tissue parameter as its ability to restore oxygen saturation, $StO_2$, after a hypoxia stress-test.

The data obtained is presented in Table 17 below and demonstrates that supplementation of the volunteers with MUFA and in particular with PUFA formulation of LMZ resulted in faster and significantly higher increase in $StO_2$, than in the group which took SFA LMZ.

TABLE 17

Changes in plasma oxygen supply and tissue oxygen saturation in skin, subcutaneous fat and skeletal muscles in volunteers after supplementation with LMZ formulated with different fatty acids - 4 weeks trial.

| | | Tissue Oxygen Saturation $StO_2$, in AUC mm | | |
|---|---|---|---|---|
| Products | n | 0 w | 2 w | 4 w |
| LMZ MUFA | 8 | 49 ± 7.1 | 74 ± 6.2 ($\Delta = +25$) $p < 0.01$ | 81 ± 7.0 ($\Delta = +32$) $p < 0.01$ |
| LMZ PUFA | 8 | 47 ± 5.0 | 70 ± 6.1 ($\Delta = +23$) $p < 0.01$ | 81 ± 8.3 ($\Delta = +34$) $p < 0.01$ |
| LMZ SFA | 8 | 50 ± 5.5 | 57 ± 5.5 ($\Delta = +7$) $p > 0.05$ | 66 ± 6.2 ($\Delta = +16$) $p < 0.05$ |

* Lutein:meso-zeaxanthin 50%:50% 7 mg combined 7 mg and Zeaxanthin 1.4 mg - daily dose in one capsule.

The results therefore further confirm that both MUFA and PUFA formulations help bypass liver delivery and instead boost chylomicron transportation of lutein and zeaxanthin giving much effective delivery to the peripheral tissues.

These formulations can be use for management, for example, of age-associated or disease related sub-clinical or clinically manifested hypoxic conditions or pathologies, and in particular in the neuron tissues, brain and retina, etc.

REFERENCES

1. Walz C P, Barry A R, Koshman S L—Omega-3 polyunsaturated fatty acid supplementation in the prevention of cardiovascular disease.—*Can Pharm J* (Ott). 2016 May: 149(3):166-7.

2. Backes J, Anzalone D, Hilleman D, Catini J—The clinical relevance of omega-3 fatty acids in the management of hypertriglyceridemia.—*Lipids Health Dis.* 2016 Jul. 22: 15(1):118.
3. Bazan N G, Musto A E, Knott E J.—Endogenous signaling by omega-3 docosahexaenoic acid-derived mediators sustains homeostatic synaptic and circuitry integrity.— *Mol Neurobiol.* 2011 October; 44(2):216-22.
4. Weiser M J1, Butt C M2, Mohajeri M H3. Docosahexaenoic Acid and Cognition throughout the Lifespan.— *Nutrients.* 2016 Feb. 17; 8(2):99. doi: 10.3390/nu8020099.
5. Kevin L Fritsche—The Science of Fatty Acids and Inflammation.—*Adv Nutr.* 2015 May; 6(3): 293S-301S.
6. Stine M Ulven1 and Kirsten B Holven—Comparison of bioavailability of krill oil versus fish oil and health effect.—*Vasc Health Risk Manag.* 2015; 11: 511-524.
7. Wooki Kim1, David N. McMurray, and Robert S. Chapkin—omega-3 polyunsaturated fatty acids—physiological relevance of dose.—*Prostaglandins Leukot Essent Fatty Acids,* 2010: 82(4-6): 155-158.
8. Nadeem Tajuddin, Ali Shaikh, and Amir Hassan Prescription omega-3 fatty acid products: considerations for patients with diabetes mellitus.—*Diabetes Metab Syndr Obes.* 2016; 9: 109-118.
9. Bernstein A M1, Ding E L, Willett W C, Rimm E B. A Meta-Analysis Shows That Docosahexaenoic Acid from Algal Oil Reduces Serum Triglycerides and Increases HDL-Cholesterol and LDL-Cholesterol in Persons without Coronary Heart Disease.—*J Nutr.* 2012 January; 142(1):99-104.
10. Petyaev I. M Carotenoid particles and uses thereof.— Patent Application WO2012104576 A2, PCT/GB2012/000075, 2011
11. Ried K, Fakler P. Protective effect of lycopene on serum cholesterol and blood pressure: Meta-analyses of intervention trials.—Maturitas (2011), 68, 299-310.
12. Gajendragadkar P R, Hubsch A, Maki-Petaja K M, Serg M, Wilkinson I B, Cheriyan J. Effects of oral lycopene supplementation on vascular function in patients with cardiovascular disease and healthy volunteers: a randomised controlled trial.—PloS One (2014), 9(6) doi: 10.1371/journal.pone.0099070.
13. Ried K, Frank O R, Stocks N P. Dark chocolate or tomato extract for prehypertension: a randomised controlled trial.—BMC Complementary and Alternative Medicine (2009, 9:22, doi:10.1186/1472-6882-9-22.
14. Burton-Freeman B, Sesso H D. Whole food versus supplement: comparing the clinical evidence of tomato intake and lycopene supplementation on cardiovascular risk factors.—Adv Nutr (2014), 5(5), 457-485.
15. Mills P K, Beeson W L, Phillips R L, Frazer G E. Cohort study of diet, lifestyle, and prostate cancer in Adventist men. Cancer (1989), 64, 598-604.
16. Clinton S K, Emenhiser C, Schwartz S J, Bostwick D G, Willaims A W, Moore B J, Erdman J W Jr. Cis-trans Lycopene Isomers, Carotenoids, and Retinol in Human Prostate. Cancer Epidemiology, Biomarkers & Prevention (1996), 5, 823-833.
17. Giovanucci E. A review of epidemiologic studies of tomatoes, lycopene and prostate cancer. Experimental Biology Medicine 2002; 227:852-8.
18. Barber N J, Barber J. Lycopene and prostate cancer.— Prostate Cancer and Prostatic Diseases (2002), 5, 6-12.
19. Schwartz S, Obermuller-Jevic U C, Hellmis E, Koch W, Jacobi G, Biesalski H K. Lycopene Inhibits Disease Progression in Patients with Benign Prostate Hyperplasia. J Nutr (2008), 138(1), 49-53.
20. Breemen R B, Sharifi R, Viana M, Pajkovic N, Zhu D, Yuan L, Yang Y, Bowen P E, Stacewicz-Sapuntzakis M. Antioxidant Effects of Lycopene in African American Menwith Prostate Cancer or Benign Prostate Hyperplasia: A Randomized, Controlled Trial.—Cancer Prev Res (2011), 4(5), 711-718.
21. Hansen-Smith F M. Capillary Network Patterning During Angiogenesis. Clin Exp Pharmacol Physiol. (2000), 27:830-5.
22. Baldwin A L. A brief history of capillaries and some examples of their apparently strange behavior. Clin Exp Pharmacol Physiol. (2000), 27, 821-825.

The invention claimed is:

1. A non-aqueous pharmaceutical or nutraceutical composition, comprising:
   1-15% w/w of at least one carotenoid;
   2-20% w/w phosphatidylcholine; and
   at least 20% w/w saturated fatty acid;
   wherein amounts of at least one carotenoid and the phosphatidylcholine are of the same order of magnitude, and an amount of the saturated fatty acid is larger than the amount of each of the at least one carotenoid and the phosphatidylcholine by an order of magnitude,
   wherein the at least one carotenoid includes lycopene and the saturated fatty acid is sourced from cocoa butter, and
   wherein the composition comprises 3.5 to 14 mg of lycopene.

2. A non-aqueous pharmaceutical or nutraceutical composition, comprising:
   1-15% w/w of at least one carotenoid;
   2-20% w/w phosphatidylcholine; and
   at least 20% w/w polyunsaturated fatty acid;
   wherein amounts of at least one carotenoid and the phosphatidylcholine are of the same order of magnitude, and an amount of the polyunsaturated fatty acid is larger than the amount of each of the at least one carotenoid and the phosphatidylcholine by an order of magnitude,
   wherein the at least one carotenoid includes lycopene and the polyunsaturated fatty acid is sourced from sunflower oil, and
   wherein the composition comprises 3.5 to 14 mg of lycopene.

3. The pharmaceutical or nutraceutical composition of claim 1, wherein the composition further comprises at least one carotenoid selected from the group consisting of beta- and/or alpha-carotene, lutein, meso-zeaxanthin, zeaxanthin, and astaxanthin.

4. The pharmaceutical or nutraceutical composition of claim 1, consisting essentially of the at least one carotenoid; the phosphatidylcholine; and the saturated fatty acid.

5. A non-aqueous pharmaceutical or nutraceutical composition, consisting essentially of:
   1-15% w/w of at least one carotenoid;
   2-20% w/w phosphatidylcholine;
   and at least 20% w/w a saturated or polyunsaturated fatty acid;
   wherein amounts of at least one carotenoid and the phosphatidylcholine are of the same order of magnitude, and an amount of the polyunsaturated fatty acid is larger than the amount of each of the at least one carotenoid and the phosphatidylcholine by an order of magnitude, wherein the at least one carotenoid comprises lycopene, and wherein the composition comprises 3.5 to 14 mg of lycopene.

6. The pharmaceutical or nutraceutical composition of claim 5, wherein the composition further comprises at least one carotenoid selected from the group consisting of beta- and/or alpha-carotene, lutein, meso-zeaxanthin, zeaxanthin, and astaxanthin.

7. The pharmaceutical or nutraceutical composition of claim 6, wherein the polyunsaturated fatty acid is sourced from sunflower oil.

8. The pharmaceutical or nutraceutical composition of claim 6, wherein the saturated fatty acid is sourced from cocoa butter.

\* \* \* \* \*